(12) United States Patent
Bryans et al.

(10) Patent No.: US 7,442,795 B2
(45) Date of Patent: Oct. 28, 2008

(54) TRIAZOLE COMPOUNDS USEFUL IN THERAPY

(75) Inventors: Justin Stephen Bryans, Sandwich (GB); Patrick Stephen Johnson, Sandwich (GB); Thomas Ryckmans, Sandwich (GB); Alan Stobie, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/416,498

(22) Filed: May 1, 2006

(65) Prior Publication Data
US 2006/0194794 A1    Aug. 31, 2006

Related U.S. Application Data

(62) Division of application No. 10/782,285, filed on Feb. 18, 2004, now Pat. No. 7,119,088.

(60) Provisional application No. 60/455,455, filed on Mar. 18, 2003.

(30) Foreign Application Priority Data
Feb. 19, 2003    (GB)    ................... 0303852.8

(51) Int. Cl.
*C07D 401/14*    (2006.01)
*C07D 413/14*    (2006.01)

(52) U.S. Cl. .................. 544/328; 546/193; 546/210; 546/269.1; 548/143

(58) Field of Classification Search .................. 544/328; 546/193, 210, 269.1; 548/143
See application file for complete search history.

(56) References Cited

U.S. PATENT DOCUMENTS

| | | | | |
|---|---|---|---|---|
| 4,663,321 | A | 5/1987 | Bock et al. | 514/220 |
| 4,959,361 | A | 9/1990 | Walser | 514/220 |
| 4,987,131 | A | 1/1991 | Clemence et al. | 514/220 |
| 5,438,035 | A | 8/1995 | Guaciaro et al. | 504/191 |
| 5,521,173 | A | 5/1996 | Vankatesan et al. | 514/220 |
| 7,064,120 | B2 | 6/2006 | Failli et al. | 514/220 |
| 2005/0049255 | A1* | 3/2005 | Bictash et al. | 514/252.16 |

FOREIGN PATENT DOCUMENTS

| | | |
|---|---|---|
| EP | 0362942 | 9/1989 |
| JP | 6128262 | 5/1994 |
| JP | 6135965 | 5/1994 |
| JP | 9132576 | 5/1997 |
| JP | 9328484 | 12/1997 |
| JP | 0063363 | 2/2000 |
| WO | WO9749707 | 12/1997 |
| WO | WO9820011 | 5/1998 |
| WO | WO0043398 | 7/2000 |
| WO | WO0158880 | 8/2001 |
| WO | WO02083678 | 10/2002 |

OTHER PUBLICATIONS

Hester, et al, "6-Aryl-4H-s-triazolo[4,3-a][1,4]benzodiazepines. Influence of 1-Substitution on Pharmacological Activity", *Journal of Medicinal Chemistry*, vol. 22(11), pp. 1390-1398 (1979).
Breslin, H., et al., Synthesis and Anti-HIV Activity of 1,3,4,5-Tetrahydro-2H-1,4-benzodiazepin-2-one (TBO) Derivatives. Truncated 4,5,6,7-Tetrahydro-5-methylimidazo[4,5,1-jk][1,4]benzodiazepin-2(1H)-ones (TIBO) Analogues, Pergamon Bioorganic & Medicinal Chemistry, 7 (1999) pp. 2427-2436, May 20, 1999.
Ashwood, Michael, S., et al., Synthesis of 5,6-Dihydro-4H-imidazo[1,5-a][4,1]benzoxazepin-6-ones and their Transformation into 5,6 Dihydro-4H-imidazo[1,5-a][1,4]benzodiazepin-6-ones, Journal of Chemical Soc. Perkin Trans, I, 1989, pp. 1889-1893.
Goel, O.P., et al., Reaction of Phosphorus Pentasulfide with Organolithiums. An In Situ Reagent for the Preparation of Thiolactams, Dept. of Chemistry, Warner-Lambert/Parke-Davis Pharmaceuticals Research, Communications, Feb. 1987, pp. 162-164.
Ajuebor, M., et al., Cyclooxygenase-2-derived prostaglandin $D_2$ is an early anti-inflammatory signal in experimental colitis; Am. J. Physiol. Gastrointest Liver Physiol., 279, pp. G238-G244, 2000.

* cited by examiner

*Primary Examiner*—Rei-tsang Shiao
*Assistant Examiner*—Joseph R Kosack
(74) *Attorney, Agent, or Firm*—Gregg C. Benson; John A. Wichtowski

(57) ABSTRACT

A compound of formula (I),

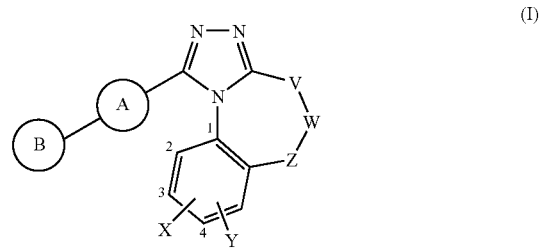

or a pharmaceutically acceptable derivative, wherein A, B, V, W, X, Y, and Z are as defined herein; pharmaceutical compositions thereof; and uses thereof.

2 Claims, No Drawings

TRIAZOLE COMPOUNDS USEFUL IN THERAPY

This application claims priority to U.S. Ser. No. 10/782,285, filed Feb. 18, 2004, now allowed, which claims priority to U.S. Provisional Application Ser. No. 60/455,455, filed Mar. 18, 2003, which claims priority to British Application Serial No. 0303852.8, filed Feb. 19, 2003.

This invention relates to novel compounds useful in therapy and to processes for the preparation of, intermediates used in the preparation of, compositions containing and the uses of, such derivatives.

Japanese Patent Application No. 09-328484 describes triazole quinoxalines useful as anti-allergy and anti-inflammatory agents. Japanese Patent Application No. 09-132576 describes triazole quinoxalines useful as anti-allergy and anti-inflammatory agents. Japanese Patent Application No. 06-135965 describes triazole quinoxalines useful for curing and preventing allergies, inflammation and PAF-associated diseases. Japanese Patent Application No. 06-128262 describes triazole quinoxalines useful for intermediates of drugs and agrochemicals.

The compounds of the present invention have been found to have useful pharmaceutical properties. They may be used to treat aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis.

Particularly of interest are the following diseases or disorders:

anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor and Raynaud's disease.

In particular, they exhibit vasopressin antagonistic activity and can be used in the treatment of dysmenorrhoea (primary and secondary).

There is a high unmet need in the area of menstrual disorders and it is estimated that up to 90% of all menstruating women are affected to some degree. Up to 42% of women miss work or other activities due to menstrual pain and it has been estimated that around 600 million work hours a year are lost in the US as a result (costing around $2 billion in lost productivity).

Menstrual pain in the lower abdomen is caused by myometrial hyperactivity and reduced uterine blood flow. These pathophysiological changes result in abdominal pain that radiates out to the back and legs. This may result in women feeling nauseous, having headaches and suffering from insomnia. This condition is called dysmenorrhoea and can be classified as either primary or secondary dysmenorrhoea.

Primary dysmenorrhoea is diagnosed when no abnormality causing the condition is identified. This affects up to 50% of the female population. Where an underlying gynaecological disorder is present, such as endometriosis, pelvic inflammatory disease (PID), fibroids or cancers, secondary dysmenorrhoea will be diagnosed. Secondary dysmenorrhoea is diagnosed in only approximately 25% of women suffering from dysmenorrhoea. Dysmenorrhoea can occur in conjunction with menorrhagia, which accounts for around 12% of referrals to gynaecology outpatients departments.

Currently, women suffering from primary dysmenorrhoea are treated with non-steroidal anti-inflammatory drugs (NSAID's) or the oral contraceptive pill. In cases of secondary dysmenorrhoea surgery may be undertaken to correct the underlying gynaecological disorder.

Women suffering from dysmenorrhoea have circulating vasopressin levels which are greater than those observed in healthy women at the same time of the menstrual cycle. Inhibition of the pharmacological actions of vasopressin, at the uterine vasopressin receptor, may prevent dysmenorrhoea.

According to the present invention there is provided a compound of formula (I),

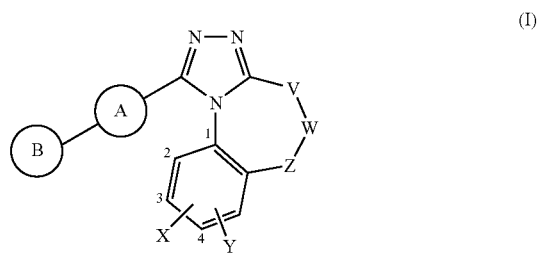

or a pharmaceutically acceptable derivative thereof, wherein

V represents —$(CH_2)_d(O)_e$—, —CO—, or —$CH(C_{1-6}$ alkyl)-;

W is —O—, —$S(O)_a$—, or —$N(R^1)$—
  $R^1$ represents H, $C_{1-6}$ alkyl, $(CH_2)_bCOR^2$, $CO(CH_2)_bNR^2R^3$, $SO_2R^2$, $(CH_2)_cOR^2$, $(CH_2)_cNR^2R^3$, or $(CH_2)_bhet^1$;
  $het^1$ represents a saturated or unsaturated heterocycle of from 3 to 8 atoms containing one or more heteroatoms selected from O, N, or S, optionally substituted with $C_{1-6}$ alkyl;

X and Y independently represent H, $C_{1-6}$ alkyl, halogen, OH, $CF_3$, $OCF_3$, $OR^4$;

Z represents —$(CH_2)_f(O)_g$—, —CO— or —$CH(C_{1-6}$ alkyl)-;

Ring A represents a 4-7 membered, saturated N-containing heterocycle, optionally substituted with OH, and in which optionally at least one ring N is substituted with O;

Ring B represents phenyl or a 4-7 membered unsaturated N-containing heterocycle, optionally substituted with OH, halogen, CN, $CONH_2$, $CF_3$, $OCF_3$, and in which optionally at least one ring N is substituted with O;

$R^2$ and $R^3$ independently represent H, $C_{1-6}$ alkyl [optionally substituted with OH, halogen, $N(C_{1-6}$ alkyl)$_2$, or $C_{1-6}$ alkyloxy], $C_{1-6}$ alkyloxy, $N(C_{1-6}$ alkyl)$_2$, or [$C_{3-8}$ cycloalkyl];

or R² and R³, together with the nitrogen atom to which they are attached independently represent a heterocycle of from 3 to 8 atoms, optionally substituted with $C_{1-6}$ alkyl;

R⁴ represents straight or branched $C_{1-6}$ alkyl, a and c independently represent 0, 1, or 2;

b, e and g independently represent 0 or 1;

d and f independently represent 1 or 2.

In the above definitions, halogen means fluoro, chloro, bromo or iodo. Alkyl groups containing the requisite number of carbon atoms, except where indicated, can be unbranched or branched chain. Examples include methyl, ethyl, n-propyl, i-propyl, n-butyl, i-butyl, sec-butyl and t-butyl. Examples of cycloalkyl include cyclopropyl, cyclobutyl, cyclopentyl, cyclohexyl and cycloheptyl. Examples of alkyloxy include methoxy, ethoxy, n-propyloxy, l-propyloxy, n-butyloxy, l-butyloxy, sec-butyloxy and t-butyloxy.

Heterocycles included within the definition of "heterocycle" are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl and quinoxalinyl, together with partially or fully saturated versions thereof as well as azetidinyl, pyrrolidinyl, piperidinyl, piperazinyl, homopiperazinyl, oxazepanyl, and morpholinyl.

Preferred groups of compounds are those in which any one or more of the following apply:

(i) W is $NR^1$;
(ii) $R^1$ is $C_{1-6}$ alkyl, and more preferably methyl, i-propyl or n-butyl;
(iii) $R^1$ is H;
(iv) $R^1$ is $(CH_2)_b het^1$;
(v) $het^1$ is pyrrolidinyl, piperidinyl, morpholinyl, azetidinyl, oxazepanyl, pyrimidinyl, pyridinyl, thiazolyl, or imidazolyl, (optionally substituted with $C_{1-6}$ alkyl)
(vi) $R^1$ is $CO(CH_2)_b NR^2 R^3$;
(vii) $R^2$ is morpholinyl or pyrimidinyl (optionally substituted with $C_{1-6}$ alkyl [optionally substituted with OH, halogen, $N(C_{1-6}alkyl)_2$, or $C_{1-6}alkyloxy$] or $NMe_2$).
(viii) $R^2$ and $R^3$ together with the nitrogen to which they are attached represent morpholinyl, pyrrolidinyl, piperazinyl, azetidinyl, tetrahydropyranyl, pyrimidinyl or piperidinyl (optionally substituted with $C_{1-6}$ alkyl)
(ix) V is —$(CH_2)_d(O)_e$—;
(x) Z is —$(CH_2)_f(O)_g$—;
(xi) d is 1;
(xii) e is 0;
(xiii) f is 1;
(xiv) g is 0;
(xv) X is H;
(xvi) Y is in the 4-position of the phenylene ring (according to the numbering of formula (I)) to which it is attached;
(xvii) Y is halogen, preferably chloro;
(xviii) Y is alkyloxy, preferably methoxy;
(xix) Y is alkyl, preferably methyl;
(xx) Y is $CF_3$ or $OCF_3$;
(xxi) Z is $(CH_2)_d(O)_e$;
(xxii) e is 0;
(xxiii) d is 1;
(xxiv) ring A is linked to ring B via a nitrogen atom in ring A;
(xxv) ring A is piperidinyl (optionally substituted with OH, and optionally at least one N is substituted with O);
(xxvi) ring B is pyridinyl (optionally substituted with one or more groups selected from OH, halogen, CN, $CONH_2$, $CF_3$, $OCF_3$, and optionally at least one ring N is substituted with O), preferably it is 2-pyridinyl;
(xxvii) ring B is pyrimidinyl (optionally substituted with one or more groups selected from OH, halogen, CN, $CONH_2$, $CF_3$, $OCF_3$, and optionally at least one ring N is substituted with O), preferably 2-pyrimidinyl;
(xxviii) n is 1;
(xxix) n is 2.

Preferred compounds according to the present invention are:

8-Chloro-5-methyl-1-(3,4,5,6-tetrahydro-2H-[1,2']bipyridinyl-4-yl)-5,6-dihydro-4H-2,3,5,10b-tetraaza-benzo[e] azulene trihydrochloride;

8-Chloro-5-isopropyl-1-(3,4,5,6-tetrahydro-2H-[1,2']bipyridinyl-4-yl)-5,6-dihydro-4H-2,3,5,10b-tetraaza-benzo[e] azulene trihydrochloride;

1-[8-Chloro-1-(3,4,5,6-tetrahydro-2H-[1,2']bipyridinyl-4-yl)-4H,6H-2,3,5,10b-tetraaza-benzo[e]azulen-5-yl]-ethanone dihydrochloride;

8-Chloro-5-methanesulfonyl-1-(3,4,5,6-tetrahydro-2H-[1,2']bipyridinyl-4-yl)-5,6-dihydro-4H-2,3,5,10b-tetraaza-benzo[e]azulene;

8-Chloro-5-methyl-1-(1-pyrimidin-2-yl-piperidin-4-yl)-5,6-dihydro-4H-2,3,5,10b-tetraaza-benzo[e]azulene;

8-Chloro-5-methanesulfonyl-1-(1-pyrimidin-2-yl-piperidin-4-yl)-5,6-dihydro-4H-2,3,5,10b-tetraaza-benzo[e]azulene;

13-Chloro-8-methyl-3-(3,4,5,6-tetrahydro-2H-[1,2']bipyridinyl-4-yl)-2,4,5,8-tetraaza-tricyclo[9.4.0.0*2,6*]pentadeca-1(11),3,5,12,14-pentaene;

13-Chloro-3-(3,4,5,6-tetrahydro-2H-[1,2']bipyridinyl-4-yl)-8-oxa-2,4,5-triaza-tricyclo[9.4.0.0*2,6*]pentadeca-1(11),3,5,12,14-pentaene;

1-[8-Chloro-1-(3,4,5,6-tetrahydro-2H-[1,2']bipyridinyl-4-yl)-4H,6H-2,3,5,10b-tetraaza-benzo[e]azulen-5-yl]-2-dimethylamino-ethanone;

[8-Chloro-1-(3,4,5,6-tetrahydro-2H-[1,2']bipyridinyl-4-yl)-4H,6H-2,3,5,10b-tetraaza-benzo[e]azulen-5-yl]-morpholin-4-yl-methanone;

(+) or (−) 8-Chloro-5-(4-methyl-morpholin-2-ylmethyl)-1-(3,4,5,6-tetrahydro-2H-[1,2']bipyridinyl-4-yl)-5,6-dihydro-4H-2,3,5,10b-tetraaza-benzo[e]azulene;

8-Chloro-5-pyrimidin-2-yl-1-(3,4,5,6-tetrahydro-2H-[1,2'] bipyridinyl-4-yl)-5,6-dihydro-4H-2,3,5,10b-tetraaza-benzo[e]azulene;

8-Chloro-1-(3,4,5,6-tetrahydro-2H-[1,2']bipyridinyl-4-yl)-4H,6H-2,3,5,10b-tetraaza-benzo[e]azulene-5-sulphonic acid dimethylamide;

8-Chloro-1-(1-pyrimidin-2-yl-piperidin-4-yl)-4H,6H-2,3,5, 10b-tetraaza-benzo[e]azulene-5-sulphonic acid dimethylamide;

13-Chloro-9-methyl-3-(3,4,5,6-tetrahydro-2H-[1,2']bipyridinyl-4-yl)-2,4,5,9-tetraaza-tricyclo[9.4.0.0*2,6*]pentadeca-1(11),3,5,12,14-pentaene; and 13-Chloro-8-methyl-3-(1-pyrimidin-2-yl-piperidin-4-yl)-2, 4,5,8-tetraaza-tricyclo[9.4.0.0*2,6*]pentadeca-1(11),3,5, 12,14-pentaene.

Alternatively there is provided a compound of formula (I*),

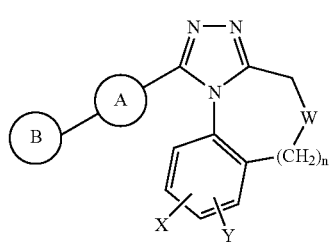

W is O, S, or NR$^1$
R$^1$ represents H, C$_{1-6}$ alkyl, —(CH$_2$)$_a$—[C$_{3-8}$ cycloalkyl], phenyl, benzyl, pyridyl, pyrimidyl, —COR$^2$, —CO$_2$R$^2$, —CO—(CH$_2$)$_a$—NR$^2$R$^3$, —SO$_2$R$^2$, —(CH$_2$)$_b$—OR$^2$, —(CH$_2$)$_b$—NR$^2$R$^3$, or a saturated heterocycle of from 3 to 8 atoms containing one or more heteroatoms selected from O, N and S;
X and Y independently represent H, halogen, OH, CF$_3$, OCF$_3$, R$^4$, —(CH$_2$)$_d$—CONR$^4$R$^5$, —(CH$_2$)$_d$—CN, —(CH$_2$)$_d$—SO$_2$NR$^4$R$^5$, —(CH$_2$)$_d$—NR$^4$SO$_2$Me, —(CH$_2$)$_d$—COR$^4$, —(CH$_2$)$_d$—OCOR$^4$, —(CH$_2$)$_d$—NH-COR$^4$, —(CH$_2$)$_d$—NR$^4$COR$^5$, —(CH$_2$)$_d$—OR$^6$ or —(CH$_2$)$_d$—CO$_2$R$^6$;
Ring A represents a piperidinyl, piperazinyl, pyrrolidinyl or azetidinyl group;
Ring B represents a phenyl, pyridinyl or pyrimidinyl group (optionally substituted with one or more groups independently selected from halogen, CN, CONH$_2$, CF$_3$, OCF$_3$, R$^7$, and —(CH$_2$)$_f$—OR$^8$);
R$^2$, R$^3$, R$^4$, R$^5$ and R$^7$ independently represent H, straight or branched C$_{1-6}$ alkyl, —(CH$_2$)$_c$—[C$_{3-8}$ cycloalkyl], phenyl, benzyl, pyridyl or pyrimidyl;
or R$^2$ and R$^3$, or R$^4$ and R$^5$, together with the nitrogen atom to which they are attached independently represent a heterocycle of from 3 to 8 atoms;
R$^6$ and R$^8$ independently represent H, straight or branched C$_{1-6}$ alkyl, —(CH$_2$)$_c$—[C$_{3-8}$ cycloalkyl], —(CH$_2$)$_e$—NR$^4$R$^5$, —(CH$_2$)$_e$—OR$^4$, phenyl, benzyl, pyridyl or pyrimidyl;
n=0, 1 or 2;
a, c, d and f are all independently selected from 0, 1, 2 or 3;
b and e are independently selected from 2 or 3.

Pharmaceutically acceptable derivatives of the compounds of formula (I) according to the invention include salts, solvates, complexes, polymorphs, prodrugs, stereoisomers, geometric isomers, tautomeric forms, and isotopic variations of compounds of formula (I). Preferably, pharmaceutically acceptable derivatives of compounds of formula (I) comprise salts, solvates, esters and amides of the compounds of formula (I). More preferably, pharmaceutically acceptable derivatives of compounds of formula (I) are salts and solvates.

The pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, D- and L-lactate, malate, maleate, malonate, mesylate, methylsulphate, naphthylate, 2-napsylate, nicotinate, nitrate, orotate, oxalate, palmitate, palmoate, phosphate, hydrogen phosphate, dihydrogen phosphate, saccharate, stearate, succinate, sulphate, D- and L-tartrate, tosylate and trifluoroacetate salts. A particularly suitable salt is the besylate derivative of the compounds of the present invention.

Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts see Stahl and Wermuth, Handbook of Pharmaceutical Salts: Properties, Selection and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components what may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) and pharmaceutically acceptable derivatives include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labelled compounds of formula (I).

As stated, the invention includes all polymorphs of the compounds of formula (I) as hereinbefore defined.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, hydrolytic cleavage. Such derivatives are referred to as "prodrugs". Further information on the use of prodrugs may be found in "Pro-drugs as Novel Delivery Systems, Vol. 14, ACS Symposium Series (T Higuchi and W Stella) and "Bioreversible Carriers in Drug Design", Pergamon Press, 1987 (ed. E B Roche, American Pharmaceutical Association).

Prodrugs in accordance with the invention can, for example, be produced by replacing appropriate functionalities present in the compounds of formula (I) with certain moieties know to those skilled in the art as "pro-moieties" as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with $(C_1-C_8)$ alkyl;

(ii) where the compound of formula (I) contains an alcohol functionality (—OH), an ether thereof, for example, replacement of the hydrogen with $(C_1-C_6)$alkanoyloxymethyl; and (iii) where the compound of formula (I) contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Also within the scope of the invention are the metabolites of the compounds of formula (I) when formed in vivo.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible, and where the compound contains, for example, a keto or oxime group or an aromatic moiety, tautomeric isomerism ('tautomerism') may occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral HPLC.

Alternatively, the racemate (or racemic precursor) may be reacted with a suitable optically active compound, for example, an alcohol, or, in the case where the compounds of formula (I) contains an acidic or basic moiety, an acid or base such as tartaric acid or 1-phenylethylamine. The resulting diastereomeric mixture may be separated by chromatography and/or fractional crystallisation and one or both of the diastereomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention also includes all pharmaceutically acceptable isotopic variations of a compound of the formula (I) one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulphur such as $^{35}$S, fluorine such as $^{18}$F, iodine such as $^{123}$I and $^{125}$I, and chlorine such as $^{36}$Cl.

Certain isotopically-labelled compounds of formula (I), for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Pharmaceutically acceptable solvates in accordance with the invention include those wherein the solvent of crystallisation may be isotopically substituted, e.g. D$_2$O, d$_6$-acetone and d$_6$-DMSO.

According to the present invention there is also provided a process for the production of a compound of formula (I), which comprises:

a) reacting a compound of formula (II) with an acid catalyst

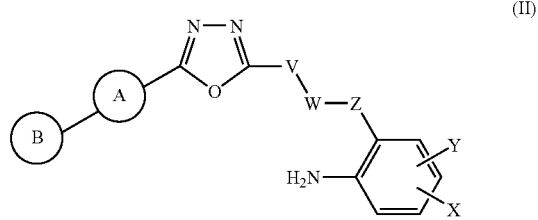

wherein rings A and B, and groups V, W, X, Y, Z and n are as defined above;

b) reacting a compound of formula (III)

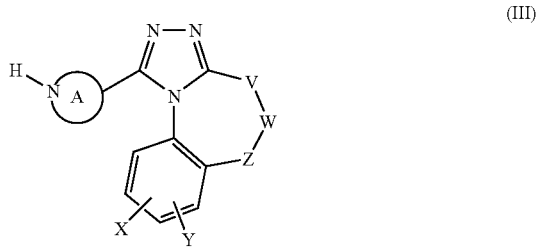

with a compound of formula (IV)

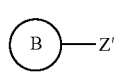
(IV)

wherein rings A and B, and groups V, W, X, Y, Z and n are as defined above, and Z' represents a leaving group such as halogen;

c) when W in compound (I) represents NR¹, reacting a compound of formula (V)

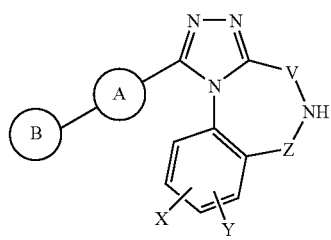
(V)

with a compound of formula (VI)

(VI)

wherein rings A and B, and groups R¹, V, X, Y, Z and n are as defined above, and Z" represents a leaving group such as halogen; or d) when W in compound (I) represents NR¹, reacting a compound of formula (V)

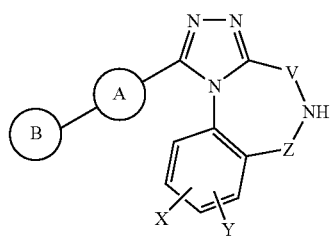
(V)

with a compound of formula (VII)

(VII)

wherein rings A and B, and groups R¹, V, X, Y, Z and n are as defined above;

e) reacting a compound of formula (XIII)

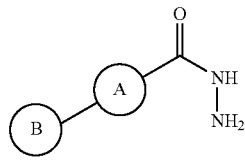
(XIII)

with a compound of formula (XXIV)

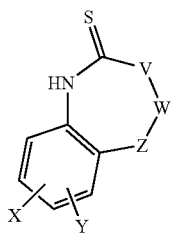
(XXIV)

wherein rings A and B, and groups V, W, X, Y and Z are as defined above;

f) reacting a compound of formula (XIII)

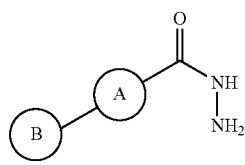
(XIII)

with a compound of formula (XXV)

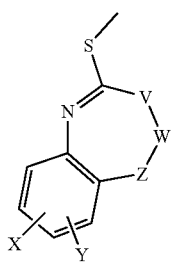
(XXV)

wherein rings A and B, and groups V, W, X, Y and Z are as defined above.

Unless otherwise provided herein:
WSCDI means 1-(3-dimethylaminopropyl)-3-ethylcarbodiimide hydrochloride;
DCC means N,N'-dicyclohexylcarbodiimide;
HOAT means 1-hydroxy-7-azabenzotriazole;
HOBT means 1-hydroxybenzotriazole hydrate;
PyBOP® means Benzotriazol-1-yloxytris(pyrrolidino)phosphoniumhexafluorophosphate;

PyBrOP® means bromo-tris-pyrrolidino-phosphonium-hexafluorophosphate;

HBTU means O-Benzotriazol-1-yl-N,N,N',N'-tetramethyluronium hexafluorophosphate.

Mukaiyama's reagent means 2-chloro-1-methylpyridinium iodide;

KHMDS means potassium bis(trimethylsilyl)amide;

Hünig's base means N-ethyldiisopropylamine;

Et₃N means triethylamine;

NMM means N-methylmorpholine;

HMDS means hexamethyldisilazane

BINAP means 2,2'-bis(diphenylphosphino)-1,1'-binaphthyl;

Dba means dibenzylideneacetone;

Boc means tert-butoxycarbonyl;

CBz means benzyloxycarbonyl;

p-TSA means p-toluenesulphonic acid

TBAF means tetra-butyl ammonium fluoride

MeOH means methanol, EtOH means ethanol, and EtOAc means ethyl acetate;

THF means tetrahydrofuran, DMSO means dimethyl sulphoxide, and DCM means dichloromethane, DMF means N,N-dimethylformamide, NMP means N-methyl-2-pyrrolidinone;

AcOH means acetic acid, TFA means trifluoroacetic acid;

Me means methyl, Et means ethyl;

Cl means chloro; and

OH means hydroxy.

The following schemes illustrate the preparation of compounds of the formula (I), throughout which Rings A and B, and groups V, W, X, Y, and n are as defined above unless otherwise stated. (I') represents (I) when W is $NR^1$.

Scheme 1.1

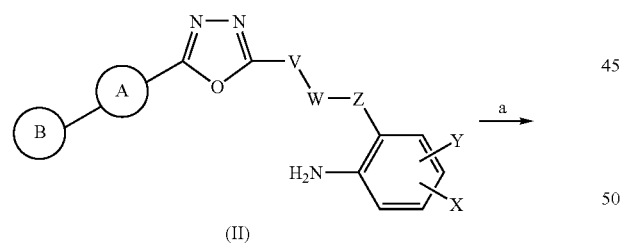

(II)

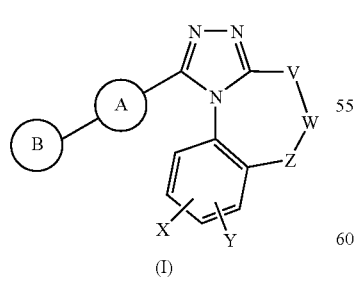

(I)

Step (a): Oxadiazole (II) is reacted with an acid catalyst to give the compound of formula (I). Typically the reaction is carried out by heating the starting materials to elevated temperatures, such as 50-150° C., for 1 to 48 hours with a suitable acidic catalyst such as p-TSA, trifluoroacetic acid or Lewis acid catalyst such as magnesium chloride, optionally using a solvent such as xylene, toluene or tetrahydrofuran.

Preferred Conditions are:
amine (II) and cat. P-TSA, in xylene at 140° C. for 48 hours; or
amine (II), trifluoroacetic acid in tetrahydrofuran at 60° C. for 24 hours.

When $W = NR^1$, then:

Scheme 1.2

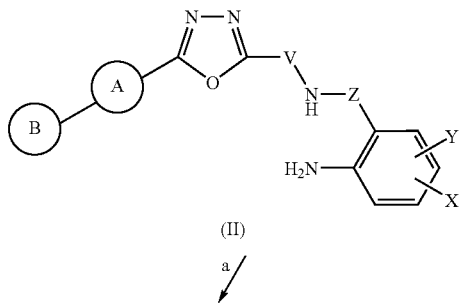

(II)

a↓

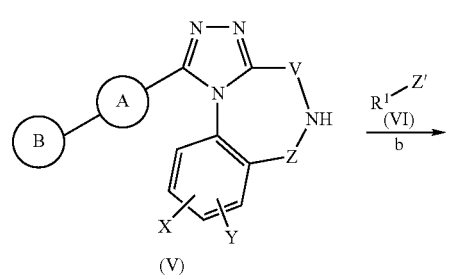

(V)

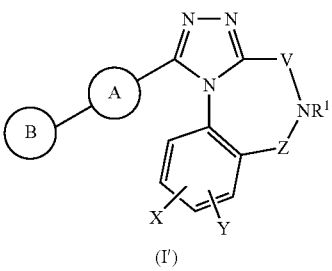

(I')

Z' is OH or halo, typically Cl

Compounds suitable for use as compound (VI) are commercially available or are known in the literature.

Step (b): The reaction of amine (V) with compound (VI) can be carried out by standard methods.

When $R^1 = (CH_2)_bCOR^2$, $CO(CH_2)_bNR^2R^3$, $SO_2R^2$ then, typically, the coupling may be undertaken by using:
(i) an acyl/sulphonyl/chloride (VI)+amine (V) with an excess of acid acceptor, in a suitable solvent; or
(ii) an acid (VI) with a conventional coupling agent+amine (V), optionally in the presence of a catalyst, with an excess of acid acceptor in a suitable solvent; and (iii) when R¹ represents an aryl group, an aryl halide (VI)+ amine (V), optionally in the presence of a catalyst, with an excess of acid acceptor in a suitable solvent.

Typically the conditions are as follows:

Acylation/Sulphonylation, Z'=Cl (i) An excess of acyl/sulphonyl chloride (VI) (generated in-situ), 1 eq. of amine (V), optionally with an excess of 3° amine such as Et₃N, Hünig's base or NMM, in DCM or THF, without heating for 1 to 24 hours.

The preferred conditions are:

Amine (V), 1.1-3.0 eq. acid/sulphonyl chloride (VI), 1.5-3 eq. NMM, Et₃N or pyridine in DCM at room temperature for 1-16 hours.

Amide Bond Formation, Z'=OH (ii) Excess acid (VI), WSCDI/DCC and HOBT/HOAT, 1 eq. of amine (V), with an excess of NMM, Et₃N, Hünig's base in THF, DCM or EtOAc, at room temperature for 4 to 48 hours; or excess acid (VI), PYBOP®/PyBrOP®/Mukaiyama's reagent/HBTU, 1 eq. of amine (V), with an excess of NMM, Et₃N, Hünig's base in THF, DCM or EtOAc, at room temperature for 4 to 24 hours.

The preferred conditions are:

amine (V), 2 eq. HBTU, 2 eq acid (R¹OH) in DCM at room temperature for 18 hours; or amine (V) HOBT, WSCDI, Et₃N, in DCM at room temperature for 18 hours.

Arylation (R¹=Aryl, Heteroaryl), Z'=Halo (iii) Arylation of compound (V) can be carried out by a palladium catalysed cross-coupling reaction using a suitable base (t-BuONa), a catalytic amount of suitable additive such as 2,2'-bis(diphenylphosphino)-1,1'-binaphthyl and a suitable palladium catalyst in toluene at elevated temp for 1 to 24 hours under an inert atmosphere, to give compound (I'). Alternatively compound (I') can be prepared by reaction of the amine (V) with compound (VI) by heating at elevated temperature, such as 50° C.-140° C., in a suitable solvent such as DMF, NMP or 1,4-dioxan for about 1-48 hours with a base such as potassium carbonate, sodium hydrogen carbonate or Hünig's base.

Preferred conditions are:

1-2.5 eq. halide (VI), 1-2 eq. potassium carbonate in N,N-dimethylformamide at 50-95° C. for 4-18 hours; or 1-2.5 eq. halide (VI), 2-3 eq. Hünig's base, in 1,4-dioxan or NMP at reflux for 18-48 hours; or 1 eq. halide (VI), 3.5 eq. NaOt-Bu, 0.08 eq BINAP, 0.4 eq. Pd(dba)₂, in toluene for 8 hours at 70° C.

Alkylation (R¹=Substituted Alkyl), Z'=Halo, Preferably Br or Cl

Alkylation of compound (V) can be performed by reaction with a suitable alkylating agent, R¹Z' in the presence of a suitable tertiary amine (NMM, Et₃N or Hünig's base) or alkali metal base (K₂CO₃, Cs₂CO₃) in a suitable solvent (MeCN, DMF), at about room temperature.

The preferred conditions are:

amine (V) R¹Z', excess K₂CO₃ or Hünig's base in DMF for 18 hours at room temperature.

Alternatively, compounds (I') may be prepared by the route shown below in Scheme 1.3.

Scheme 1.3

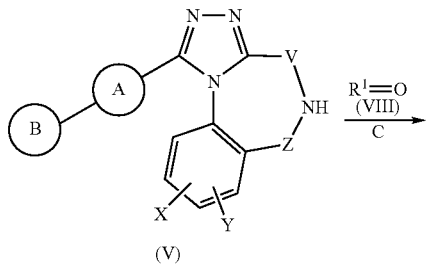

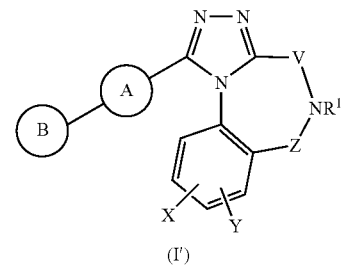

Compounds suitable for use as compound (VII) are commercially available or are known in the literature.

Step (c): Amine (V) is reacted with an excess of aldehyde/ketone (VII) in the presence of a reducing agent, such as sodium triacetoxyborohydride or sodium cyanoborohydride, to give the compound of formula (I'). This reaction may be carried out by:

stirring the starting materials at temperatures such as 20° C.-80° C. for 1 to 48 hours in a suitable solvent such as dichloromethane, or heating amine (V) with excess compound (VII) with a suitable Lewis acid catalyst such as titanium tetrachloride or titanium tetraisopropoxide at temperatures such as 50° C.-100° C. in a suitable solvent such as dichloroethane or ethanol for 1-18 hours, followed by reduction of the intermediate imine/iminium species with a suitable reducing agent, such as sodium borohydride, or hydrogenolysis over a suitable catalyst, such as platinum oxide or palladium on carbon.

Preferred conditions are:

amine (V), 1-1.5 eq. aldehyde/ketone (VII), 1-2.0 eq. sodium triacetoxy borohydride in dichloromethane, optionally in the presence of AcOH at room temperature for 2 hours.

When ring B is linked to ring A via an N atom, and W represents O or S then:

Scheme 2.1

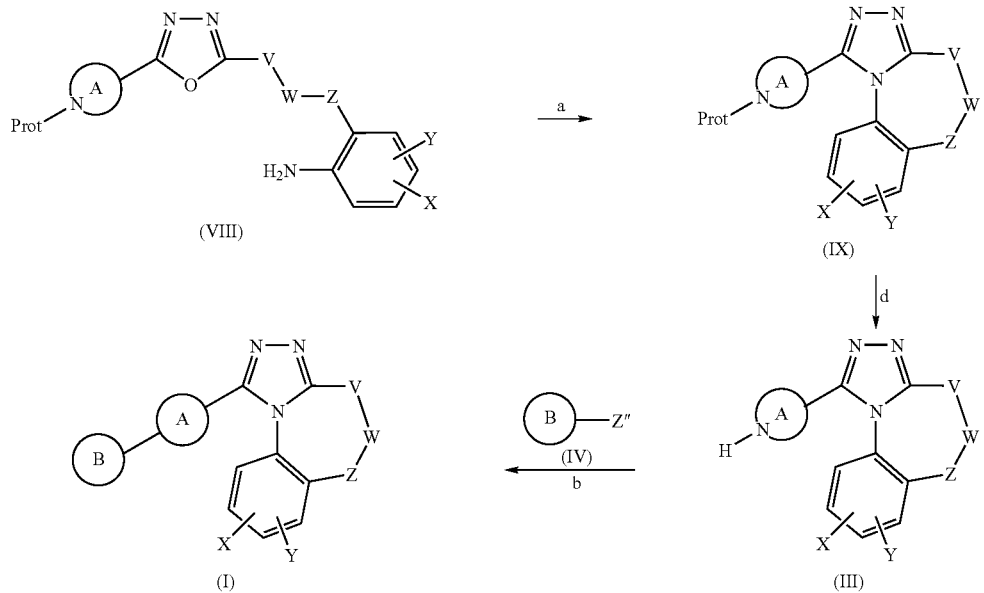

Prot represents a suitable protecting group for nitrogen, for example Boc, CBz or Allyl carbamate. Standard methodology for nitrogen protecting groups is used, such as that found in textbooks (e.g. "Protecting Groups in Organic Synthesis" by T. W. Greene and P. Wutz). Z" represents a leaving group such as halogen.

Compounds suitable for use as compound (IV) are commercially available or are known in the literature.

Arylation of compound (III) can be carried out as described in Step (b) above.

Preferred conditions are:
1-2.5 eq. halide (IV), 1-2 eq. potassium carbonate in N,N-dimethylformamide at 50° C. for 4-18 hours; or
1-2.5 eq. halide (IV), 2-3 eq. Hünig's base, in 1,4-dioxan or NMP at reflux for 18-48 hours; or
1 eq. halide (IV), 3.5 eq. NaOt-Bu, 0.08 eq BINAP, 0.4 eq. Pd(dba)$_2$, in toluene for 8 hours at 70° C.

Step (d): Deprotection of compound (IX) is undertaken using standard methodology, as described in "Protecting Groups in Organic Synthesis" by T. W. Greene and P. Wutz".

When Prot is Boc, the preferred methods are:
hydrogen chloride in a suitable solvent such as 1,4-dioxane at room temperature for 1-16 hours; or
a solution of trifluoroacetic acid in dichloromethane for 1-2 hours.

When Prot is CBz, the preferred method is hydrogenolysis using a suitable palladium catalyst in a solvent such as ethanol.

When Prot is an allyl carbamate, preferred conditions are thiobenzoic acid and a suitable palladium catalyst such as Pd$_2$(Dba)$_3$ with a suitable phosphine additive such as 1,4-bis(diphenylphosphino)butane in tetrahydrofuran for 20 minutes.

When ring B is linked to ring A via an N atom, and W represents NR$^1$ then:

Scheme 2.2

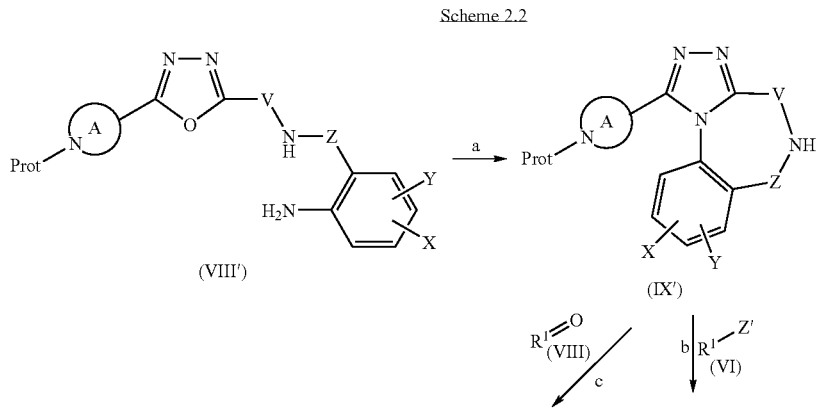

-continued

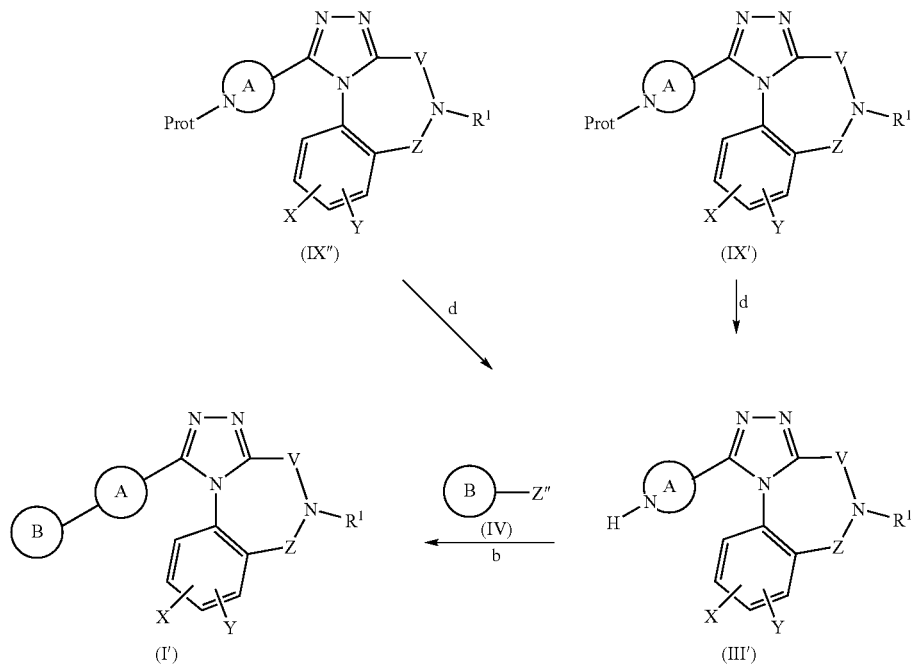

Prot represents a suitable protecting group for nitrogen, for example Boc, CBz or Allyl carbamate. Standard methodology for nitrogen protecting groups is used, such as that found in textbooks, (e.g., "Protecting Groups in Organic Synthesis" by T. W. Greene and P. Wutz).

Z' represents a leaving group (typically Cl or OH). Z" represents halo (typically Cl).

Compounds suitable for uses as compound (IV) are commercially available or are known in the literature.

Compound (IX") typically can be prepared from Compound (IX') using the methodology described in Step (b) and Step (c) above.

Compound (III') typically can be prepared from compound (IX") using the methodology described in Step (d) above.

Compounds (I') typically can be prepared by arylation of compounds (III') using the methodology described in Step (b) above.

Compounds suitable for use as compounds (II) and (VIII) are known in the literature or can be prepared as shown in Schemes 3.1, 3.2 and 3.3 below.

-continued

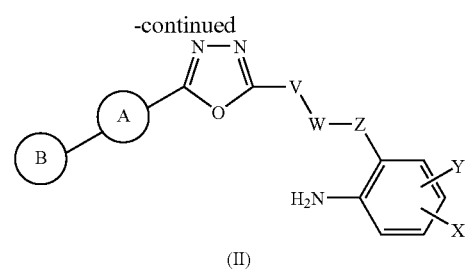

LG represents a leaving group, typically halo, and preferably chloro or bromo.

When rings A and B are linked through an N atom then:

Scheme 3.1

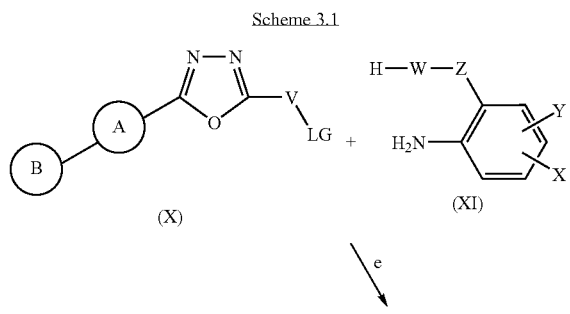

Scheme 3.2

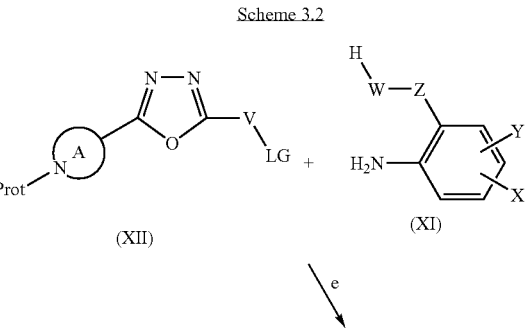

-continued

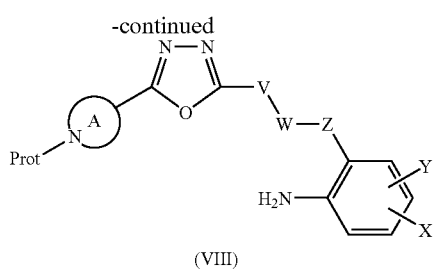

(VIII)

LG is a leaving group, typically halo, and preferably chloro or bromo.

Compounds suitable for use as compounds (XI) are known in the literature or can be prepared using standard methodology: for example, reduction of benzoic acids (see preparation 7 below) or benzonitriles (see preparation 10 below) or nitrobenzenes (preparations 57 and 58).

When W represents $NR^1$:

Step (e): Compound (X)/(XII) is reacted with an excess of compound (XI) to give compound (II)/(VIII) respectively, optionally in the presence of an excess of base, such as triethylamine, Hünig's base or NMM or potassium carbonate as proton acceptor, optionally in the presence of a catalyst (e.g. NaI) in a suitable high boiling solvent such as THF, Toluene or DMF at temperatures from 50° C. to 100° C. for 1 to 48 hours.

Preferred conditions are:

2.5 eq. of compound (XI) in THF at 50° C. for 48 hours; or 1.1 eq compound (XI) 1.1 eq NMM or $K_2CO_3$, 0.5 eq. NaI in THF at 50° C.

When W represents O or S:

Step (e): Compound (X)/(XII) is reacted with an excess of compound (XI) in the presence of a base such as sodium hydride, potassium hexamethyldisilazide, "butyl lithium or isopropyl magnesium chloride, in a suitable solvent such as THF, Toluene or NMP at temperatures from 0° C. to 50° C. for 1 to 24 hours, to give compound (II)/(VIII) respectively.

Preferred conditions are:

1.1-3 eq. of compound (XI) and 1.1-2.5 eq. of NaH in THF at 20° C. for 2 hours.

When $W=NR^1$, and $Z=CO$ then

Scheme 3.3

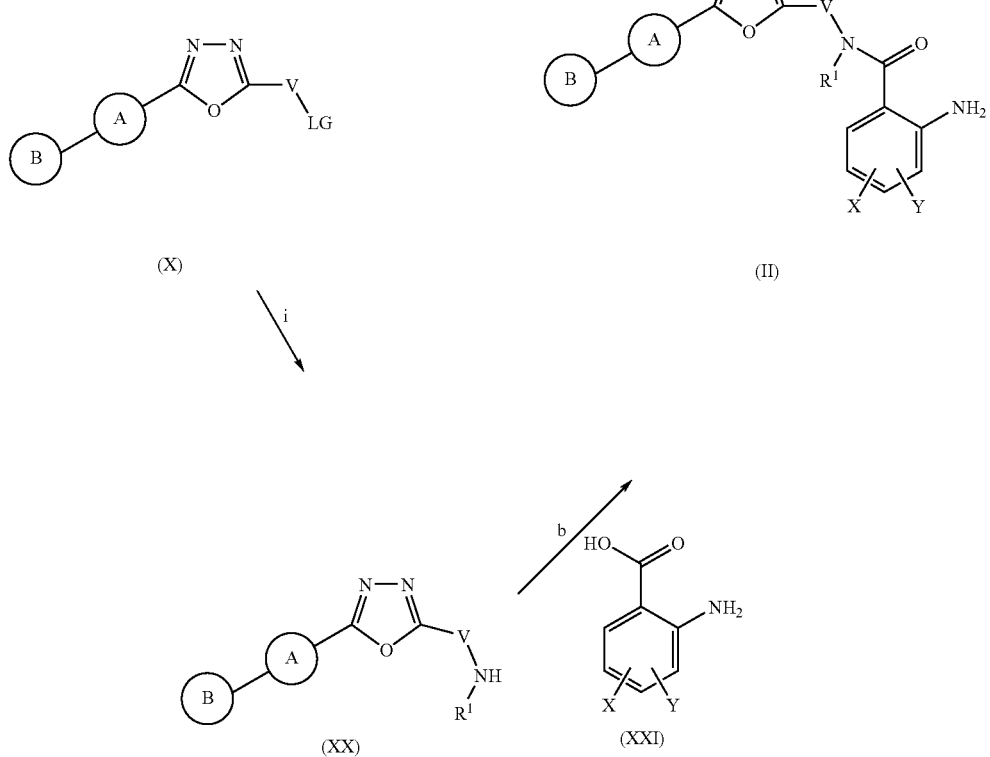

Step (i): Amine (XX) may be prepared by amination of compound (X) with the amine R¹NH₂ in a solvent such as ethanol or tetrahydrofuran at 25-75° C. for 5-72 hours.

Preferred conditions are:

Compound (X), excess of R¹NH₂ in ethanol and THF at room temperature for about 72 hours.

Compound (II) may be prepared by coupling of the amine (XX) with the acid (XXI) according to the procedure described previously in step (b).

Compounds suitable for use as compounds (X) and (XII) are known in the literature or can be prepared as shown in Schemes 4.1 and 4.2.

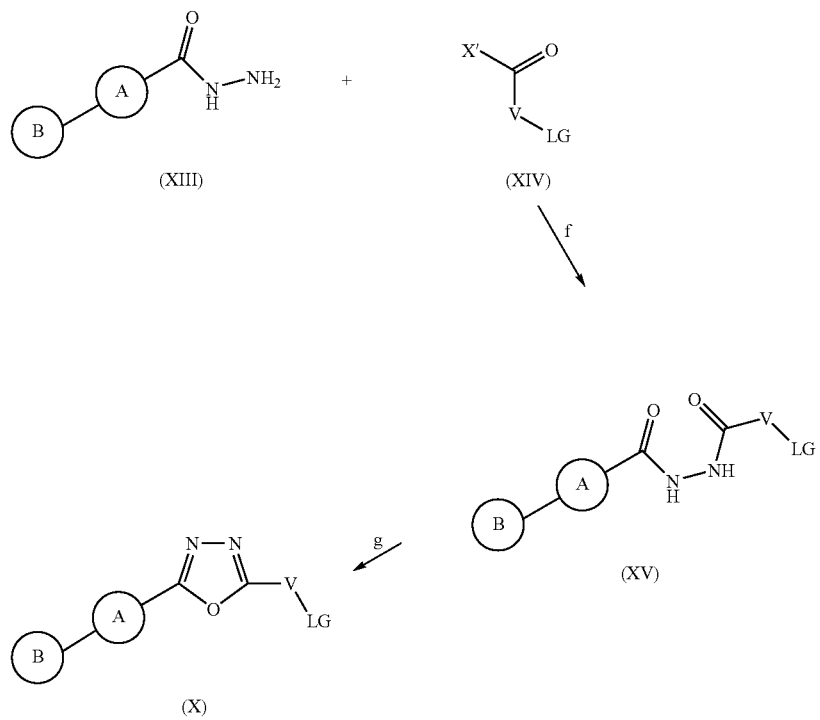

Scheme 4.1

X' represents OH or halo, and preferably represents Cl. LG represents a leaving group, typically halo, and preferably chloro or bromo When rings A and B are linked through an N atom then:

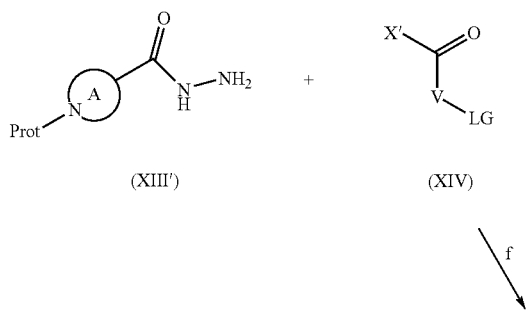

Scheme 4.2

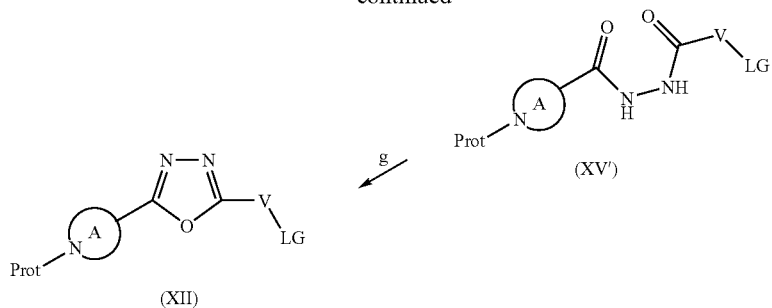

X' represents OH or halo, and preferably represents Cl. LG is a leaving group, typically halo, and preferably chloro or bromo Compound (XIV) is either commercially available or is known in the literature.

Step (f): The reaction of hydrazide (XIII/XIII') with compound (XIV) can be carried out by standard methods.

Coupling may be undertaken by using either:
(i) an acyl chloride (XIV)+hydrazide (XIII/XIII') with an excess of acid acceptor in a suitable solvent; or
(ii) acid (XIV) with a conventional coupling agent+hydrazide (XIII/XIII'), optionally in the presence of a catalyst, with an excess of acid acceptor in a suitable solvent.

Typically the conditions are as follows:
(i) acid chloride (XIV) (generated in-situ), an excess of hydrazide (XIII/XIII') optionally with an excess of 3° amine such as Et$_3$N, Hünig's base or NMM, in DCM or THF, without heating for 1 to 24 hours; or
(ii) acid (XIV), WSCDI/DCC and HOBT/HOAT, an excess of hydrazide (XIII/XIII'), with an excess of NMM, Et$_3$N, Hünig's base in THF, DCM or EtOAc, at room temperature for 4 to 48 hours; or
(ii) acid (XIV), PYBOP®/PyBrOP®/Mukaiyama's reagent, an excess of hydrazide (XIII/XIII'), with an excess of NMM, Et$_3$N, Hünig's base in THF, DCM or EtOAc, at room temperature for 4 to 24 hours.

The preferred conditions are:
Hydrazide (XIII/XIII'), 1.5 eq. chloro acetyl chloride (XIV), 1.5 eq. NMM in DCM at room temperature for 16 hours.

Step (g): Cyclisation of compound (XV/XV') is carried out under suitable dehydrating conditions, at elevated temperatures for up to 18 hours.

Typically, dehydrating agents such as polyphosphoric acid, phosphorous oxychloride, triflic anhydride are used at temperatures from 20 to 120° C. for 5 minutes to 12 hours. Optionally, the reaction can be carried out in the presence of a base such as pyridine and suitable solvents such as dichloromethane and acetonitrile. Alternatively, the oxadiazole (XII/X) may be prepared according to the method of Rigo et. al. Synth. Commun. 16(13), 1665, 1986.

Preferred conditions are:
phosphorous oxychloride at 100° C. for 8 hours, or 2.5 eq. triflic anhydride in acetonitrile at 20° C. for 5 hours.

Compounds suitable for use as compounds (XIII/XIII') are known in the literature or can be prepared as shown in Schemes 5.1 and 5.2.

Scheme 5.1

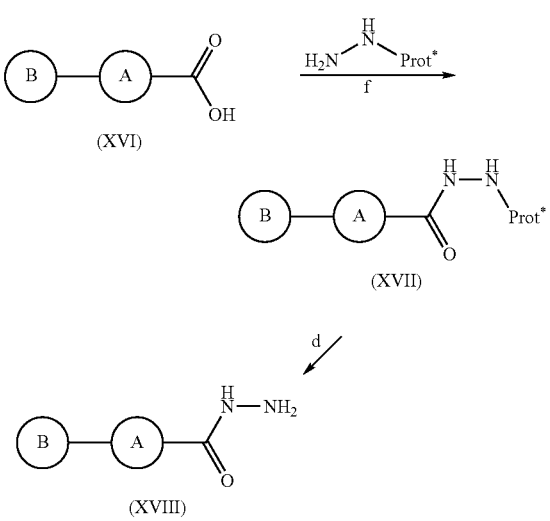

When rings A and B are linked through an N atom then:

Scheme 5.2

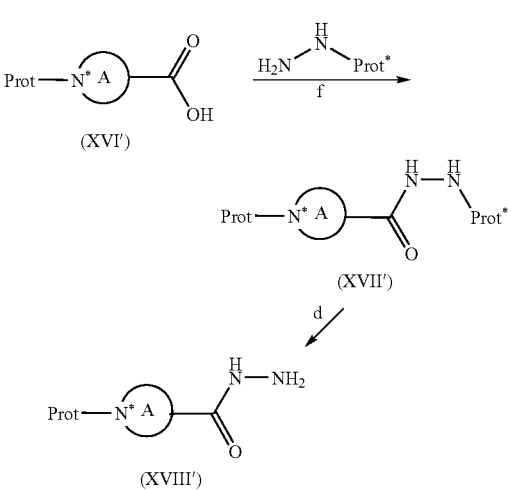

Compounds (XVI)/(XVI') and protected hydrazine are either commercially available or are known in standard methodology such as the hydrolysis of the corresponding ester.

Carboxylic acid (XVI)/(XVI') and protected hydrazine, where prot* is typically Boc, may be coupled to give compound (XVII/XVII') respectively, using the conditions described above for the preparation of (XV/XV'), and then prot* is removed using standard methodology as described in Step (d) as described above, to give (XIII/XIII').

Alternative routes to compound (XIII/XIII') are shown below in Schemes 6.1 and 6.2:

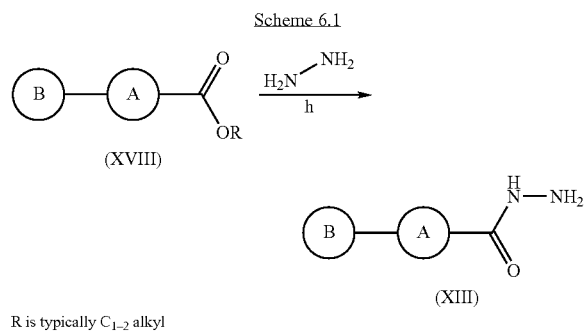

Scheme 6.1

R is typically $C_{1-2}$ alkyl

When rings A and B are linked through an N atom then:

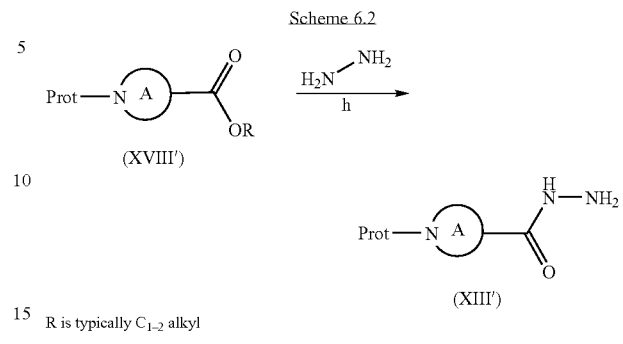

Scheme 6.2

R is typically $C_{1-2}$ alkyl

Step (h): The ester (XVIII/XVIII') may be reacted with hydrazine in a suitable solvent, such as methanol, at an elevated temperature to provide the hydrazide (XVII/XVII').

Preferred conditions:

3 eq. hydrazine, in methanol, at reflux for 18 hours.

Alternatively, compounds of formula (I) may be prepared according to the Scheme 7.0 below.

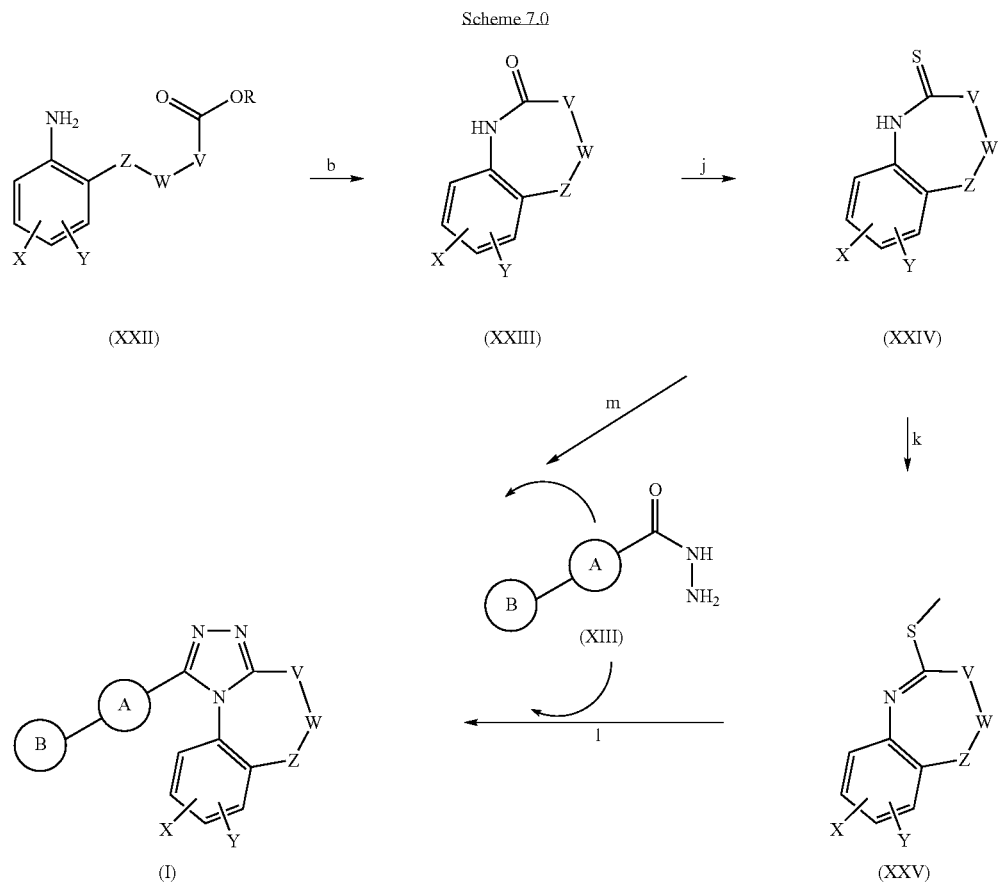

Scheme 7.0

(I)
R = H or $C_{1-4}$ alkyl, typically tert-butyl, methyl or ethyl

When R=H,

Compounds of formula (XXIII) may be prepared by an intra-molecular coupling of the amino acid (XXII), according to the procedure previously described in step (b).

Preferably, compound (XXII) is treated with 1.4 eq. HBTU, 4.5 eq. NMM in DCM at room temperature for about 18 hours.

When R=$C_1$-$C_4$ alkyl:

Compounds of formula (XXIII) may be prepared by base catalysed cyclisation of the amino ester (XXII) typically carried out at room temperature or below for 1-5 hours.

Typically, bases such as potassium tert-butoxide, sodium ethoxide or isopropyl magnesium chloride are used at or below 20° C. in a suitable solvent such as tetrahydrofuran or ethanol for 1-5 hours.

Preferably, compound (XXII) is treated with 1.1 eq. potassium ter-butoxide in THF at 20° C. for about 2 hours.

Step (j): Formation of Thioamide

Thionation of the amide (XXIII) using a suitable thionating agent (e.g. Lawesson's reagent, $P_4S_{10}$), and optionally in the presence of a base (e.g. $Na_2CO_3$) in a suitable solvent (e.g. THF) at between 0° C. and room temperature.

Preferred conditions are:

1 eq. $P_4S_{10}$, 1 eq. $Na_2CO_3$, 1 eq. amide (XXIII) in THF at between 3-25° C. for 18-72 hours Step (k): Thioimidate Formation Treatment of the thioamide (XXIV) with a strong base such as KO $^t$Bu or LDA, in a suitable solvent such as THF or ether, followed by quench of the anion formed by a suitable methyl source (e.g. MeI, Me p-tosylate) provides the thioimidate (XXV).

Preferred conditions are:

1 eq. thioamide (XXIV), treated with 1 eq. KO $^t$Bu, 1 eq. Me p-tosyalte in THF.

Triazole Formation:

Step (l): The thioimidate (XXV) is treated with the hydrazide (XIII) in a suitable solvent, typically ethanol at elevated temperature to provide the compound of formula (I), optionally in the presence of an acid catalysed such as TFA, p-TSA.

Preferred conditions are:

1 eq. thioimidate (XXV), 1 eq. hydrazide (XIII), in ethanol at reflux for 2 hours.

Step (m): The thioamide (XXIV) is treated with the hydrazide (XIII) in a suitable solvent, typically n-Butan-1-ol at elevated temperature to provide the compound of formula (I), optionally in the presence of an acid catalysed such as TFA, p-TSA.

Preferred conditions are:

1 eq. Thioamide (XXIV), 1 eq. hydrazide (XIII), in n-butan-1-ol at reflux for 18 hours.

Compounds suitable for use as compounds (XXII) are known in the literature or can be prepared using standard methodology, for example see C. Apfel et al., J. Med. Chem. 44(12), 1847-1852, 2001, C. P. Lang et. al., WO2002008228, F. Ishikawa, J. Med. Chem. 28(10), 1387-93, 1985 or Uskokovic, M. et. al., Journal of Organic Chemistry (1965), 30(9), 3111-14.

It will be apparent to those skilled in the art that sensitive functional groups may need to be protected and deprotected during synthesis of a compound of formula (I). This may be achieved by conventional techniques, for example as described in "Protective Groups in Organic Synthesis" by T W Greene and P G M Wuts, John Wiley and Sons Inc, 1991, exemplified by examples 42-49 and 55-58.

Certain compounds of formula (I) may be converted to alternative compounds of formula (I) using standard chemical transformations. Examples of these are illustrated below:

Amination (e.g. Examples 40 & 41)

When $R^1$ contains a leaving group, such as a chloro substituent, this may react with a suitable amine $HNR^2R^3$ in the presence of a suitable tertiary amine base ($Et_3N$, NMM or Hünig's base) or alkali metal base ($K_2CO_3$, $Cs_2CO_3$) in a suitable solvent (e.g. DMF, MeCN), optionally at elevated temperature. Preferably, the chloro compound is treated with an excess of $HNR^2R^3$, in the presence of an excess of $K_2CO_3$ in DMF at 70° C.

Reduction (e.g. Examples 50-54, 64 & 65)

Compounds containing a carbonyl function may be reduced using a suitable reducing agent such as DIBAL or borane in a suitable solvent such as ether or THF at or between room temperature and the reflux temperature of the reaction. Preferably, the amide compound is treated with 10 eq. borane in THF at reflux, followed by an excess of HCl at reflux.

Reductive Amination (e.g. Examples 69-81 & 84-90)

Compounds of formula (I) containing a reactive N atom may react with an aldehyde or ketone, according to the methods described in step (c). Preferably, the amine of formula (I) is treated with an excess of aldehyde/ketone and 2 eq. $Na(OAc)_3BH$ in DCM, optionally in the presence of an excess of $Et_3N$ and acetic acid, at room temperature for up to 18 hours.

Oxidation (e.g. when W=S)

Compounds of formula (I) containing a Sulphur atom may be oxidised using a suitable oxidising agent such as hydrogen peroxide or meta-chloro perbenzoic acid in a suitable solvent such as trifluoroacetic acid or 1,1,1,3,3,3-Hexafluoro-propan-2-ol between 0-25° C.

When oxidising to sulphoxide (W=$S(O)_1$), preferably the sulphide of formula (I) is treated with 1-1.2 eq. of 30% aqueous hydrogen peroxide in 1,1,1,3,3,3-Hexafluoro-propan-2-ol at room temperature for up to 1 hour.

When oxidising to sulphone (W=$S(O)_2$), preferably the sulphide of formula (I) is treated with 2-3 eq. of 30% aqueous hydrogen peroxide in trifluoroacetic acid for up to 1 hour.

(Alternatively, the sulphoxide (W=$S(O)_1$) above may be oxidised to the sulphone (W=$S(O)_2$) using 1-2 eq. of 30% aqueous hydrogen peroxide in trifluoroacetic acid for up to 1 hour.)

In accordance with the present invention there is further provided an intermediate of formula (II):

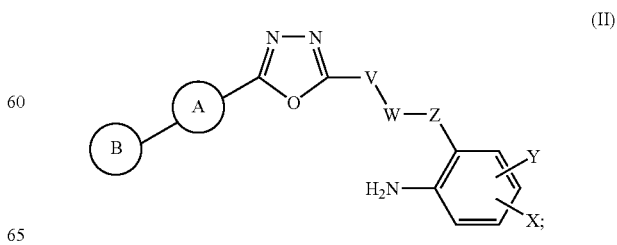

an intermediate of formula (III):

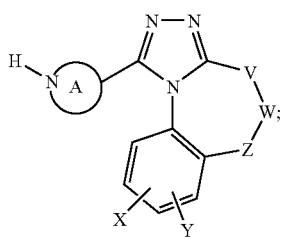

(III)

an intermediate of formula (X):

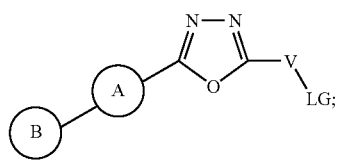

(X)

an intermediate of formula (XV):

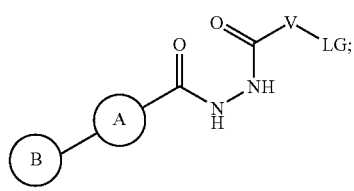

(XV)

an intermediate of formula (XXIV):

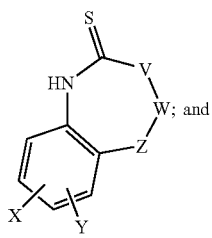

(XXIV)

an intermediate of formula (XXV):

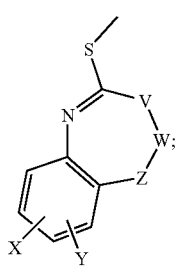

(XXV)

wherein V, W, X, Y, Z, rings A and B, LG and n are as defined above.

The compounds of the present invention are useful because they possess pharmacological activity in animals. In particular they are useful in the treatment of a number of conditions including aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis.sleep disorder, spinal cord injury, thrombosis, urogenital tract infection, urolithiasis. Particularly of interest is dysmenorrhoea (primary or secondary), more particularly, primary dysmenorrhoea.

Thus, according to another aspect of the invention, there is provided a method of treatment of dysmenorrhoea which comprises administering a therapeutically effective amount of a compound of the invention to a patient suffering from anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease. The use of the compounds as a medicament and the use of the compounds of the present invention in the manufacture of a medicament for the treatment of anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease, particularly dysmenorrhoea, are also provided.

Compounds of the invention intended for pharmaceutical use may be administered as crystalline or amorphous products. They may be obtained, for example, as solid plugs, powders, or films by methods such as precipitation, crystallisation, freeze drying, spray drying, or evaporative drying. Microwave or radio frequency drying may be used for this purpose.

They may be administered alone or in combination with one or more other compounds of the invention or in combination with one or more other drugs (or as any combination thereof). For example, the compounds of the present invention may be administered in combination with an oral contraceptive. Alternatively, they may be administered in combination with a PDE5 inhibitor. They may also be administered in combination with an NO donor. Alternatively, they may be administered in combination with L-arginine, or as an arginate salt. The compounds of the present invention may also be used in combination with a COX inhibitor.

Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19$^{th}$ Edition (Mack Publishing Company, 1995).

Thus, according to another aspect of the present invention, there is provided a pharmaceutical formulation comprising a compound of formula (I) in admixture with a pharmaceutically acceptable adjuvant, diluent or carrier.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example water, ethanol, polyethylene glycol, propylene glycol, methylcellulose, or a suitable oil, and one or more emulsifying agents and/or suspending agents. Liquid formulations may also be prepared by the reconstitution of a solid, for example from a sachet.

The compounds of the invention may also be used in fast-dissolving, fast disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt %, of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % and 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt %, of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted- and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intreperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled-, targeted- and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958 by Finnin and Morgan (October 1999).

Other means of topical administration include delivery by iontophoresis, electroporation, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane.

For intranasal use, the powder may comprise a bioadhesive agent, for example, chitosan or cyclodextrin.

The pressurised container, pump, spray, atomizer or nebuliser contains a solution or suspension of the compound(s) of the invention comprising, for example, ethanol, aqueous ethanol, or a suitable alternative agent for dispersing, solubilising or extending release of the active, the propellant(s) as solvent and an optional surfactant, such as sorbitan trioleate, oleic acid, or an oligolactic acid.

Prior to use in a dry powder of suspension formulation, the drug product is micronised to a size suitable for delivery by inhalation (typically less than 5 microns). This may be achieved by any appropriate comminuting method, such a spiral jet milling, fluid bed jet milling, supercritical fluid processing to form nanoparticles, high pressure homogenisation or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as /-leucine, mannitol, or magnesium stearate. The lactose may be anhydrous or in the form of the monohydrate, preferably the latter. other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly-DL-lactic-coglycolic acid (PGLA). Modified release formulations include delayed-, sustained-, pulsed-, controlled-, targeted and programmed release.

The compounds of the invention may be administered rectally or vaginally, for example, in the form of a suppository, pessary or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities such as cyclodextrin or polyethylene glycol-containing polymers to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compounds of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention will typically be in the range of from about 0.01 to about 15 mg/kg of body weight, depending on the mode of administration. The total daily dose may be administered in a single dose or divided doses throughout the day. These dosages are based on an average human subject having a weight of about 65 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with primary and/or secondary dysmenorrhoea. The treatment may be a pre-treatment as well as a treatment at the on-set of symptoms.

The compounds of the present invention may be tested in the screens set out below:

1.0 $V_{1A}$ Filter Binding Assay 1.1 Membrane Preparation

Receptor binding assays were performed on cellular membranes prepared from CHO cells stably expressing the human $V_{1A}$ receptor, (CHO-h$V_{1A}$). The CHO-h$V_{1A}$ cell line was kindly provided under a licensing agreement by Marc Thibonnier, Dept. of Medicine, Case Western Reserve University School of Medicine, Cleveland, Ohio. CHO-h$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 μg/ml G418. For bulk production of cell pellets, adherent CHO-h$V_{1A}$ cells were grown to confluency of 90-100% in 850 cm² roller bottles containing a medium of DMEM/Hams F12 Nutrient Mix supplemented with 10% fetal bovine serum, 2 mM L-glutamine and 15 mM HEPES. Confluent CHO-h$V_{1A}$ cells were washed with phosphate-buffered saline (PBS), harvested into ice cold PBS and centrifuged at 1,000 rpm. Cell pellets were stored at −80° C. until use. Cell pellets were thawed on ice and homogenised in membrane preparation buffer consisting of 50 mM Tris-HCl, pH 7.4, 5 mM $MgCl_2$ and supplemented with a protease inhibitor cocktail, (Roche). The cell homogenate was centrifuged at 1000 rpm, 10 min, 4° C. and the supernatant was removed and stored on ice. The remaining pellet was homogenised and centrifuged as before. The supernatants were pooled and centrifuged at 25,000×g for 30 min at 4° C. The pellet was resuspended in freezing buffer consisting of 50 mM Tris-HCl, pH 7.4, 5 mM $MgCl_2$ and 20% glycerol and stored in small aliquots at −80° C. until use. Protein concentration was determined using Bradford reagent and BSA as a standard.

1.2 $V_{1A}$ Filter Binding

Protein linearity followed by saturation binding studies were performed on each new batch of membrane. Membrane concentration was chosen that gave specific binding on the linear portion of the curve. Saturation binding studies were then performed using various concentrations of [$^3$H]-arginine vasopressin, [$^3$H]-AVP (0.05 nM-100 nM) and the $K_d$ and $B_{max}$ determined.

Compounds were tested for their effects on [$^3$H]-AVP binding to CHO-h$V_{1A}$ membranes, ($^3$H-AVP; specific activity 65.5 Ci/mmol; NEN Life Sciences). Compounds were solubilised in dimethylsulfoxide (DMSO) and diluted to working concentration of 10% DMSO with assay buffer containing 50 mM Tris-HCL pH 7.4, 5 mM $MgCl_2$ and 0.05% BSA. 25 μl compound and 25 μl [$^3$H]-AVP, (final concentration at or below $K_d$ determined for membrane batch, typically 0.5 nM-0.6 nM) were added to a 96-well round bottom polypropylene plate. The binding reaction was initiated by the addition of 200 μl membrane and the plates were gently shaken for 60 min at room temperature. The reaction was terminated by rapid filtration using a Filtermate Cell Harvester (Packard Instruments) through a 96-well GF/B UniFilter Plate which had been presoaked in 0.5% polyethyleneimine to prevent peptide sticking. The filters were washed three times with 1 ml ice cold wash buffer containing 50 mM Tris-HCL pH 7.4 and 5 mM $MgCl_2$. The plates were dried and 50 μl Microscint-0 (Packard instruments) was added to each well. The plates were sealed and counted on a TopCount Microplate Scintillation Counter (Packard Instruments). Non-specific binding (NSB) was determined using 1 μM unlabelled d(CH2)5Tyr(Me)AVP ([β-mercapto-β,β-cyclopentamethylenepropionyl,0-Me-Tyr$^2$,Arg$^8$]-vasopressin) (βMCPVP), (Sigma). The radioligand binding data was analysed using a four parameter logistic equation with the min forced to 0%. The slope was free fitted and fell between −0.75 and −1.25 for valid curves. Specific binding was calculated by subtracting the mean NSB cpm from the mean Total cpm. For test compounds the amount of ligand bound to the receptor was expressed as % bound=(sample cpm−mean NSB cpm)/specific binding cpm×100. The % bound was plotted against the concentration of test compound and a sigmoidal curve was fitted. The inhibitory dissociation constant ($K_i$) was calculated using the Cheng-Prusoff equation: $K_i=IC_{50}/(1+[L]/K_d)$ where [L] is the concentration of ligand present in the well and $K_d$ is the dissociation constant of the radioligand obtained from Scatchard plot analysis.

2.0 $V_{1A}$ Functional Assay; Inhibition of AVP/$V_{1A}$-R Mediated $Ca^{2+}$ Mobilization by FLIPR (Fluorescent Imaging Plate Reader) (Molecular Devices)

Intracellular calcium release was measured in CHO-h$V_{1A}$ cells using FLIPR, which allows the rapid detection of calcium following receptor activation. The CHO-h$V_{1A}$ cell line was kindly provided under a licensing agreement by Marc Thibonnier, Dept. of Medicine, Case Western Reserve University School of Medicine, Cleveland, Ohio. CHO-$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 μg/ml G418. On the afternoon before the assay cells were plated at a density of 20,000 cells per well into black sterile 96-well plates with clear bottoms to allow cell inspection and fluorescence measurements from the bottom of each well. Wash buffer containing Dulbecco's phosphate buffered saline (DPBS) and 2.5 mM probenecid and loading dye consisting of cell culture medium containing 4 μM Fluo-3-AM (dissolved in DMSO and pluronic acid), (Molecular Probes) and 2.5 mM probenecid was prepared fresh on the day of assay. Compounds were solubilised in DMSO and diluted in assay buffer consisting of DPBS containing 1% DMSO, 0.1% BSA and 2.5 mM probenecid. The cells were incubated with 100 μl loading dye per well for 1 hour at 37° C. in humidified atmosphere with 5% $CO_2$. After dye loading the cells were washed three times in 100 μl wash buffer using a Denley plate washer. 100 μl wash buffer was left in each well. Intracellular fluorescence was measured using FLIPR. Fluorescence readings were obtained at 2 s intervals with 50 μl of the test compound added after 30 s. An additional 155 measurements at 2 s intervals were then taken to detect any compound agonistic activity. 50 μl of arginine vasopressin (AVP) was then added so that the final assay volume was 200 μl. Further fluorescence readings were collected at 1 s intervals for 120 s. Responses were measured as peak fluorescence intensity (FI). For pharmacological characterization a basal FI was subtracted from each fluorescence response. For AVP dose response curves, each response was expressed as a % of the response to the highest concentration of AVP in that row. For $IC_{50}$ determinations, each response was expressed as a % of the response to AVP. IC50 values were converted to a modified $K_b$ value using the Cheng-Prusoff equation which takes into account the agonist concentration, [A], the agonist $EC_{50}$ and the slope: $K_b = IC_{50}/(2+[A]/A_{50})^n)^{1/n} - 1$ where [A] is the concentration of AVP, $A_{50}$ is the $EC_{50}$ of AVP from the dose response curve and n=slope of the AVP dose response curve.

The compounds of the invention may have the advantage that they are more potent, have a longer duration of action, have a broader range of activity, are more stable, have fewer side effects or are more selective, or have other more useful properties than the compounds of the prior art.

Thus the invention provides:

(i) a compound of formula (I) or a pharmaceutically acceptable derivative thereof;

(ii) a process for the preparation of a compound of formula (I) or a pharmaceutically acceptable derivative thereof;

(iii) a pharmaceutical formulation including a compound of formula (I) or a pharmaceutically acceptable derivative thereof, together with a pharmaceutically acceptable excipients, diluent or carrier;

(iv) a compound of formula (I) or a pharmaceutically acceptable derivative or composition thereof, for use as a medicament;

(v) the use of a compound of formula (I) or of a pharmaceutically acceptable derivative or composition thereof, for the manufacture of a medicament for the treatment of aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preeclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis;

(vi) use as in (v) where the disease or disorder is anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease;

(vii) use as in (v) where the disease or disorder is dysmenorrhoea (primary and secondary);

(viii) a method of treatment of a mammal to treat aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis including treating said mammal with an effective amount of a compound of formula (I) or with a pharmaceutically acceptable derivative or composition thereof;

(ix) a method as in (vii) where the disease or disorder is anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease;

(x) a method as in (vii) where the disease or disorder is dysmenorrhoea (primary and secondary);

(xi) intermediates of the formulae (II), (III), (X), (XV), (XXIV), and (XXV);

(xii) use of a combination of a compound of formula (I) with an oral contraceptive for treating dysmenorrhoea (primary and/or secondary);

(xiii) use of a combination of a compound of formula (I) with a PDE5 inhibitor for treating dysmenorrhoea (primary and/or secondary);

(xiv) use of a combination of a compound of formula (I) with an NO donor for treating dysmenorrhoea (primary and/or secondary);

(xv) use of a combination of a compound of formula (I) with L-arginine for treating dysmenorrhoea (primary and/or secondary);

(xvi) use of a combination of a compound of formula (I) with a COX inhibitor for treating dysmenorrhoea (primary and/or secondary).

The invention is illustrated by the following preparations and examples:

Preparation 1: 3,4,5,6-Tetrahydro-2H-[1,2']bipyridinyl-4-carboxylic acid hydrazide

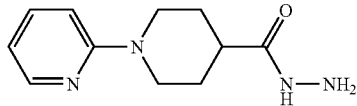

3,4,5,6-Tetrahydro-2H-[1,2']bipyridinyl-4-carboxylic acid ethyl ester (1 g, 4.3 mmol)(see reference Farmaco, 1993, 48(10), 1439) was dissolved in methanol (20 ml) containing hydrazine hydrate (620 μl, 20 mmol) and was heated under reflux for 18 hours. The mixture was cooled to room temperature and evaporated under reduced pressure. The solid formed was triturated with propan-2-ol to give the title compound as a white solid (493 mg).

APCI MS m/z 221 [M+H]$^+$

Preparation 1b: 3,4,5,6-Tetrahydro-2H-[1,2']bipyridinyl-4-carboxylic acid ethyl ester

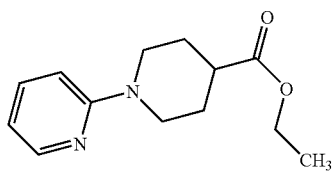

Potassium carbonate (52.5 g, 0.379 mol) was charged to a stirred solution of 2-Bromopyridine (60 g, 0.379 mol) and Ethylisonipecotate (59.7 g, 0.379 mol), at an ambient temperature before heating to 120° C. for 24 hours. The mixture was cooled to room temperature and propan-2-ol charged to the solution. The reaction mixture was then filtered and telescoped into preparation 1c.

Preparation 1c: 3,4,5,6-Tetrahydro-2H-[1,2']bipyridinyl-4-carboxylic acid hydrazide

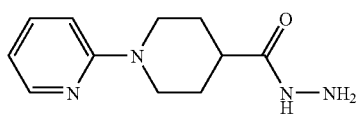

Hydrazine hydrate (61.4 ml, 1.265 mol) was charged to a propan-2-ol solution of 3,4,5,6-Tetrahydro-2H-[1,2']bipyridinyl-4-carboxylic acid ethyl ester (0.253 mol, 5 ml/g)(see reference Farmaco, 1993, 48(10), 1439), before heating under reflux for 18 hours. The mixture was cooled to room temperature and then to 10° C. and the product, a white solid, was collected by filtration (44.5 g).

APCI MS m/z 221 [M+H]$^+$

Preparation 2: 1-Pyrimidin-2-yl-piperidine-4-carboxylic acid hydrazide

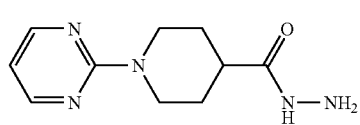

The title compound was obtained from 1-Pyrimidin-2-yl-piperidine-4-carboxylic acid ethyl ester (see Farmaco, 1993, 48(10), 1439) in 91% yield following the procedure described in preparation 1.

APCI MS m/z 222 [M+H]$^+$

Preparation 3: 3,4,5,6-Tetrahydro-2H-[1,2']bipyridinyl-4-carboxylic acid N'-(2-chloro-acetyl)-hydrazide

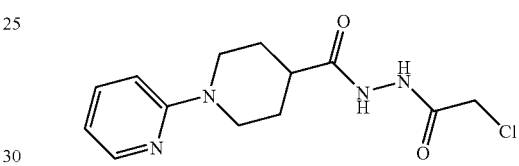

The hydrazide of Preparation 1 (23.6 g, 0.11 mol) was suspended in dichloromethane (500 ml) and 4-methylmorpholine (17.7 ml, 0.16 mol) was added. The mixture was cooled using an ice bath and chloroacetyl chloride (12.8 ml, 0.16 mol) was added dropwise. The reaction was warmed to room temperature and was stirred for 3 hours. The solid formed was isolated by filtration, washed with dichloromethane and diethyl ether, and dried under vacuum to give the title compound (20.4 g).

LCMS: m/z ES$^+$ 297 [M+H]$^+$

Preparation 3b: 3,4,5,6-Tetrahydro-2H-[1,2']bipyridinyl-4-carboxylic acid N'-(2-chloro-acetyl)-hydrazide

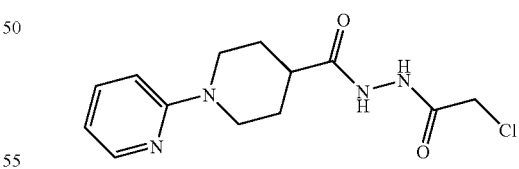

The hydrazide of Preparation 1c (5.0 g, 23 mmol) was suspended in dichloromethane (100 ml) and 4-methylmorpholine (3.75 ml, 34 mmol) was added. The mixture was cooled using an ice bath and chloroacetyl chloride (1.9 ml, 24 mmol) was added dropwise. The reaction was warmed to room temperature and was stirred for 3 hours. The solid formed was isolated by filtration, washed with dichloromethane, and dried under vacuum to give the title compound (2.2 g).

LCMS: m/z ES$^+$ 297 [M+H]$^+$

Preparation 4: 1-Pyrimidin-2-yl-piperidine-4-carboxylic acid N'-(2-chloro-acetyl)-hydrazide

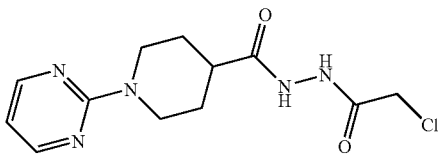

The title compound was prepared from the hydrazide of preparation 2 and chloroacetyl chloride, in 96% yield, using the procedure described in preparation 3.

APCI MS m/z 298 [M+H]$^+$

Preparation 5: 4-(5-Chloromethyl-[1,3,4]oxadiazol-2-yl)-3,4,5,6-tetrahydro-2H-[1,2']bipyridinyl

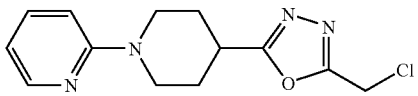

The hydrazide of Preparation 3 (20.4 g, 69 mmol) was suspended in phosphorus oxychloride (150 ml) at 100° C. for 4 hours. The mixture was cooled and the solvent was evaporated under reduced pressure. The residue was dissolved in ethyl acetate and was added to water. The aqueous layer was basified by addition of solid sodium hydrogen carbonate and the phases were separated. The aqueous phase was extracted with ethyl acetate (×2) and the combined organic layers were dried over magnesium sulphate and evaporated under reduced pressure. The material isolated was triturated with diethyl ether to give the title compound as a beige solid (15 g).

$^1$H NMR (400 MHz, CD$_3$OD): δ 1.91 (m, 2H), 2.19 (m, 2H), 3.14 (m, 2H), 3.30 (m, 1H), 4.29 (m, 2H), 4.86 (s, 2H), 6.69 (m, 1H), 6.89 (d, 1H), 7.58 (m, 1H), 8.08 (d, 1H)

Preparation 5b: 4-(5-Chloromethyl-[1,3,4]oxadiazol-2-yl)-3,4,5,6-tetrahydro-2H-[1,2']bipyridinyl

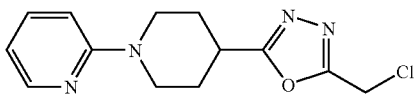

The hydrazide of Preparation 3 (50.0 g, 169 mmol) was suspended in acetonitrile (250 ml) and cooled using an ice bath. Trifluoromethanesulfonic anhydride (29.9 ml, 177 mmol) was added dropwise at T<15° C. The reaction was warmed to room temperature and stirred for 16 hours. The reaction was cooled using an ice bath and a solution of sodium hydrogen carbonate (29.8 g, 354 mmol) in water (250 ml) was added dropwise. Dichloromethane (250 ml) was added and the phases were separated. The organic containing product phase was used in preparation 14b.

$^1$H NMR (400 MHz, CD$_3$OD): δ 1.91 (m, 2H), 2.19 (m, 2H), 3.14 (m, 2H), 3.30 (m, 1H), 4.29 (m, 2H), 4.86 (s, 2H), 6.69 (m, 1H), 6.89 (d, 1H), 7.58 (m, 1H), 8.08 (d, 1H)

Preparation 6: 2-[4-(5-Chloromethyl-[1,3,4]oxadiazol-2-yl)-piperidin-1-yl]-pyrimidine

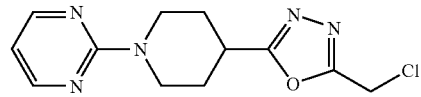

The title compound was prepared from the hydrazide of preparation 4, in 84% yield, using the procedure described in preparation 5.

APCI MS m/z 280 [M+H]$^{+1}$H NMR (400 MHz, CDCl$_3$): δ 1.91 (m, 2H), 2.19 (m, 2H), 3.14 (m, 3H), 4.65 (s, 2H), 4.86 (m, 2H), 6.49 (m, 1H), 6.89 (d, 1H), 8.35 (d, 1H)

Preparation 7: (2-Amino-5-methoxy-phenyl)-methanol

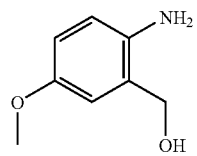

2-Amino-5-methoxy-benzoic acid (2.0 g, 12 mmol) in tetrahydrofuran (20 ml) was added dropwise to an ice cooled 1 molar solution of lithium aluminium hydride (14.4 ml) in tetrahydrofuran and stirred at 5° C. for 2 hours. Water (0.5 ml) was added dropwise, followed by 2 molar aqueous sodium hydroxide solution (0.5 ml). The resulting emulsion was dried over magnesium sulphate, then filtered and evaporated under reduced pressure to give the title compound as a yellow solid (766 mg).

APCI MS m/z 154 [M+H]$^{+1}$H NMR (400 MHz, CD$_3$OD): δ 3.70 (s, 3H), 4.55 (s, 2H), 6.65-6.78 (m, 3H)

Preparation 8: (2-Amino-6-chloro-phenyl)-methanol

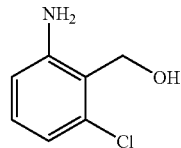

The title compound was prepared from 2-Amino-6-chloro-benzoic acid, in 69% yield as an off-white solid, following the procedure described in preparation 7.

APCI MS m/z 158 [M+H]$^{+1}$H NMR (400 MHz, CDCl$_3$): δ 4.85 (s, 2H), 6.60 (d, 1H), 6.80 (d, 1H), 7.00 (t, 1H)

Preparation 9: (2-Amino-4-chloro-phenyl)-methanol

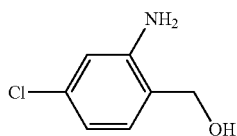

The title compound was prepared from 2-Amino-4-chloro-benzoic acid, in 48% yield as an off-white solid, following the procedure described in preparation 7.

APCI MS m/z 170 [MNa]$^{+1}$H NMR (400 MHz, CD$_3$OD): δ 4.55 (s, 2H), 6.60 (d, 1H), 6.70 (d, 1H), 7.00 (d, 1H)

Preparation 10: 2-Aminomethyl-4-chloro-phenylamine

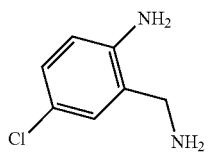

2-Amino-5-chloro-benzonitrile (9.0 g, 59 mmol) in tetrahydrofuran (100 ml) was added dropwise to an ice cooled 1 molar solution of lithium aluminium hydride (100 ml) in tetrahydrofuran and the reaction mixture was stirred at room temperature for 18 hours. Water (10 ml) was added dropwise. The resulting emulsion was dried over magnesium sulphate, filtered and evaporated under reduced pressure to give the title compound as a white solid (4.56 g).

$^1$H NMR (400 MHz, CDCl$_3$): δ 3.85 (s, 2H), 4.50 (s, 2H), 6.60 (d, 1H), 7.05 (m, 2H)

Preparation 11: Acetic acid 2-(2-acetylamino-5-chloro-phenyl)-ethyl ester

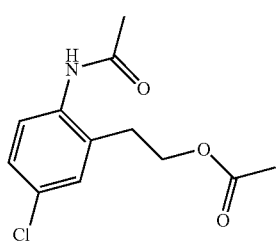

A solution of chlorine in glacial acetic acid (0.98M, 30 ml) was added dropwise to a solution of N-[2-(2-Hydroxy-ethyl)-phenyl]-acetamide (5.0 g, 27.9 mmol)(see reference Biochemistry 1979, 18(5), 860) in glacial acetic acid (50 ml) and the mixture was stirred at room temperature for 20 hours. The glacial acetic acid was removed under reduced pressure. The resulting oil was triturated with diethyl ether to give the title compound (3.3 g) as a pale yellow solid after filtration.

APCI MS m/z 256, [MH]$^+$, 278 [MNa]$^{+1}$H NMR (400 MHz, CDCl$_3$): δ 2.13 (s, 3H), 2.26 (s, 3H), 2.87 (t, 2H), 4.13 (t, 2H), 7.11 (d, 1H), 7.23 (dd, 1H), 8.05 (d, 1H), 8.27 (s, 1H).

Preparation 12: 2-(2-Amino-5-chloro-phenyl)-ethanol

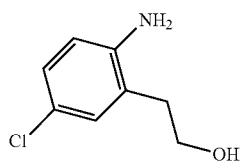

The compound from preparation 11 was suspended in 2 molar aqueous hydrochloric acid (20 ml) and heated to 100° C. for 4 hours. The solution was allowed to cool, made basic (pH 9) with 0.880 aqueous ammonia and partitioned with ethyl acetate (50 ml). The organic layer was washed with water and saturated brine, and dried over magnesium sulphate. The solution was filtered and then evaporated under reduced pressure. The residue was purified by chromatography on silica gel using methanol and ammonium hydroxide in dichloromethane as eluant (5:0.5:95) to give the title compound as a brown oil (0.43 g).

APCI MS m/z 172, [MH]$^{+1}$H NMR (400 MHz, CD$_3$OD): δ 2.64 (t, 2H), 3.69(t, 2H), 6.61 (d, 1H), 6.87 (dd, 1H), 6.93 (d, 1H).

Preparation 13: 2-({[5-(3,4,5,6-Tetrahydro-2H-[1,2']bipyridinyl-4-yl)-[1,3,4]oxadiazol-2-ylmethyl]-amino}-methyl)-phenylamine

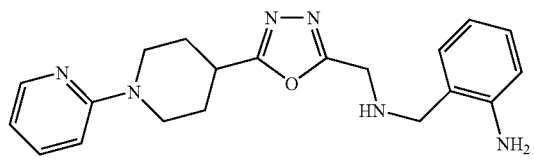

A solution of 2-Aminomethyl-phenylamine (2.2 g, 17.9 mmol) in tetrahydrofuran (50 ml) was added to a solution of the oxadiazole of preparation 5 (2.0 g, 7.18 mmol) in tetrahydrofuran (50 ml) and the mixture was heated to 50° C. for 18 hours. The reaction mixture was evaporated under reduced pressure and the residue was purified by chromatography on silica gel using methanol and ammonium hydroxide in dichloromethane as eluant (5:0.5:95), to give the title compound as a pale yellow gum (2.6 g).

APCI MS m/z 365 [MH]$^+$, 387 [MNa]$^{+1}$H NMR (400 MHz, CDCl$_3$): δ 1.94 (m, 2H), 2.18(m, 2H), 3.14 (m, 3H), 3.88(s, 2H), 4.00 (s, 2H), 4.31 (m, 2H), 6.60-6.75 (m, 4H), 7.02 (d, 1H), 7.12 (t, 1H), 7.48 (t, 1H), 8.20 (d, 1H).

Preparation 14: 4-Chloro-2-({[5-(3,4,5,6-tetrahydro-2H-[1,2']bipyridinyl-4-yl)-[1,3,4]oxadiazol-2-ylmethyl]-amino}-methyl)-phenylamine

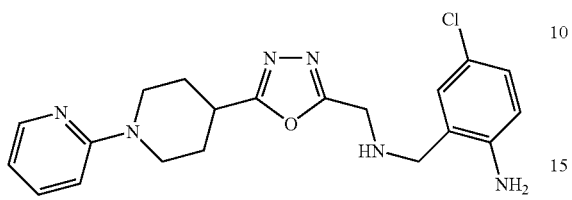

A solution of the amine of preparation 10 (6.4 g, 41 mmol) in tetrahydrofuran (50 ml) was added to a solution of the oxadiazole of preparation 5 (4.56 g, 16 mmol) in tetrahydrofuran (50 ml) and the mixture was heated to 50° C. for 18 hours. The reaction mixture was evaporated under reduced pressure and the residue was purified by chromatography on silica gel using methanol in dichloromethane as eluant (5:95), to give the title compound as a white solid (4.65 g).

APCI MS m/z 399 [MH]$^{+1}$H NMR (400 MHz, CDCl$_3$): δ 1.95 (m, 2H), 2.20(m, 2H), 3.10 (m, 2H), 3.20 (m, 1H), 3.80(s, 2H), 4.00 (s, 2H), 4.30 (m, 2H), 6.60 (m, 1H), 6.65 (t, 1H), 6.70 (d, 1H), 7.00 (s, 1H), 7.05 (d, 1H), 7.50 (t, 1H), 8.20 (d, 1H)

Preparation 14b: 4-Chloro-2-({[5-(3,4,5,6-tetrahydro-2H-[1,2']bipyridinyl-4-yl)-[1,3,4]oxadiazol-2-ylmethyl]-amino}-methyl)-phenylamine

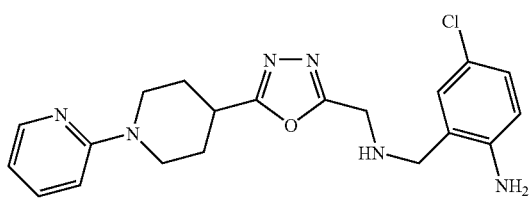

The acetonitrile/dichloromethane solution of the oxadiazole from preparation 5b was distilled, the residue placed in acetonitrile, and then heated at reflux with sodium hydrogen carbonate (14.9 g, 177 mmol) and the amine from preparation 10 (39.7 g, 253 mmol) for 5 hours. The mixture was cooled and water (250 ml) and dichloromethane (1500 ml) was added. The phases were separated and the organic phase distilled and replaced with ethyl acetate. The resulting precipitate was isolated by filtration to afford the title compound as a yellow solid (32.8 g)

APCI MS m/z 280 [M+H]$^{+1}$H NMR (400 MHz, CDCl$_3$): δ 1.91 (m, 2H), 2.19 (m, 2H), 3.14 (m, 3H), 4.65 (s, 2H), 4.86 (m, 2H), 6.49 (m, 1H), 6.89 (d, 1H), 8.35 (d, 1H)

Preparation 15: 4-Chloro-2-({[5-(1-pyrimidin-2-yl-piperidin-4-yl)-[1,3,4]oxadiazol-2-ylmethyl]-amino}-methyl)-phenylamine

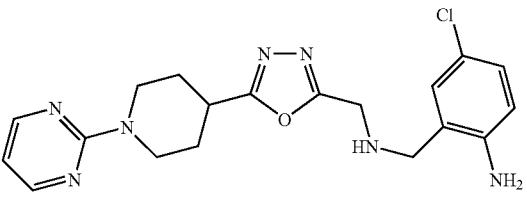

A solution of the amine of preparation 10 (4.12 g, 26 mmol) in tetrahydrofuran (50 ml) was added to a solution of the oxadiazole of preparation 6 (2.95 g, 11 mmol) in tetrahydrofuran (50 ml) and heated to 50° C. for 18 hours. The reaction mixture was evaporated under reduced pressure and the residue purified by chromatography on silica gel using ethyl acetate as eluant to give the title compound as an off-white solid (2.34 g).

APCI MS m/z 400 [MH]$^{+1}$H NMR (400 MHz, CDCl$_3$): δ 1.80 (m, 2H), 2.20 (m, 2H), 3.20 (m, 3H), 3.80 (s, 2H), 4.00 (s, 2H), 4.75 (m, 2H), 6.50 (t, 1H), 6.60 (d, 1H), 7.00 (d, 1H), 7.05 (d, 1H), 8.35 (d, 2H).

Preparation 16: 2-[5-(3,4,5,6-Tetrahydro-2H-[1,2']bipyridinyl-4-yl)-[1,3,4]oxadiazol-2-ylmethoxymethyl]-phenylamine A solution of (2-Amino-phenyl)-methanol (996 mg, 8 mmol) in tetrahydrofuran (5 ml) was added dropwise to an ice cooled suspension of sodium hydride (60% in mineral oil, 324 mg, 8.1 mmol) in tetrahydrofuran (5 ml) and stirred for 0.5 hour. A solution of the oxadiazole of preparation 5 (750 mg, 2.69 mmol) in tetrahydrofuran (5 ml) was added dropwise and the mixture stirred at room temperature for 3 hours. Ethyl acetate (50 ml) was added and the solution was extracted with water (25 ml). The aqueous solution was washed with ethyl acetate (2×20 ml). The combined organic layers were dried over magnesium sulphate and evaporated under reduced pressure. The residue was purified by chromatography on silica gel using a gradient of ethyl acetate in pentane as eluant (2:1 to 100:0) to give the title compound (300 mg) as a white solid.

APCI MS m/z 366 [MH]$^{+1}$H NMR (400 MHz, CDCl$_3$): δ 1.90 (m, 2H), 2.20 (m, 2H), 3.10 (m, 2H), 3.20 (m, 1H), 4.20 (s, 2H), 4.35 (m, 2H), 4.64 (s, 2H), 4.66 (s, 2H), 6.65 (m, 4H), 7.05 (d, 1H), 7.15 (t, 1H), 7.50 (t, 1H), 8.20 (d, 1H).

Preparation 17: 3-Chloro-2-[5-(3,4,5,6-tetrahydro-2H-[1,2']bipyridinyl-4-yl)-[1,3,4]oxadiazol-2-yl-methoxymethyl]-phenylamine

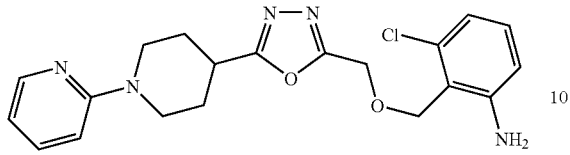

The title compound was prepared from the alcohol of preparation 8 and the oxadiazole of preparation 5, in 55% yield, using the procedure described in preparation 16.

APCI MS m/z 400 [MH]$^{+1}$H NMR (400 MHz, CDCl$_3$): δ 1.95 (m, 2H), 2.20 (m, 2H), 3.05 (m, 2H), 3.20 (m, 1H), 4.30 (m, 2H), 4.40 (s, 2H), 4.70 (s, 2H), 4.90 (s, 2H), 6.55 (d, 1H), 6.60 (m, 1H), 6.70 (d, 1H), 6.75 (d, 1H), 7.00 (t, 1H), 7.15 (t, 1H), 7.45 (t, 1H), 8.20 (d, 1H).

Preparation 18: 5-Chloro-2-[5-(3,4,5,6-tetrahydro-2H-[1,2']bipyridinyl-4-yl)-[1,3,4]oxadiazol-2-yl-methoxymethyl]-phenylamine

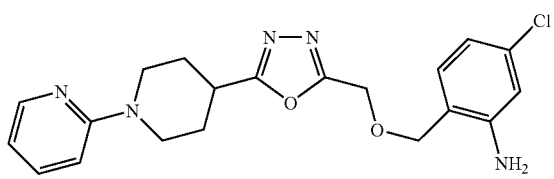

The title compound was prepared from the alcohol of preparation 9 and the oxadiazole of preparation 5, in 42% yield, using the procedure described in preparation 16.

APCI MS m/z 400 [MH]$^+$, 422 [MNa]$^{+1}$H NMR (400 MHz, CDCl$_3$): δ 1.90 (m, 2H), 2.20 (m, 2H), 3.10 (m, 3H), 4.30 (m, 4H), 4.60 (s, 2H), 4.65 (s, 2H), 6.75 (m, 4H), 7.00 (d, 1H), 7.45 (t, 1H), 8.20 (d, 1H).

Preparation 19: 4-Methoxy-2-[5-(3,4,5,6-tetrahydro-2H-[1,2']bipyridinyl-4-yl)-[1,3,4]oxadiazol-2-yl-methoxymethyl]-phenylamine

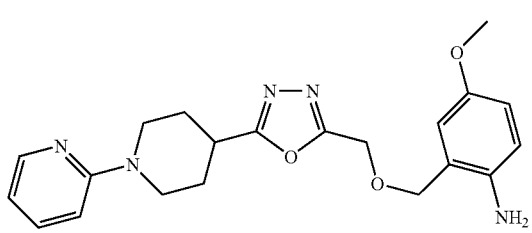

The title compound was prepared from the alcohol of preparation 7 and the oxadiazole of preparation 5, in 53% yield, using the procedure described in preparation 16.

APCI MS m/z 396 [MH]$^+$, 418 [MNa]$^{+1}$H NMR (400 MHz, CDCl$_3$): δ 1.95 (m, 2H), 2.20 (m, 2H), 3.10 (m, 3H), 3.75 (s, 3H), 4.60 (s, 2H), 4.65 (s, 2H), 6.70 (m, 5H), 7.45 (t, 1H), 8.20 (d, 1H).

Preparation 20: 4-Chloro-2-[5-(3,4,5,6-tetrahydro-2H-[1,2']bipyridinyl-4-yl)-[1,3,4]oxadiazol-2-yl-methoxymethyl]-phenylamine

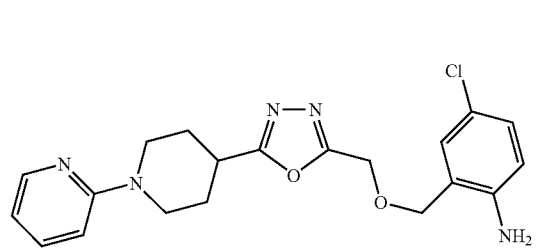

The title compound was prepared from (2-Amino-5-chloro-phenyl)-methanol and the oxadiazole of preparation 5, in 61% yield, using the procedure described in preparation 16.

APCI MS m/z 400 [MH]$^{+1}$H NMR (400 MHz, CDCl$_3$): δ 1.95 (m, 2H), 2.20 (m, 2H), 3.10 (m, 2H), 3.20 (m, 1H), 4.20 (s, 2H), 4.35 (m, 2H), 4.60 (s, 2H), 4.70 (s, 2H), 6.60 (m, 2H), 6.70 (d, 1H), 7.10 (m, 2H), 7.45 (t, 1H), 8.20 (d, 1H).

Preparation 21: 2-{2-[5-(3,4,5,6-Tetrahydro-2H-[1,2']bipyridinyl-4-yl)-[1,3,4]oxadiazol-2-ylmethoxy]-ethyl}-phenylamine

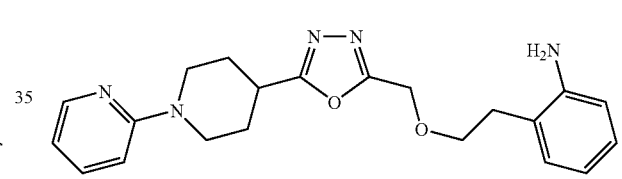

The title compound was prepared from 2-(2-Amino-phenyl)-ethanol and the oxadiazole of preparation 5, in 66% yield, using the procedure described in preparation 16.

APCI MS m/z 380 [MH]$^{+1}$H NMR (400 MHz, CDCl$_3$): δ 1.95 (m, 2H), 2.15 (m, 2H), 2.80 (t, 2H), 3.10 (m, 3H), 3.80 (m, 4H), 4.30 (m, 2H), 4.65 (s, 2H), 6.70 (m, 4H), 7.00 (m, 2H), 7.50 (t, 1H), 8.20 (d, 1H).

Preparation 22: 4-Chloro-2-{2-[5-(3,4,5,6-tetrahydro-2H-[1,2']bipyridinyl-4-yl)-[1,3,4]oxadiazol-2-ylmethoxy]-ethyl}-phenylamine

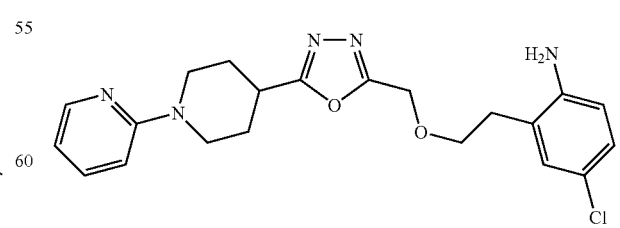

The title compound was prepared from the alcohol of preparation 12 and the oxadiazole of preparation 5, in 52% yield, using the procedure described in preparation 16.

APCI MS m/z 414 [MH]+ 1H NMR (400 MHz, CDCl3): δ 1.92 (m, 2H), 2.15 (m, 2H), 2.77 (t, 2H), 3.10 (m, 3H), 3.79 (t, 2H), 4.28 (m, 2H), 4.66 (s, 2H), 6.58 (d, 1H), 6.62 (d, 1H), 6.71 (d, 1H), 6.97 (m, 2H), 7.49 (t, 1H), 8.20 (d, 1H).

Preparation 23: 4-Chloro-2-[5-(1-pyrimidin-2-yl-piperidin-4-yl)-[1,3,4]oxadiazol-2-ylmethoxymethyl]-phenylamine

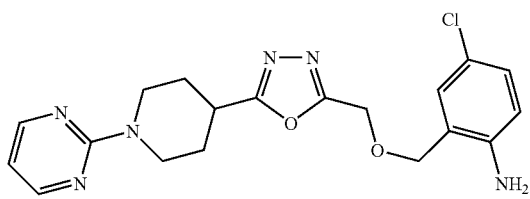

A solution of (2-Amino-5-chloro-phenyl)-methanol (850 mg, 5.4 mmol) in tetrahydrofuran (10 ml) was added dropwise to an ice cooled suspension of sodium hydride (60% in mineral oil, 215 mg, 5.4 mmol) in tetrahydrofuran (5 ml) and stirred for 1 hour. A solution of the oxadiazole of preparation 6 (500 mg, 1.79 mmol) in tetrahydrofuran (5 ml) was added dropwise and the mixture stirred at room temperature for 1 hour. Dichloromethane (50 ml) was added and the solution was extracted with water (25 ml). The aqueous solution was washed with dichloromethane (2×20 ml). The combined organic layers were dried over magnesium sulphate and evaporated under reduced pressure. The residue was purified by chromatography on silica gel using diethyl ether followed by ethyl acetate as eluant to give, after trituration with diethyl ether, the title compound (320 mg) as a white solid.

APCI MS m/z 401 [MH]+ 1H NMR (400 MHz, CDCl3): δ 1.92 (m, 2H), 2.19 (m, 2H), 3.24 (m, 3H), 4.60 (s, 2H), 4.68 (s, 2H), 4.75 (m, 2H), 6.57 (m, 1H), 6.63 (d, 1H), 7.08 (m, 2H), 8.37 (d, 2H).

Preparation 24: 2-{2-[5-(1-Pyrimidin-2-yl-piperidin-4-yl)-[1,3,4]oxadiazol-2-ylmethoxy]-ethyl}-phenylamine

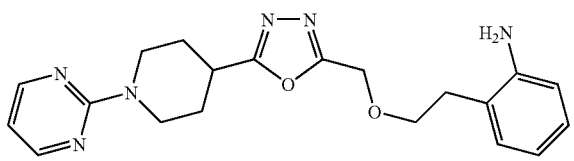

The title compound was prepared from 2-(2-Amino-phenyl)-ethanol and the oxadiazole of preparation 6, in 54% yield, using the procedure described in preparation 23.

APCI MS m/z 381 [MH]+ 1H NMR (400 MHz, CDCl3): δ 1.85 (m, 2H), 2.15 (m, 2H), 2.88 (m, 2H), 3.18 (m, 3H), 1H), 3.80 (t, 2H), 4.68 (s, 2H), 4.74 (m, 2H), 6.51 (m, 1H), 6.80 (m, 2H), 7.08 (m, 2H), 8.37 (d, 2H).

Preparation 25: 4-[N'-(2-Chloro-acetyl)-hydrazinocarbonyl]-piperidine-1-carboxylic acid tert-butyl ester

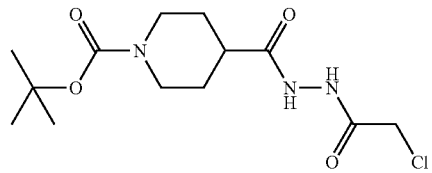

4-Hydrazinocarbonyl-piperidine-1-carboxylic acid tert-butyl ester (see reference WO 9703986 A1 19970206) (25 g, 103 mmol) was dissolved in dichloromethane (300 ml) and 4-methylmorpholine (12.5 ml, 113 mmol) was added. The mixture was cooled using an ice bath and chloroacetyl chloride (8.2 ml, 103 mmol) was added dropwise. The reaction was warmed to room temperature and was stirred for 4 hours. The reaction mixture was partitioned with aqueous sodium hydrogen carbonate solution, dried over magnesium sulphate, filtered and the filtrate evaporated to give the title compound as an off-white solid (29.6 g).

APCI MS m/z 318 [M–H]+ Found; C, 48.01; H, 6.91; N, 12.85; $C_{13}H_{22}N_3O_4Cl$ 0.3H$_2$O requires; C, 48.02; H, 7.01; N, 12.92%.

Preparation 26: 4-(5-Chloromethyl-[1,3,4]oxadiazol-2-yl)-piperidine-1-carboxylic acid tert-butyl ester

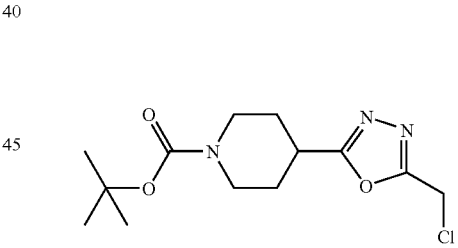

The hydrazide of preparation 25 (5.0 g, 15.6 mmol) was suspended in dichloromethane (200 ml) and pyridine (6.4 ml, 78 mmol) added before cooling the mixture to 10° C. Trifluoroacetic anhydride (6.6 ml, 39 mmol) was added dropwise over 15 minutes and then stirred at room temperature for 3 hours. The reaction mixture was partitioned with water (50 ml) and the organic layer dried over magnesium sulphate. The mixture was filtered and the filtrate evaporated under reduced pressure. The residue was purified by chromatography on silica gel using methanol in dichloromethane as eluant (2:98) to give the title compound as a white solid (2.95 g).

1H NMR (400 MHz, CD3OD): δ 1.45 (s, 9H), 1.74 (m, 2H), 2.19 (m, 2H), 3.04 (m, 2H), 3.24 (m, 1H), 4.09 (m, 2H), 4.85 (s, 2H)

Preparation 27: 4-[5-(2-Amino-5-chloro-benzyloxymethyl)-[1,3,4]oxadiazol-2-yl]-piperidine-1-carboxylic acid tert-butyl ester

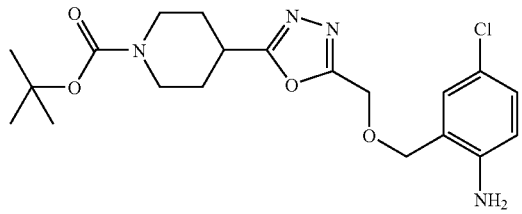

A solution of (2-Amino-5-chloro-phenyl)-methanol (1 g, 6.4 mmol) in tetrahydrofuran (10 ml) was added dropwise to an ice cooled suspension of sodium hydride (60% in mineral oil, 215 mg, 5.4 mmol) in tetrahydrofuran (5 ml) and stirred for 1 hour. A solution of the oxadiazole of preparation 26 (1 g, 5.3 mmol) in tetrahydrofuran (5 ml) was added dropwise and the mixture stirred at room temperature for 2 hours. The reaction mixture was partitioned between dichloromethane (50 ml) and sodium hydrogen carbonate solution (25 ml). The aqueous solution was washed with dichloromethane (2×20 ml). The combined organic layers were dried over magnesium sulphate and evaporated under reduced pressure. The residue was purified by chromatography on silica gel using methanol in dichloromethane (5:95) as eluant to give the title compound (1.3 g) as a yellow solid.

APCI MS m/z 423 [MH]$^+$, 323 [M-Boc]$^{+1}$H NMR (400 MHz, CDCl$_3$): δ 1.47 (s, 9H), 1.81 (m, 2H), 2.07 (m, 2H), 2.96 (m, 2H), 3.08 (m, 1H), 4.12 (m, 2H), 4.23 (s, 2H), 4.58 (s, 2H), 4.68 (s, 2H), 6.62 (d, 1H), 7.07 (s, 1H), 7.12 (d, 1H).

Preparation 28: 4-(8-Chloro-4H,6H-5-oxa-2,3,10b-triaza-benzo[e]azulen-1-yl)-piperidine-1-carboxylic acid tert-butyl ester

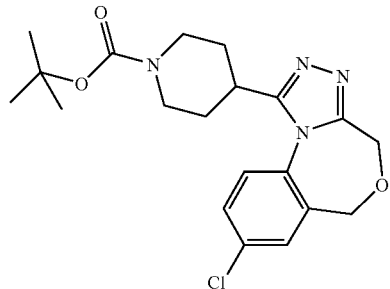

Toluene-4-sulfonic acid (80 mg, 0.46 mmol) was added to a solution of the oxadiazole of preparation 27 (1.28 g, 3.0 mmol) in xylene and heated to 140° C. for 18 hours. The xylene was removed under reduced pressure. The residue was partitioned between dichloromethane (100 ml) and sodium hydrogen carbonate solution (25 ml). The aqueous solution was washed with dichloromethane (2×20 ml). The combined organic layers were dried over magnesium sulphate and evaporated under reduced pressure. The residue was purified by chromatography on silica gel using methanol and ammonium hydroxide in dichloromethane (5:0.5:95) as eluant to give the title compound (730 mg) as a pale yellow foam.

APCI MS m/z 405 [MH]$^+$, 305 [M-Boc]$^{+1}$H NMR (400 MHz, CDCl$_3$): δ 1.43 (s, 9H), 1.85 (m, 2H), 1.96 (m, 2H), 2.92 (m, 2H), 3.08 (m, 1H), 4.18 (m, 2H), 4.40 (s, 2H), 4.66 (s, 2H), 7.36 (d, 1H), 7.58 (m, 2H). Found; C, 57.98; H, 6.17; N, 13.40; C$_{20}$H$_{25}$N$_4$O$_3$Cl 0.5H$_2$O requires; C, 58.04; H, 6.33; N, 13.54%.

Preparation 29: 8-Chloro-1-piperidin-4-yl-4H,6H-5-oxa-2,3,10b-triaza-benzo[e]azulene

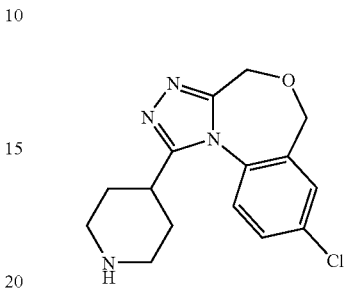

The triazole of preparation 28 (700 mg, 1.73 mmol) was dissolved in 1,4-dioxan (6 ml) and hydrochloric acid (4M in 1,4-dioxane, 12 ml) added. The reaction mixture was stirred at room temperature for 4 hours. The 1,4-dioxane was removed under reduced pressure.

The residue was partitioned between dichloromethane (100 ml) and sodium hydrogen carbonate solution (25 ml). The aqueous solution was washed with dichloromethane (2×20 ml). The combined organic layers were dried over magnesium sulphate and evaporated under reduced pressure to give the title compound (410 mg) as a pale yellow foam.

APCI MS m/z 305 [MH]$^{+1}$H NMR (400 MHz, CD$_3$OD): δ 1.83 (m, 4H), 2.65 (t, 2H), 3.09 (m, 2H), 3.24 (m, 1H), 4.41 (s, 2H), 4.58 (s, 2H), 7.58 (m, 3H).

Preparation 30: (2-Amino-5-fluoro-phenyl)-methanol

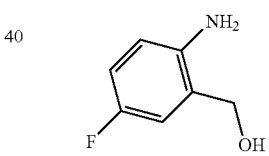

The title compound was prepared from 2-Amino-5-fluoro-benzoic acid, in 81% yield as an off-white solid, following the procedure described in preparation 7.

APCI MS m/z 142 [M+H]$^{+1}$H NMR (400 MHz, CDCl$_3$): δ 4.60 (s, 2H), 6.60 (dd, 1H), 6.77-6.86 (m, 2H)

Preparation 31: 4-Fluoro-2-[5-(3,4,5,6-tetrahydro-2H-[1,2']bipyridinyl-4-yl)-[1,3,4]oxadiazol-2-yl-methoxymethyl]-phenylamine

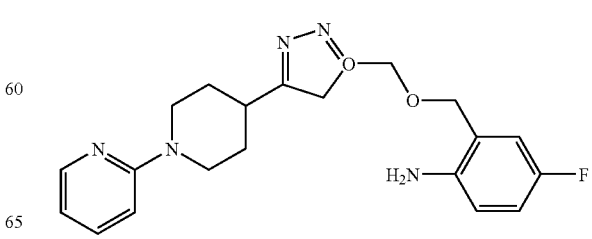

The title compound was prepared from the alcohol of preparation 30 and the oxadiazole of preparation 5, in 60% yield, using the procedure described in preparation 16.

APCI MS m/z 384 [M+H]$^{+1}$H NMR (400 MHz, CDCl$_3$): δ 1.95 (dq, 2H), 2.18 (d, 2H), 3.06-3.21 (m, 3H), 4.33 (td, 2H), 4.60 (s, 2H), 4.70 (s, 2H), 6.58-6.67 (m, 2H), 6.73 (d, 1H), 6.80-6.90 (m, 2H), 7.52 (t, 1H), 8.19 (d, 1H).

Preparation 32:
(2-Amino-4,5-difluoro-phenyl)-methanol

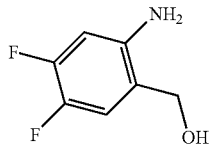

The title compound was prepared from 2-Amino-4,5-difluoro-benzoic acid, in 86% yield as a yellow solid, following the procedure described in preparation 7.

APCI MS m/z 142 [M+H—H$_2$O]$^+$, 160 [M+H]$^{+1}$H NMR (400 MHz, CDCl$_3$): δ 4.10 (bs, 2H), 4.58 (s, 2H), 6.48 (dd, 1H), 6.92 (dd, 1H)

Preparation 33: 4,5-difluoro-2-[5-(3,4,5,6-tetrahydro-2H-[1,2']bipyridinyl-4-yl)-[1,3,4]oxadiazol-2-ylmethoxymethyl]-phenylamine

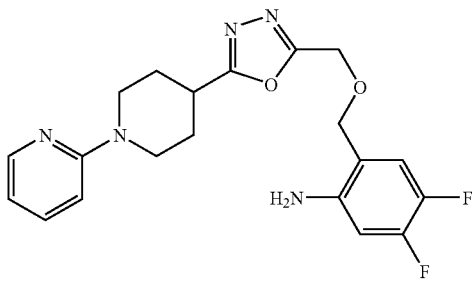

The title compound was prepared from the alcohol of preparation 32 and the oxadiazole of preparation 5, in 50% yield, using the procedure described in preparation 16.

APCI MS m/z 402 [M+H]$^{+1}$H NMR (400 MHz, CDCl$_3$): δ 1.94 (dq, 2H), 2.09 (bd, 1H), 3.09 (bt, 2H), 3.18 (m, 1H), 4.20 (bs, 2H), 4.33 (td, 2H), 4.54 (s, 2H), 4.68 (s, 2H), 6.47 (dd, 1H), 6.64 (t, 1H), 6.72 (d, 1H) 6.92 (dd, 1H), 7.52 (t, 1H), 8.19, (d, 1H)

Preparation 34:
2-Amino-5-trifluoromethoxy-benzoic acid

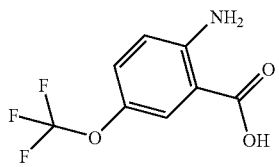

5-Trifluoromethoxy-1H-indole-2,3-dione (3.48 g, 15.0 mmol) was dissolved in 2N aqueous sodium hydroxide (90 ml) and cooled to 17° C. before adding 30% aqueous hydrogen peroxide solution (2.75 ml, 27 mmol) dropwise over 20 minutes. The mixture was stirred at room temperature for 1 hour before adding concentrated hydrochloric acid (7 ml). The resulting brown precipitate was filtered off and dried in vacuo at 50° C. for 66 hours to give the title compound (1.83 g) as a brown solid.

APCI MS m/z 220 [M−H]$^{+1}$H NMR (400 MHz, DMSO): δ 6.80 (d, 1H) 7.24 (dd, 1H), 7.53 (d, 1H)

Preparation 35:
(2-Amino-5-trifluoromethoxy-phenyl)-methanol

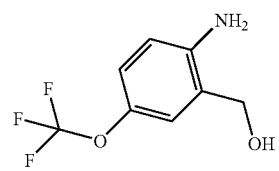

The title compound was prepared from the acid of preparation 34, in 62% yield as a white solid, following the procedure described in preparation 7.

APCI MS m/z 206 [M−H]+$^1$H NMR (400 MHz, CDCl$_3$): δ 4.85 (s, 2H), 6.67 (d, 1H), 6.92-7.00 (m, 2H)

Preparation 36: 2-[5-(3,4,5,6-Tetrahydro-2H-[1,2'] bipyridinyl-4-yl)-[1,3,4]oxadiazol-2-ylmethoxymethyl]-4-trifluoromethoxy-phenylamine

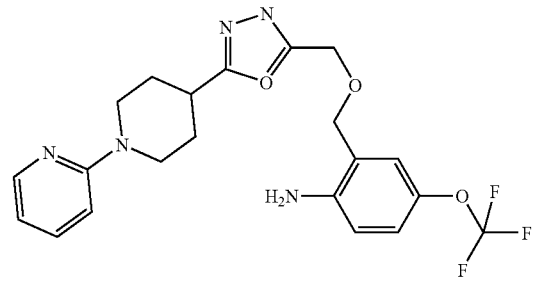

The title compound was prepared from the alcohol of preparation 35 and the oxadiazole of preparation 5, in 28% yield, using the procedure described in preparation 16.

APCI MS m/z 450 [M+H]$^{+1}$H NMR (400 MHz, CDCl$_3$): δ 1.94 (dq, 2H), 2.16 (bd, 1H), 3.09 (t, 2H), 3.17 (m, 1H), 4.37 (bd, 2H), 4.60 (s, 2H), 4.67 (s, 2H), 6.60-6.66 (m, 2H), 6.70 (d, 1H), 6.95-7.07 (m, 2H), 7.49 (t, 1H) 8.19, (d, 1H)

Preparation 37: 4-Methyl-2-[5-(3,4,5,6-tetrahydro-2H-[1,2']bipyridinyl-4-yl)-[1,3,4]oxadiazol-2-yl-methoxymethyl]-phenylamine

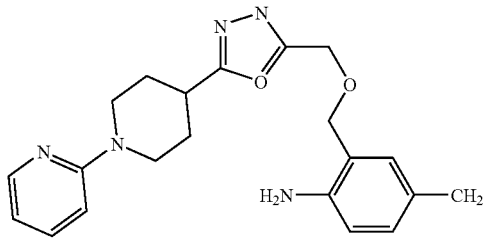

The title compound was prepared from (2-Amino-5-methyl-phenyl)-methanol (see Arch. Pharm. (1929), 583) and the oxadiazole of preparation 5, in 38% yield, using the procedure described in preparation 16.

APCI MS m/z 380 [M+H]$^{+1}$H NMR (400 MHz, CDCl$_3$): δ 1.92 (dq, 2H), 2.16 (bd, 2H), 2.19 (s, 3H), 3.09 (t, 2H), 3.17 (m, 1H), 4.37 (bd, 2H), 4.60 (s, 2H), 4.67 (s, 2H), 6.64 (m, 2H), 6.85 (m, 3H), 7.58 (t, 1H) 8.09, (d, 1H)

Preparation 38: N-[2-(2-Acetylamino-ethyl)-phenyl]-acetamide

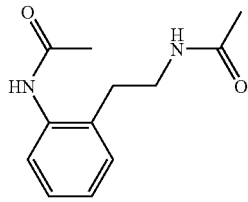

A solution of acetic anhydride (9.6 ml, 101 mmol) in dichloromethane (50 ml) was added dropwise to a solution of 2-(2-Amino-ethyl)-phenylamine (see JACS 99, (1977), 5716)(8.0 g, 46 mmol) and triethylamine (8.4 ml, 60 mmol) in dichloromethane (200 ml). The mixture was stirred at room temperature for 18 hours before partitioning with water (100 ml). The organic layer was washed with a saturated solution of brine (50 ml), dried over magnesium sulphate and evaporated under reduced pressure. The residue was purified by chromatography on silica gel using methanol and ammonium hydroxide in dichloromethane (5:0.5:95) as eluant to give the title compound (4.1 g) as an off-white solid.

APCI MS m/z 221 [M+H]$^{+1}$H NMR (400 MHz, CDCl$_3$): δ 2.04 (s, 3H), 2.33 (s, 3H), 2.81 (t, 2H), 3.28 (m, 2H), 6.19 (bs, 1H), 7.03 (bt, 1H), 7.07 (d, 1H), 7.22 (m, 1H), 8.11 (d, 1H), 8.88 (bs, 1H) Found C, 65.18%, H, 7.27%, N, 12.70%; C$_{12}$H$_{16}$N$_2$O$_2$ requires C, 65.43%, H, 7.32% N, 12.72%

Preparation 39: N-[2-(2-Acetylamino-ethyl)-4-chloro-phenyl]-acetamide

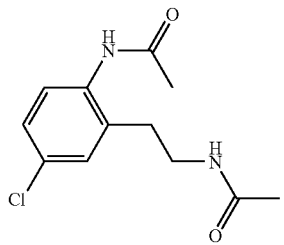

A solution of chlorine in glacial acetic acid (1.22M, 29 ml) was added dropwise to a solution of the acetamide of preparation 38 (7.78 g, 35 mmol) in glacial acetic acid (70 ml) and stirred at room temperature for 2 hours. The glacial acetic acid was removed under reduced pressure. The resulting solid was triturated with a mixture of ethyl acetate and propan-2-ol (7:3, 20 ml) to give the title compound (4.83 g) as a pale yellow solid after filtration.

ESI MS m/z 277 [M+Na]$^{+1}$H NMR (400 MHz, CDCl$_3$): δ 2.03 (s, 3H), 2.33 (s, 3H), 2.79 (m, 2H), 3.22 (m, 2H), 6.28 (bs, 1H), 7.05 (s, 1H), 7.20 (dd, 1H), 8.14 (d, 1H), 9.09 (bs, 1H)

Preparation 40: 2-(2-Amino-ethyl)-4-chloro-phenylamine dihydrochloride

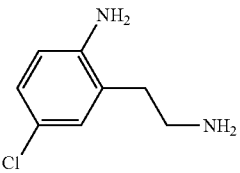

The compound from preparation 39 (4.83 g, 19 mmol) was suspended in 2 molar aqueous hydrochloric acid (50 ml) and heated to 100° C. for 18 hours. Evaporation under reduced pressure gave a red solid which was triturated with propan-2-ol (15 ml) to give the title compound as a pale pink solid (3.5 g) after filtration.

ESI MS m/z 171 [M+H]$^{+1}$H NMR (400 MHz, DMSO-d$_6$): δ 3.00 (t, 2H), 3.12 (m, 2H), 7.38 (dd, 1H), 7.40 (d, 1H), 7.46 (d, 1H), 8.15 (bs, 3H) Found C, 39.29%, H, 5.45%, N, 11.46%; C$_8$H$_{11}$N$_2$.2HCl requires C, 39.45%, H, 5.38%, N, 11.50%

Preparation 41: 4-Chloro-2-(2-{[5-(3,4,5,6-tetrahydro-2H-[1,2']bipyridinyl-4-yl)-[1,3,4]oxadiazol-2-ylmethyl]-amino}-ethyl)-phenylamine

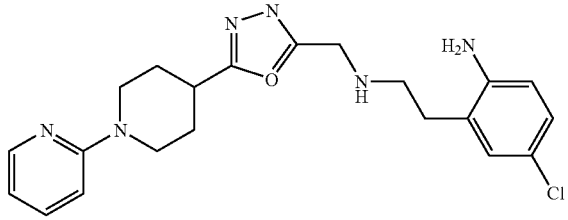

A solution of the amine of preparation 40 (3.5 g, 14.4 mmol) in tetrahydrofuran (50 ml) was added to a solution of the oxadiazole of preparation 5 (4.0 g, 14.4 mmol) and triethylamine (7.0 ml, 50 mmol) in tetrahydrofuran (50 ml) and heated to 50° C. for 4 hours. The reaction mixture was evaporated under reduced pressure and the residue purified by chromatography on silica gel using ethyl acetate as eluant followed by methanol and ammonium hydroxide in dichloromethane (5:0.5:95) to give the title compound as a brown oil (1.35 g).

APCI MS m/z 413 [M+H]$^{+1}$H NMR (400 MHz, CDCl$_3$): δ 1.92 (dq, 2H), 2.15 (bdd, 2H), 2.68 (t, 2H), 2.93 (t, 2H), 3.07 (dt, 2H), 3.14 (m, 1H), 4.01 (s, 2H), 4.31 (btd, 2H), 6.57 (d, 1H), 6.62 (dd, 1H), 6.70 (d, 1H), 6.95-7.02 (m, 2H), 7.27 (t, 1H), 8.19 (d, 1H)

Preparation 42: Morpholine-2,4-dicarboxylic acid 4-tert-butyl ester 2-ethyl ester

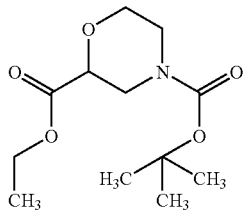

A mixture of 4-phenylmethyl-2-morpholinecarboxylic acid ethyl ester (J. Med. Chem. 1993, 36(6), 683-9), (8.4 g, 32.4 mmol), di-tertbutyl dicarbonate (8.47 g, 38.9 mmol), 1-methyl-1,4-cyclohexadiene (12.37 ml, 110 mmol) and 10% palladium on charcoal (900 mg) in ethanol (330 ml) was heated to 88° C. for 22 hours. TLC analysis showed starting material remaining, so the reaction was cooled, and additional 1-methyl-1,4-cyclohexadiene (2.37 ml, 21 mmol) and 10% palladium on charcoal (900 mg) were added, and the reaction mixture heated for a further 12 hours at 88° C. The cooled mixture was filtered through Arbocel® and the filtrate evaporated under reduced pressure. The residual brown oil was purified by column chromatography on silica gel using an elution gradient of dichloromethane:methanol (100:0 to 95:5) to give the title compound as a pale yellow oil, 5.97 g.

$^1$H NMR (400 MHz, CDCl$_3$): δ 1.30 (t, 3H), 1.43 (s, 9H), 3.10 (m, 2H), 3.50-3.70 (m, 2H), 4.01 (m, 1H), 4.25 (q, 2H).

Preparation 43: Morpholine-2,4-dicarboxylic acid 4-tert-butyl ester

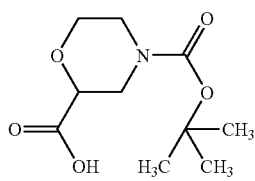

Lithium hydroxide (28 ml, 1M in water, 28 mmol) was added to a solution of the ester from preparation 42 (2.85 g, 11 mmol) in tetrahydrofuran (30 ml) and the reaction stirred at room temperature for 19 hours. The mixture was acidified to pH 3 using 2M hydrochloric acid, and then extracted with dichloromethane (2×70 ml). The combined organic extracts were dried over magnesium sulphate and evaporated under reduced pressure to give the title compound as a yellow solid, 2.36 g.

$^1$H NMR (400 MHz, CDCl$_3$): δ 1.47 (s, 9H), 3.03-3.11 (m, 3H), 3.60 (m, 1H), 3.77-3.86 (m, 1H), 4.02 (m, 1H), 4.15-4.23 (m, 1H).

Preparation 44: 6-Methylene-[1,4]oxazepane-4-carboxylic acid tert-butyl ester

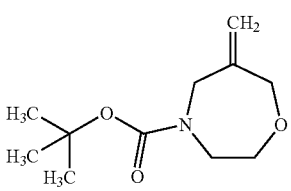

Sodium hydride (992.6 mg, 60% in mineral oil, 24.8 mmol) was added portionwise to a solution of (2-hydroxyethyl)-carbamic acid tert-butyl ester (2 g, 12.4 mmol) in 1-methyl-2-pyrrolidinone (20 ml) at -2° C., in order to maintain the temperature below 5° C. The mixture was then stirred for 30 minutes, cooled to -5° C., and a solution of 3-chloro-2-chloromethyl-1-propene (1.44 ml, 12.4 mmol) in 1-methyl-2-pyrrolidinone (10 ml) added dropwise in order to maintain the temperature below 3° C. Once addition was complete, the reaction mixture was allowed to warm to room temperature and stirred for a further 18 hours. The reaction mixture was diluted with water and extracted with ether (2×50 ml). The combined organic extracts were dried over magnesium sulphate and evaporated under reduced pressure. The residual oil was purified by column chromatography on silica gel using ethyl acetate:pentane (10:90) to give the title compound as a clear oil, 713 mg.

$^1$H NMR (400 MHz, CDCl$_3$): δ 1.46 (s, 9H), 3.51 (d, 2H), 3.72 (d, 2H), 4.00-4.20 (m, 4H), 4.95 (s, 1H), 5.04 (s, 1H). APCI m/z 236 [MNa]$^+$

Preparation 45: 6-Oxo-[1,4]oxazepane-4-carboxylic acid tert-butyl ester

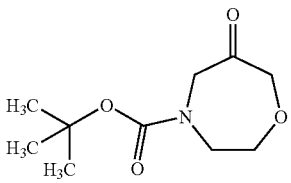

Sodium periodate (1.0 g, 4.69 mmol), followed by osmium tetroxide (0.15 ml, 2.5 wt % solution in tert-butanol, 0.014 mmol), were added to a suspension of the alkene from preparation 44 (500 mg, 2.34 mmol) in dioxan (10 ml) and water (10 ml) and the reaction stirred at room temperature for 48 hours. The reaction was diluted with water (50 ml), brine added, and the mixture extracted with ethyl acetate. The combined organic extracts were dried over magnesium sulphate and evaporated under reduced pressure to afford the title compound as a brown oil, 567 mg.

$^1$H NMR (400 MHz, CDCl$_3$): δ 1.47 (s, 9H), 3.68 (m, 2H), 3.91 (br m, 2H), 4.06 (br m, 2H), 4.11 (s, 2H). APCI m/z 233 [M+NH$_4$]$^+$

Preparation 46: 2-(2-Methylamino-ethyl)-phenylamine

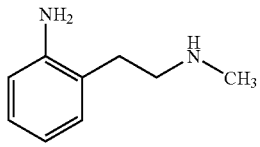

A mixture of N-methyl-N-(2-(2-nitrophenyl)ethyl)amine (WO 9803473, pg 100) (3 g, 16.65 mmol) and Raney® nickel (500 mg) in ethanol (50 ml) was hydrogenated at 60 psi and room temperature for 2 hours. The mixture was filtered through Celite® and the filtrate evaporated under reduced pressure to give the title compound as an oil.
APCI MS m/z 152 [MH]$^+$

Preparation 47: 2-(1-Methylamino-ethyl)-phenylamine

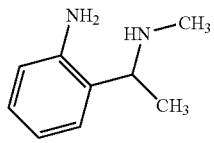

Acetic acid (10 drops) was added to a solution of methylamine (10 g) in dichloromethane (150 ml) cooled to 5° C., followed by o-aminoacetophenone (3.5 g, 25.9 mmol), and the solution stirred for 10 minutes. Sodium triacetoxyborohydride (1.5 g, 38.8 mmol) was added and the reaction stirred at room temperature for 72 hours. The reaction was diluted with water, the layers separated, and the organic solution evaporated under reduced pressure to give the title compound as a yellow oil.
$^1$H NMR (400 MHz, CDCl$_3$): δ 1.44 (s, 3H), 2.36 (s, 3H), 4.77-5.08 (br s, 1H), 6.56-6.78 (m, 2H), 7.02 (m, 2H).

Preparation 48: N-{2-[2-(Acetyl-methyl-amino)-ethyl]-phenyl}-acetamide

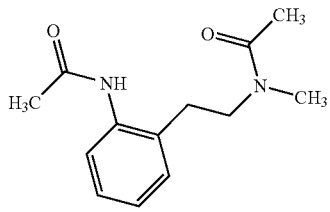

4-Methylmorpholine (4.45 g, 44 mmol) and acetic anhydride (4.49 g, 44 mmol) were added to an ice-cooled solution of the amine from preparation 46 (2.2 g, 14.67 mmol) in dichloromethane (50 ml). 4-Pyrrolidinopyridine (100 mg, 0.7 mmol) was then added and the reaction mixture stirred at room temperature for 2 hours. The reaction mixture was then washed with dilute hydrochloric acid (2×), sodium carbonate solution (2×), and brine (2×). It was dried over magnesium sulphate and evaporated under reduced pressure to afford the title compound as an oil.
$^1$H NMR (400 MHz, CDCl$_3$): δ 2.16 (s, 3H), 2.36 (s, 3H), 2.80 (m, 2H), 3.14 (s, 3H), 3.36 (m, 2H), 7.01 (m, 1H), 7.18 (m, 1H), 7.22 (m, 1H), 8.22 (d, 1H), 9.22 (s, 1H). APCI m/z 235 [MH]$^+$

Preparation 49: N-{2-[1-(Acetyl-methyl-amino)-ethyl]-phenyl}-acetamide

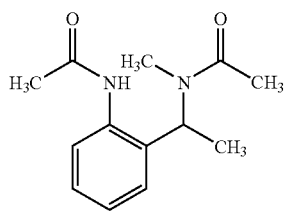

The title compound was obtained as an oil, from the amine from preparation 47 and acetic anhydride, following a similar procedure to that described in preparation 48, except that no 4-pyrrolidinopyridine was added.
$^1$H NMR (400 MHz, CDCl$_3$): δ 1.55 (d, 3H), 2.16 (s, 3H), 2.20 (s, 3H), 2.78 (s, 3H), 6.02 (q, 1H), 7.09 (m, 2H), 7.36 (m, 2H), 8.25 (d, 1H), 9.40 (br s, 1H). APCI MS m/z 257 [MNa]$^+$

Preparation 50: N-{2-[2-(Acetyl-methyl-amino)-ethyl]-4-chloro-phenyl}-acetamide

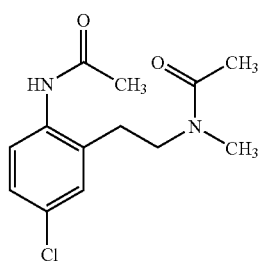

Chlorine (7.3 g) was bubbled into acetic acid (102 g). A portion of this solution (15 g) was added to an ice-cooled solution of the compound from preparation 48 (3.3 g, 14.1 mmol) in acetic acid (50 ml), and the reaction stirred at room temperature for 20 hours. The mixture was concentrated under reduced pressure, and the residue dissolved in ethyl acetate. This solution was washed with saturated sodium carbonate solution and brine. It was then dried over magnesium sulphate and evaporated under reduced pressure, to afford the title compound as a brown solid, 2.7 g.
$^1$H NMR (400 MHz, CDCl$_3$): δ 2.16 (s, 3H), 2.30 (s, 3H), 2.78 (m, 2H), 3.12 (s, 3H), 3.30 (m, 2H), 7.05 (s, 1H), 7.19 (d, 1H), 8.20 (d, 1H), 9.38 (s, 1H). APCI MS m/z 291 [MNa]$^+$

Preparation 51: N-{2-[1-(Acetyl-methyl-amino)-ethyl]-4-chloro-phenyl}-acetamide

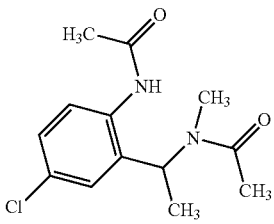

Chlorine (1.88 g) was bubbled into a solution of the compound from preparation 49 (6.4 g, 26.6 mmol) in acetic acid (30 ml) and the reaction stirred at room temperature for 24 hours. The mixture was concentrated under reduced pressure and the residue suspended in ethyl acetate. The solution was then washed with sodium bicarbonate solution and brine, before being dried over magnesium sulphate and evaporated under reduced pressure. The product was recrystallised from isopropyl ether and methanol to give the title compound, 3.5 g.

$^1$H NMR (400 MHz, CDCl$_3$): δ 1.60 (d, 3H), 2.16 (s, 3H), 2.20 (s, 3H), 2.79 (s, 3H), 6.00 (q, 1H), 7.24 (m, 1H), 8.25 (d, 1H), 9.39 (s, 1H). APCI MS m/z 291 [MH]+

Preparation 52: 4-Chloro-2-(2-methylamino-ethyl)-phenylamine

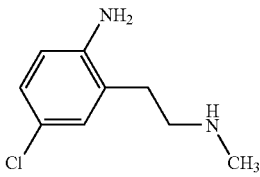

A solution of the compound from preparation 50 (2.6 g, 9.68 mmol) in 2N hydrochloric acid (100 ml) was stirred at 80° C. for 1 hour, and a further 72 hours at room temperature. TLC analysis showed starting material remaining, so additional 12N hydrochloric acid (50 ml) was added and the reaction stirred at 90° C. for a further 3 hours. The cooled mixture was basified using aqueous 0.88 ammonia, and then extracted with ethyl acetate (3×). The combined organic extracts were washed with formaldehyde solution (3×) and brine (2×), before being dried over magnesium sulphate and evaporated under reduced pressure to give the title compound as an oil, 1.29 g.

$^1$H NMR (400 MHz, CDCl$_3$): δ 2.42 (s, 3H), 2.65 (t, 2H), 2.83 (t, 2H), 6.59 (d, 1H), 6.99 (m, 2H).

Preparation 53: 4-Chloro-2-(1-methylamino-ethyl)-phenylamine

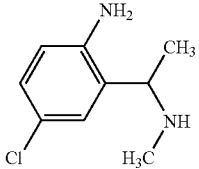

A solution of the compound from preparation 49 (3.40 g, 12.65 mmol) in 12N hydrochloric acid (150 ml) was stirred at 100° C. for 24 hours. The cooled solution was treated carefully with aqueous 0.88 ammonia solution, and extracted with dichloromethane (3×). The combined organic extracts were dried over magnesium sulphate and evaporated under reduced pressure to give an oil, 2.24 g.

$^1$H NMR (400 MHz, CDCl$_3$): δ 1.42 (d, 3H), 2.38 (s, 3H), 3.76 (q, 1H), 6.50 (d, 1H), 6.99 (m, 2H). APCI MZ m/z 185 [MH]$^+$

Preparation 54: 2-(5-Chloro-2-nitrophenoxy)-ethanol

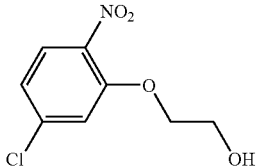

Sodium hydride (125 mg, 60% dispersion in mineral oil, 3.13 mmol) was added to a mixture of 4-chloro-2-fluoronitrobenzene (500 mg, 2.85 mmol) and ethylene glycol (0.18 ml, 3.13 mmol) in 1-methyl-2-pyrrolidinone (5 ml) and the reaction stirred at 80° C. for 18 hours. TLC analysis showed starting material remaining, so additional sodium hydride (114 mg, 60% dispersion in mineral oil, 2.85 mmol) and ethylene glycol (0.82 ml, 14.25 mmol) were added and the reaction stirred at 110° C. for a further 18 hours. The cooled mixture was partitioned between water and dichloromethane, and the layers separated. The organic phase was dried over magnesium sulphate and evaporated under reduced pressure. The residue was purified by column chromatography on silica gel using ethyl acetate:pentane (50:50) as eluant to afford the title compound as a solid, 290 mg.

$^1$H NMR (400 MHz, CDCl$_3$): δ 4.00 (t, 2H), 4.22 (t, 2H), 7.04 (d, 1H), 7.10 (s, 1H), 7.85 (d, 1H).

Preparation 55: 3-[(5-Chloro-2-nitro-benzyl)-amino]-propionic acid methyl ester

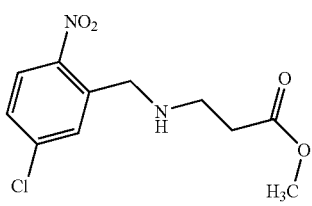

A mixture of 4 Å molecular sieve powder (16.9 g) and lithium hydroxide monohydrate (1.80 g, 43 mmol) in N,N-dimethylformamide (100 ml) was stirred at room temperature for 20 minutes. β-Alanine methyl ester hydrochloride (5.0 g, 35.8 mmol) was added and the mixture stirred for a further 45 minutes. 2-(Bromomethyl)-4-chloro-1-nitrobenzene (J. Het. Chem. 1972; 9(1), 119-22) (8.98 g, 35.8 mmol) was added and the reaction stirred at room temperature for 16 hours. The mixture was filtered, the filtrate diluted with ethyl acetate (150 ml), then washed with brine (3×150 ml) and extracted with 2N hydrochloric acid (2×75 ml). The combined acidic extracts were basified using sodium carbonate, then extracted with ethyl acetate. The combined organic extracts were dried over magnesium sulphate and evaporated under reduced pressure to afford the title compound, 1.29 g.

$^1$H NMR (400 MHz, CDCl$_3$): δ 2.56 (t, 2H), 2.90 (t, 2H), 3.69 (s, 3H), 4.05 (s, 2H), 7.38 (dd, 1H), 7.72 (d, 1H), 7.94 (d, 1H). APCI MS m/z 272 [M−H]$^-$

Preparation 56: 3-[(5-Chloro-2-nitro-benzyl)-methyl-amino]-propionic acid methyl ester

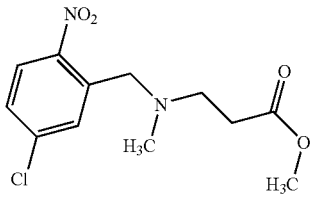

Formaldehyde (37% aq solution, 1.2 g, 26 mmol), followed by sodium triacetoxyborohydride (7.7 g, 36.4 mmol) and formic acid (30% aq, 3.1 g, 104 mmol), were added to a solution of the amine from preparation 55 (7.1 g, 26 mmol) in dichloromethane (70 ml), and the reaction stirred at room temperature for 18 hours. The mixture was concentrated under reduced pressure, the residue diluted with ethyl acetate, and the solution washed with 1N sodium hydroxide and brine. The solution was concentrated under reduced pressure and the crude product purified by column chromatography on silica gel using an elution gradient of pentane:ethyl acetate (100:0 to 95:5) to give the title compound, 6 g.

$^1$H NMR (400 MHz, CDCl$_3$): δ 2.20 (s, 3H), 2.44 (t, 2H), 2.72 (t, 2H), 3.64 (s, 3H), 3.78 (s, 2H), 7.35 (dd, 1H), 7.63 (s, 1H), 7.80 (d, 1H).

Preparation 57:
2-(2-Amino-5-chloro-phenoxy)-ethanol

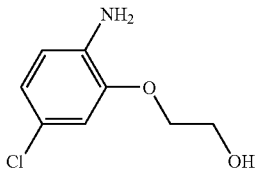

A mixture of the compound from preparation 56 (280 mg, 1.29 mmol) and platinum oxide (80 mg) in ethanol (25 ml) was hydrogenated at room temperature and 60 psi for 5 hours. The mixture was filtered, washing through with further ethanol, and the filtrate evaporated under reduced pressure. The crude product was purified by column chromatography on silica gel using dichloromethane:methanol:0.88 ammonia (95:5:0.5) to afford the title compound as an off-white solid, 195 mg.

$^1$H NMR (400 MHz, CDCl$_3$): δ 3.98 (t, 2H), 4.16 (t, 2H), 6.75 (d, 1H), 6.82 (m, 2H). APCI MS m/z 188 [MH]$^+$

Preparation 58: 3-[(2-Amino-5-chloro-benzyl)-methyl-amino]-propionic acid methyl ester

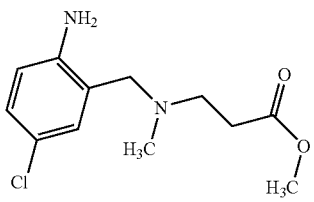

A mixture of the compound from preparation 56 (6.01 g, 22.0 mmol), and platinum oxide (500 mg) in ethanol (100 ml) was hydrogenated at 60 psi and room temperature for 1 hour. The mixture was filtered through Celite®, and the filtrate evaporated under reduced pressure. The crude product was purified by column chromatography on silica gel using dichloromethane:methanol:0.88 ammonia (90:10:1) to afford the title compound.

$^1$H NMR (400 MHz, CDCl$_3$): δ 2.16 (s, 3H), 2.50 (t, 2H), 2.72 (t, 2H), 3.44 (s, 2H), 3.63 (s, 3H), 4.62 (br s, 2H), 6.56 (d, 1H), 6.98 (s, 1H), 7.01 (dd, 1H).

Preparation 59: 3-[(2-Amino-5-chloro-benzyl)-methyl-amino]-propionic acid dihydrochloride

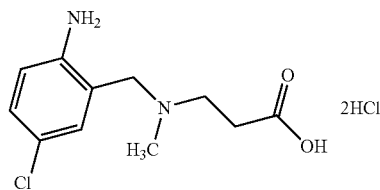

A mixture of the ester from preparation 58 (1.1 g, 4.3 mmol) in tetrahydrofuran (10 ml), water (1.4 ml) and hydrochloric acid in dioxan (4M, 10 ml) was stirred at room temperature for 2 hours, followed by an additional 8 hours at 90° C. The cooled solution was concentrated under reduced pressure and the residue azeotroped with ethyl acetate and toluene to afford the title compound.

$^1$H NMR (400 MHz, DMSOd$_6$): δ 2.62 (s, 3H), 2.81 (t, 2H), 3.30 (t, 2H), 4.22 (s, 2H), 6.78 (m, 1H), 7.18 (d, 1H), 7.39 (s, 1H). APCI MS m/z 243 [MH]$^+$

Preparation 60: Methyl-[5-(3,4,5,6-tetrahydro-2H-[1,2']bipyridinyl-4-yl)-[1,3,4]oxadiazol-2-ylmethyl]-amine

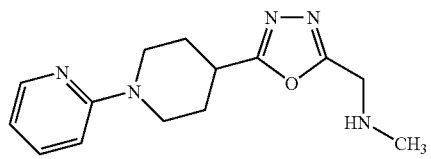

Methylamine (2.23 ml, 33% solution in ethanol, 17.9 mmol) was added to a solution of the chloride from preparation 5 (1 g, 3.59 mmol) in tetrahydrofuran (20 ml), and the solution stirred at room temperature for 18 hours. Additional methylamine (10 ml, 33% solution in ethanol) was added and the reaction stirred for a further 72 hours. The reaction was evaporated under reduced pressure, the solid triturated with ethyl acetate and the precipitate removed by filtration. The filtrate was concentrated under reduced pressure and the residue azeotroped with dichloromethane to afford the title compound as a crystalline solid.

$^1$H NMR (400 MHz, CDCl$_3$): δ 1.98 (m, 2H), 2.17 (br d, 2H), 2.48 (s, 3H), 3.18 (t, 2H), 3.35 (m, 1H), 3.95 (s, 2H), 4.58 (br d, 2H), 6.62 (dd, 1H), 6.68 (d, 1H), 7.46 (dd, 1H), 8.18 (d, 1H). APCI m/z 274 [MH]$^+$

Preparation 61: 4-Chloro-2-{2-[5-(3,4,5,6-tetrahydro-2H-[1,2']bipyridinyl-4-yl)-[1,3,4]oxadiazol-2-ylmethoxy]-ethoxy}-phenylamine

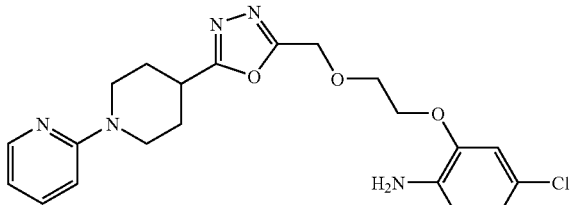

Sodium hydride (60% dispersion in mineral oil, 45 mg, 1.1 mmol) was added to an ice-cooled solution of the alcohol from preparation 57 (190 mg, 1 mmol) in tetrahydrofuran (10 ml), and the solution stirred for 30 minutes. A solution of the chloride from preparation 5 (310 mg, 1.1 mmol) in tetrahydrofuran (6 ml) was added and the reaction stirred at room temperature for 18 hours. The reaction was quenched by the addition of water (1 ml) and the mixture was then partitioned between dichloromethane and saturated aqueous sodium bicarbonate solution. The layers were separated, the organic phase dried over magnesium sulphate and evaporated under reduced pressure. The residue was purified by column chromatography on silica gel using an elution gradient of ethyl acetate:methanol (96:4 to 95:5) to afford the title compound as a pale orange oil, 280 mg.

$^1$H NMR (400 MHz, CDCl$_3$): δ 1.99 (m, 2H), 2.20 (m, 2H), 3.18 (m, 3H), 2.96 (m, 2H), 4.18 (m, 2H), 4.30 (m, 2H), 4.80 (s, 2H), 6.60-6.80 (m, 5H), 7.55 (m, 1H), 8.20 (m, 1H). APCI MS m/z 452 [MNa]$^+$

Preparation 62: 2-Amino-5-chloro-N-methyl-N-[5-(3,4,5,6-tetrahydro-2H-[1,2']bipyridinyl-4-yl)-[1,3,4]oxadiazol-2-ylmethyl]-benzamide

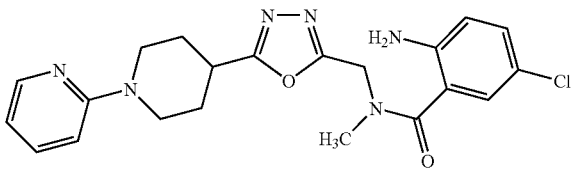

5-Chloroanthranallic acid (314 mg, 1.83 mmol), 1-(3-dimethylaminopropyl)-3-ethylcarbodiimide hydrochloride (350 mg, 1.83 mmol) and N-methyl morpholine (0.4 ml, 3.64 mmol) were added to a solution of the amine from preparation 60 (500 mg, 1.83 mmol) in dichloromethane (20 ml) and the reaction stirred at room temperature for 3 hours. The reaction mixture was washed with 10% citric acid solution, saturated sodium bicarbonate solution, and brine, then dried over magnesium sulphate and evaporated under reduced pressure. The combined aqueous phases were extracted with dichloromethane (2×25 ml), and the combined dichloromethane extracts evaporated under reduced pressure. The combined crude products were purified by column chromatography on silica gel using ethyl acetate as eluant, and the product azeotroped with dichloromethane and ether to afford the title compound as a white solid, 278 mg.

$^1$H NMR (400 MHz, CDCl$_3$): δ 1.92 (m, 2H), 2.16 (d, 2H), 3.02-3.22 (m, 6H), 4.32 (d, 2H), 4.85 (br s, 2H), 6.63 (m, 2H), 6.70 (d, 1H), 7.14 (m, 2H), 7.50 (dd, 1H), 8.20 (d, 1H). APCI MS m/z 427 [MH]+

Preparation 63: 4-Chloro-2-(2-{methyl-[5-(1-pyrimidin-2-yl-piperidin-4-yl)-[1,3,4]oxadiazol-2-ylmethyl]-amino}-ethyl)-phenylamine

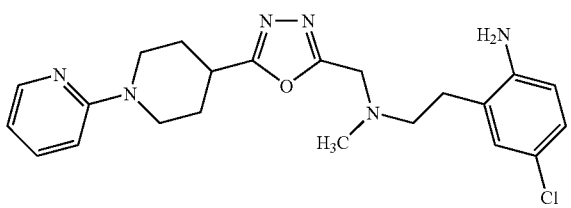

A mixture of the amine from preparation 52 (1.1 g, 5.96 mmol), the chloride from preparation 6 (1.51 g, 5.42 mmol), N-methylmorpholine (0.60 g, 5.96 mmol) and sodium iodide (400 mg, 2.66 mmol) in tetrahydrofuran (50 ml) was stirred at 50° C. for 18 hours. The reaction was concentrated under reduced pressure and the residue was dissolved in ethyl acetate. The solution washed with water (3×) and brine, then dried over magnesium sulphate and evaporated under reduced pressure, to give the title compound as a yellow oil, 1.77 g.

APCI MS m/z 428 [MH]$^+$

Preparation 64: 4-Chloro-2-(1-{[4-(4-chloro-phenyl)-5-(1-pyrimidin-2-yl-piperidin-4-yl)-4H-[1,2,4]triazol-3-ylmethyl]-methyl-amino}-ethyl)-phenylamine

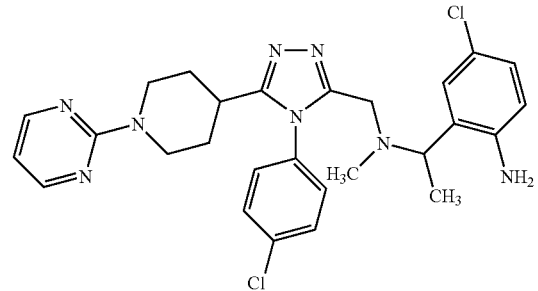

A mixture of the chloride from preparation 6 (1.37 g, 4.92 mmol), the amine from preparation 53 (1.0 g, 5.41 mmol), and potassium carbonate (0.75 g, 5.41 mmol) in tetrahydrofuran (50 ml) was stirred at room temperature for 18 hours. Sodium iodide (40 mg, 2.67 mmol) was added and the reaction stirred for a further 24 hours. The reaction was concentrated under reduced pressure, the residue dissolved in ethyl acetate and the solution washed with brine. The solution was dried over magnesium sulphate and evaporated under reduced pressure. The crude product was purified by column chromatography on silica gel using dichloromethane:methanol (99:1) to give the title compound as an oil, 1.30 g.

$^1$H NMR (400 MHz, CDCl$_3$): δ 1.45 (d, 3H), 1.86 (m, 2H), 2.18 (m, 2H), 2.35 (s, 3H), 3.20 (m, 3H), 3.78 (m, 2H), 3.88 (d, 1H), 4.74 (m, 2H), 6.50 (dd, 1H), 6.58 (d, 1H), 7.00 (m, 2H), 8.32 (s, 2H). APCI MS m/z 428 [MH]$^+$

Preparation 65: 3-[8-Chloro-1-(3,4,5,6-tetrahydro-2H-[1,2']bipyridinyl-4-yl)-4H,6H-2,3,5,10b-tetraazabenzo[e]azulene-5-carbonyl]-pyrrolidine-1-carboxylic acid tert-butyl ester

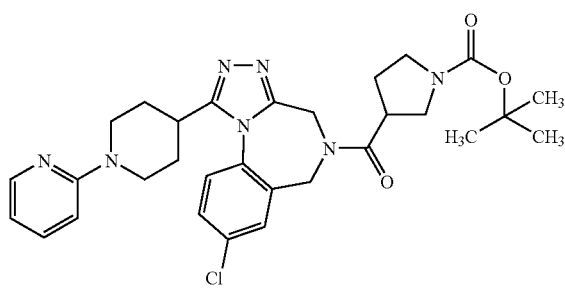

1-Hydroxybenzotriazole hydrate (426 mg, 3.16 mmol), 1-(3-dimethylaminopropyl)-3-ethylcarbodiimide hydrochloride (658 mg, 3.42 mmol), triethylamine (0.91 ml, 6.58 mmol) and 1-tert-butyl-1,3-pyrrolidinedicarboxylate (J. Med. Chem. 44; 1; 2001; 94-1004) (900 mg, 3.95 mmol) were added to a suspension of the amine from example 4 (1 g, 2.63 mmol) in dichloromethane (20 ml), and the reaction stirred at room temperature for 3 hours. TLC analysis showed starting material remaining, so additional 1-hydroxybenzotriazole hydrate (355 mg, 2.63 mmol), 1-(3-dimethylaminopropyl)-3-ethylcarbodiimide hydrochloride (506 mg, 2.63 mmol) and 1-tertbutyl-1,3-pyrrolidinedicarboxylate (600 mg, 2.63 mmol) were added and the reaction stirred for a further 18 hours. The mixture was partitioned between 2N sodium hydroxide solution and dichloromethane and the layers separated. The organic solution was evaporated under reduced pressure and the residue purified by column chromatography on silica gel using dichloromethane:methanol (95:5) as eluant to afford the title compound as an off-white foam, 690 mg.

$^1$H NMR (400 MHz, CDCl$_3$): δ 1.41 (s, 9H), 1.68-2.30 (m, 6H), 2.81-3.18 (m, 3H), 3.20-3.81 (m, 5H), 3.83-5.36 (m, 6H), 6.60 (dd, 1H), 6.66 (d, 1H), 7.38-7.62 (m, 4H), 8.18 (m, 1H). APCI MS m/z 578 [MH]$^+$

Preparations 66 to 72

The following preparations of general formula:

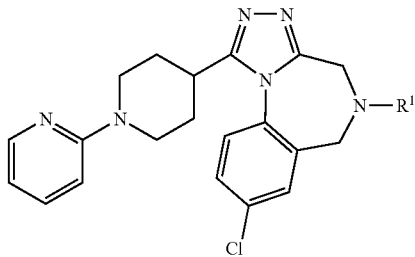

were prepared from the amine from example 4 and the appropriate acid, following a similar procedure to that described in preparation 65.

| Prep No | R$^1$ | Yield (%)/Form | Data |
|---|---|---|---|
| 66 | (2-pyrrolidinyl Boc, one stereo) | 42 | $^1$H NMR (400 MHz, CDCl$_3$):δ 1.06-1.58 (m, 11H), 1.78-2.40 (m, 6H), 2.80-3.20 (m, 3H), 3.40-3.77 (m, 3H), 4.19-4.62 (m, 4H), 5.02-5.60 (m, 2H), 6.58-6.72 (m, 2H), 7.37-7.66 (m, 4H), 8.18 (m, 1H). APCI MS m/z 577 [M-H]$^-$ |
| 67 | (2-pyrrolidinyl Boc, other stereo) | 79 White solid | $^1$H NMR (400 MHz, CDCl$_3$):δ 1.06-1.58 (m, 11H), 1.78-2.40 (m, 6H), 2.80-3.20 (m, 3H), 3.40-3.77 (m, 3H), 4.19-4.62 (m, 4H), 5.02-5.60 (m, 2H), 6.58-6.72 (m, 2H), 7.37-7.66 (m, 4H), 8.18 (m, 1H). APCI MS m/z 577 [M-H]$^-$ |
| 68 | (3-piperidinyl Boc) | 42 | APCI MS m/z 591 [M-H]$^-$ |

| Prep No | R¹ | Yield (%)/Form | Data |
|---|---|---|---|
| 69 | | 58 white foam | APCI MS m/z 592 [M-H]⁺ |
| 70 | | 58 white foam | APCI MS m/z 592 [M-H]⁺ |
| 71[a] | | 55 off-white foam | APCI MS m/z 594 [M-H]⁺ |
| 72 | | 69 | APCI MS m/z 616 [MNa]⁺ |

[a] 4-(tert-butoxycarbonyl)morpholine-3-carboxylic acid (WO 03035077, example 6, step 1, pg 88) was used as the starting acid.

Preparation 73: 3-[8-Chloro-1-(3,4,5,6-tetrahydro-2H-[1,2']bipyridinyl-4-yl)-4H,6H-10b-tetraazabenzo[e]azulen-5-yl]-azetidine-1-carboxylic acid tertbutyl ester

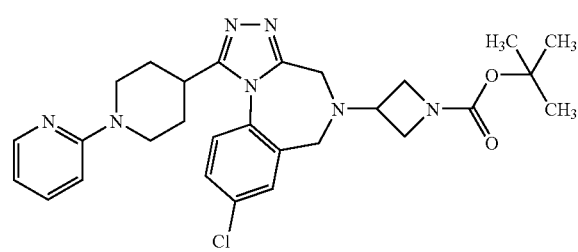

3-Oxo-azetidine-1-carboxylic acid tert-butyl ester (JP 2002/255932, pg 6) (562 mg, 3.16 mmol) and sodium triacetoxyborohydride (1.12 g, 5.26 mmol) were added to a suspension of the amine from example 4 (1 g, 2.63 mmol) in dichloromethane (50 ml), and the reaction stirred at room temperature for 72 hours. The mixture was partitioned between 2N sodium hydroxide and dichloromethane, the layers separated, and the organic phase evaporated under reduced pressure. The residual yellow oil was purified by column chromatography on silica gel using dichloromethane:methanol:0.88 ammonia (95:5:0.5) as eluant to afford the title compound as a white foam.

¹H NMR (400 MHz, CDCl₃): δ 1.42 (s, 9H), 1.60-2.46 (m, 4H), 2.90-3.00 (m, 2H), 3.12 (m, 1H), 3.50 (m, 2H), 3.79-3.90 (m, 3H), 3.99-4.60 (m, 6H), 6.60 (m, 1H), 6.60 (d, 1H), 7.28 (d, 1H), 7.42-7.56 (m, 2H), 7.58 (dd, 1H), 8.18 (m, 1H). APCI MS m/z 558 [MNa]⁺

Preparation 74: 3-[8-Chloro-1-(3,4,5,6-tetrahydro-2H-[1,2']bipyridinyl-4-yl)-4H,6H-2,3,5,10b-tetraazabenzo[e]azulen-5-yl]-pyrrolidine-1-carboxylic acid tert-butyl ester

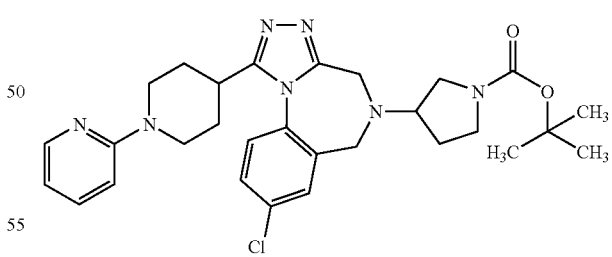

The title compound was obtained as an off-white solid in 53% yield from the amine from example 4 and 3-oxo-pyrrolidine-1-carboxylic acid tertbutyl ester, following a similar procedure to that described in preparation 73, except that acetic acid (3 drops) was also added to the reaction.

¹H NMR (400 MHz, CDCl₃): δ 1.44 (s, 9H), 1.50-1.70 (m, 2H), 1.75-2.55 (m, 5H), 2.80-3.90 (m, 11H), 4.20-4.45 (m, 2H), 6.60 (dd, 1H), 6.66 (d, 1H), 7.35 (d, 1H), 7.41-7.57 (m, 3H), 8.18 (d, 1H). APCI MS m/z 572 [MNa]⁺

Preparation 75: 4-[8-Chloro-1-(3,4,5,6-tetrahydro-2H-[1,2'}bipyridinyl-4-yl)-4H,6H-2,3,5,10b-tetraazabenzo[e]azulen-5-yl]-piperidine-1-carboxylic acid tertbutyl ester

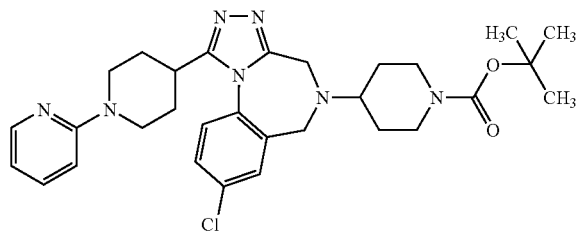

tert-Butyl-4-oxo-piperidinecarboxylate (628 mg, 3.16 mmol) and sodium triacetoxyborohydride (1.12 g, 5.26 mmol) were added to a suspension of the amine from example 4 (1 g, 2.63 mmol) in dichloromethane (50 ml), and the reaction was stirred at room temperature for 72 hours. TLC analysis showed starting material remaining, so additional tert-butyl-4-oxo-piperidinecarboxylate (628 mg, 3.16 mmol) and sodium triacetoxyborohydride (1.12 g, 5.26 mmol) were added, and the reaction stirred for a further 5 hours. The mixture was partitioned between 2N sodium hydroxide (100 ml) and dichloromethane (100 ml), and the layers were separated. The organic phase was washed with brine (100 ml), dried over magnesium sulphate and evaporated under reduced pressure to afford the title compound as a colourless gum.

$^1$H NMR (400 MHz, CDCl$_3$): δ 1.42 (s, 9H), 1.72-2.20 (m, 8H), 2.40 (m, 2H), 2.61-2.78 (m, 1H), 2.92-3.20 (m, 2H), 3.40-3.60 (m, 1H), 3.70 (m, 2H), 3.82 (m, 2H), 4.04-4.19 (m, 2H), 4.34 (m, 2H), 6.60 (m, 1H), 6.66 (d, 1H), 7.32 (d, 1H), 7.42-56 (m, 3H), 8.18 (m, 1H).

Preparation 76: 6-[8-Chloro-1-(3,4,5,6-tetrahydro-2H-[1,2'}bipyridinyl-4-yl)-4H,6H-2,3,5,10b-tetraazabenzo[e]azulen-5-yl]-[1,4]oxazepane-4-carboxylic acid

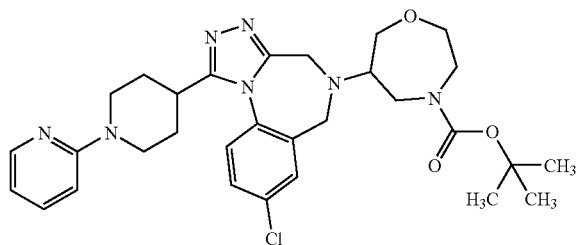

A solution of the ketone from preparation 45 (286 mg, 1.33 mmol) in dichloromethane (5 ml) followed by sodium triacetoxyborohydride (281.5 mg, 1.33 mmol) was added to a suspension of the amine from example 4 (500 mg, 1.31 mmol) in dichloromethane (20 ml), and the reaction stirred at room temperature for 18 hours. TLC analysis showed starting material remaining, so additional ketone (250 mg, 1.16 mmol) was added, and the reaction stirred for a further 70 hours. Saturated sodium bicarbonate solution (15 ml) was added and the mixture stirred at room temperature for 30 minutes. The layers were separated and the organic phase was washed with brine, dried over magnesium sulphate and evaporated under reduced pressure. The residual brown oil was purified by column chromatography on silica gel using dichloromethane:methanol (95:5) as eluant to afford the title compound, 189 mg.

APCI MS m/z 580 [MH]$^+$

Preparation 77: 1-[8-Chloro-1-(3,4,5,6-tetrahydro-2H-[1,2'}bipyridinyl-4-yl)-4H,6H-2,3,5,10b-tetraazabenzo[e]azulen-5-yl]-2-dimethylamino-ethanone

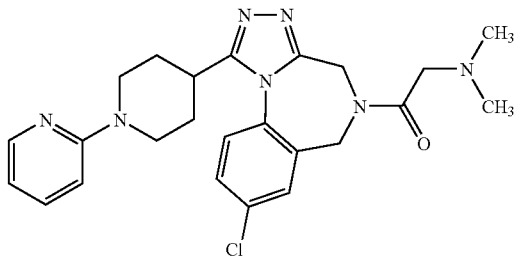

1-Hydroxybenzotriazole hydrate (107 mg, 0.79 mmol), 1-(3-dimethylaminopropyl)-3-ethylcarbodiimide hydrochloride (184 mg, 0.86 mmol), triethylamine (0.23 ml, 1.65 mmol) and N,N-dimethyl glycine (71.2 mg, 0.69 mmol) were added to a suspension of the amine from example 4 (250 mg, 0.66 mmol) in dichloromethane (10 ml) and the reaction stirred at room temperature for 18 hours. The reaction was partitioned between 2N sodium hydroxide solution (10 ml) and dichloromethane (10 ml), the layers separated, and the aqueous phase extracted with further dichloromethane (10 ml). The combined organic solutions were washed with brine (20 ml), dried over magnesium sulphate and evaporated under reduced pressure. The residual gum was purified by column chromatography on silica gel using dichloromethane:methanol:0.88 ammonia (95:5:0.5) to give the title compound as a white foam, 220 mg.

$^1$H NMR (400 MHz, CDCl$_3$): δ 1.58-1.88 (m, 4H), 2.20-2.40 (2×s, 6H), 2.60-4.60 (m, 9H), 5.28-5.60 (m, 2H), 6.60 (m, 1H), 6.66 (d, 1H), 7.40 (dd, 1H), 7.46 (m, 1H), 7.57 (m, 1H), 7.60 (d, 1H), 8.18 (m, 1H). APCI MS m/z 466 [MH]$^+$

Preparation 78: 8-Chloro-5-methyl-3,4,5,6-tetrahydro-1H-benzo[b][1,5]diazocin-2-one

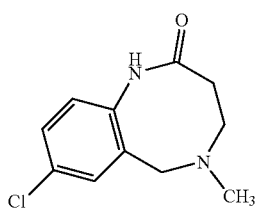

A mixture of the compound from preparation 59 (1.35 g, 4.3 mmol), N-methylmorpholine (2.2 ml, 19.3 mmol) and O-benzotriazol-1-yl-N,N,N',N'-tetramethyluronium hexafluorophosphate (2.3 g, 6 mmol) in dichloromethane (100 ml) was stirred at room temperature for 18 hours. The reaction was washed with 1M sodium hydroxide solution (3×), water and brine, then dried over magnesium sulphate and concentrated under reduced pressure. The residue was trituated with ethyl acetate and the resulting solid filtered off and dried to afford the title compound. The filtrate was concentrated under reduced pressure and the residue was purified by column chromatography on silica gel using dichloromethane:methanol (100:0 to 95:5) to afford additional title compound, 550 mg as a white solid (in total).

$^1$H NMR (400 MHz, CDCl$_3$): δ 2.30 (m, 2H), 2.45 (s, 3H), 2.98 (m, 2H), 3.60 (s, 2H), 7.04 (d, 1H), 7.25 (d, 1H), 7.38 (s, 1H), 7.78 (br s, 1H). APCI MS m/z 225 [MH]$^+$

Preparation 79: 8-Chloro-5-methyl-3,4,5,6-tetrahydro-1H-benzo[b][1,5]diazocine-2-thione

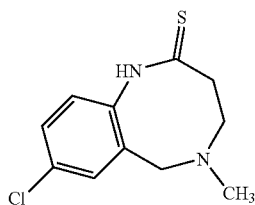

Sodium carbonate (254 mg, 2.4 mmol) was added to a solution of phosphorous pentasulphide (1.07 g, 2.4 mmol) in tetrahydrofuran (5.5 ml) at 5° C. The solution was cooled to 3° C., and the compound from preparation 78 (540 mg, 2.4 mmol) was added. Water (83 μl, 4.6 mmol) was added dropwise, and the resulting mixture was stirred at room temperature for 18 hours. The reaction was diluted with 0.88 ammonia, and extracted with dichloromethane (2×). The combined organic extracts were washed with brine, dried over magnesium sulphate and evaporated under reduced pressure. The residue was adsorbed onto silica gel and purified by column chromatography on silica gel using dichloromethane:methanol:0.88 ammonia (100:0:0 to 90:10:1) to afford the title compound (0.23 g).

$^1$H NMR (400 MHz, CDCl$_3$): δ 2.42 (s, 3H), 2.78 (m, 2H), 3.12 (m, 2H), 3.60 (s, 2H), 7.10 (d, 1H), 7.33 (d, 1H), 7.40 (s, 1H), 9.50 (br s, 1H). APCI MS m/z 241 [MH]$^+$

Preparation 80: 8-Chloro-5-methyl-2-methylsulphanyl-3,4,5,6-tetrahydro-benzo[b][1,5]diazocine

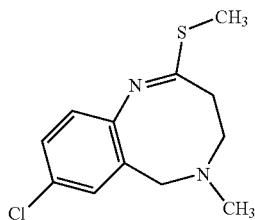

Potassium tert-butoxide (0.55 ml, 1M in tetrahydrofuran, 0.55 mmol) was added dropwise to a solution of the compound from preparation 79 (131 mg, 0.55 mmol) in tetrahydrofuran (2 ml), and the solution then stirred for 30 minutes. P-Methyl toluene sulphonate (102.4 mg, 0.55 mmol) was added and the reaction stirred at room temperature for 3 hours. The mixture was concentrated under reduced pressure and the residue partitioned between dichloromethane and water, and the layers separated. The organic phase was washed with brine, dried over magnesium sulphate and concentrated under reduced pressure to give the title compound (152 mg).

APCI MS m/z 255 [MH]$^+$

Preparation 81: (2-Amino-5-chloro-benzylamino)-acetic acid tert-butyl ester

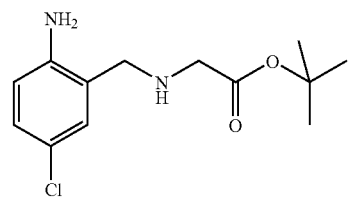

Chloro-acetic acid tert-butyl ester (500 mg, 3.34 mmol) was added to a solution of the amine of preparation 10 (1.04 g, 6.65 mmol) in THF (20 ml) and the reaction mixture was heated to 65° C. for 20 hours. The mixture was allowed to cool and was filtered. The filtrate was evaporated under reduced pressure and the resulting gummy residue was purified by column chromatography on silica gel using ethyl acetate to elute to give the title compound (726 mg) as a white crystalline solid.

$^1$H NMR (400 MHz, CD$_3$OD): δ 1.50 (s, 9H), 3.28 (s, 2H), 3.67 (s, 2H), 6.68 (d, 1H), 7.00 (d, 1H), 7.02 (s, 1H). APCI MS m/z 271 [MH]$^+$, 293 [MNa]$^+$

Preparation 82: 7-Chloro-1,3,4,5-tetrahydro-benzo[e][1,4]diazepin-2-one

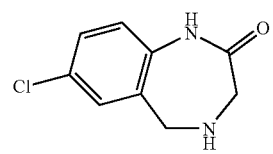

To a degassed solution of the ester of preparation 81 (49.2 g, 181.7 mmol) in THF (500 ml) was added potassium tert-butoxide (20.38 g, 181.6 mmol) and the mixture stirred at room temperature for 2 hours. A second addition of potassium tert-butoxide (2.04 g, 18.2 mmol) was made and stirring continued for 15 minutes before a saturated solution of ammonium chloride was added (150 ml). The resulting mixture was extracted with ethyl acetate (4 dm$^3$). The organic extracts were dried (MgSO$_4$) and filtered. The filtrate was evaporated under reduced pressure to give a yellow solid which was triturated twice with pentane (150 ml) and filtered to give the title compound as an off-white crystalline solid (31.1 g).

$^1$H NMR (400 MHz, CD$_3$OD): δ 3.54 (s, 2H), 3.92 (s, 2H), 7.02 (d, 1H), 7.25 (d, 1H), 7.27 (s, 1H).

Preparation 83: 7-Chloro-4-methyl-1,3,4,5-tetrahydro-benzo[e][1,4]diazepin-2-one

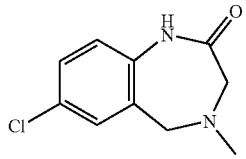

Formaldehyde (37% w/v aqueous, 5 ml, 60 mmol) was added to a suspension of the amine of preparation 82 (8.4 g, 42.7 mmol) in dichloromethane (140 ml) and acetic acid (1 ml). The mixture was stirred at room temperature for 0.25 hours before adding sodium triacetoxyborohydride (14 g, 64.1 mmol) portionwise, and it was stirred for a further 30 minutes. The reaction mixture was partitioned between 2N aqueous hydrochloric acid (50 ml) and dichloromethane (200 ml). The organic layer was extracted a second time with 2N aqueous hydrochloric acid (50 ml) before being discarded. The combined acid layers were made basic with 2N causing precipitation of a pale yellow solid, which was filtered off. The filtrate was extracted twice with dichloromethane (2×100 ml) and added to a solution of the pale yellow solid filter cake that had been dissolved in dichloromethane (500 ml). The combined dichloromethane layers were dried ($MgSO_4$), filtered and the filtrate evaporated under reduced pressure to give a yellow solid. Trituration with diethyl ether gave the title compound as a pale yellow solid (7.1 g).

$^1$H NMR (400 MHz, $CDCl_3$): δ 2.54 (s, 3H), 3.42 (s, 2H), 3.77 (s, 2H), 6.94 (d, 1H), 7.24 (m, 2H), 8.58 (s, 1H). APCI MS m/z 211 [MH]$^+$, 233 [MNa]$^+$

Preparation 84: 7-Chloro-4-methyl-1,3,4,5-tetrahydro-benzo[e][1,4]diazepine-2-thione

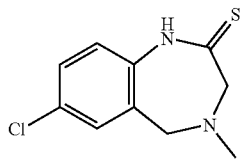

Sodium carbonate (1.06 g, 10 mmol) was added to a suspension of phosphorous pentasulphide (4.45 g, 10 mmol) in tetrahydrofuran (25 ml) at 5° C. The solution was cooled to 3° C., and the compound from preparation 83 (2.11 g, 10 mmol) was added. Water (1 ml) was added dropwise, and the resulting mixture was stirred at room temperature for 18 hours. The reaction was diluted with 0.88 ammonia (50 ml) and extracted with dichloromethane (2×200 ml). The combined organic extracts were washed with brine, dried over magnesium sulphate and evaporated under reduced pressure. The residue was purified by column chromatography on silica gel using ethyl acetate as eluant, to afford the title compound as a yellow solid (2.11 g)

$^1$H NMR (400 MHz, $CDCl_3$): δ 2.62 (s, 3H), 3.61 (s, 2H), 3.67 (s, 2H), 7.00 (d, 1H), 7.34 (m, 2H), 10.1 (s, 1H). APCI MS m/z 227 [MH]$^+$

Preparation 85: (5-Chloro-2-nitro-benzylsulfanyl)-acetic acid

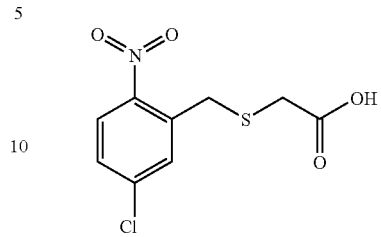

Mercapto-acetic acid (1.39 ml, 20 mmol) was dissolved in a 3.3 molar aqueous solution of sodium hydroxide (12 ml, 40 mmol) and cooled in an ice bath, before an acetone (50 ml) solution of 2-Bromomethyl-4-chloro-1-nitro-benzene (T. J. McCord et al, J. Het. Chem. 1972, 119-122) (5 g, 20 mmol) was added slowly. The resulting solution was stirred for 20 hours at room temperature before being diluted with water (50 ml) and extracted with dichloromethane (25 ml). The aqueous phase was made acidic with acetic acid and extracted with dichloromethane (2×25 ml). The combined organics were washed with brine, dried ($MgSO_4$), filtered and evaporated to give the title product as an off-white foam (3.65 g).

$^1$H NMR (400 MHz, $CDCl_3$): δ 3.15 (s, 2H), 4.20 (s, 2H), 7.40 (d, 1H), 7.50 (s, 1H), 8.00 (d, 1H), 11.85 (brs, 1H). APCI MS m/z 260 [MH]$^+$

Preparation 86: 2-Chloro-5,9-dihydro-8-thia-5-aza-benzocyclohepten-6-one

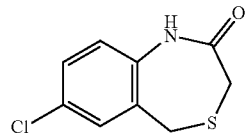

To a solution of the nitro compound of preparation 85 (2.59 g, 9,9 mmol) in ethanol (100 ml) was added platinum oxide (1 g). The mixture was hydrogenated at room temperature, under a pressure of 40 p.s.i. for 1 hour. The reaction mixture was allowed to cool before filtering through a plug of Arbocel®. The filtrate was evaporated and the residue suspended in xylene (50 ml) before heating to 150° C. for 20 hours. The mixture was allowed to cool and purified by column chromatography on silica gel using dichloromethane to elute, followed by ethyl acetate, to afford a buff solid which was triturated with diethyl ether to afford the title compound as a white solid (850 mg)

$^1$H NMR (400 MHz, $CDCl_3$): δ 3.05 (s, 2H), 3.80 (s, 2H), 7.00 (d, 1H), 7.30 (dd, 1H), 7.35 (s, 1H), 7.90 (s, 1H). APCI MS m/z 212 [MH]$^+$

Preparation 87: 2-Chloro-5,9-dihydro-8-thia-5-aza-benzocycloheptene-6-thione

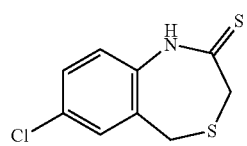

Sodium carbonate (394 mg, 3.7 mmol) was added to a suspension of phosphorous pentasulphide (1.65 g, 3.7 mmol) in tetrahydrofuran (20 ml) at 5° C. The solution was cooled to 3° C., and the compound from preparation 86 (750 mg, 3.5 mmol) was added. Water (4 drops) was added dropwise, and the resulting mixture stirred at room temperature for 18 hours. The reaction mixture was diluted with 0.880 ammonia (75 ml), and extracted with dichloromethane (2×35 ml). The combined organic extracts were washed with brine, dried over magnesium sulphate and evaporated under reduced pressure to afford the title compound as a white solid (603 mg).

$^1$H NMR (400 MHz, CDCl$_3$): δ 3.55 (s, 2H), 3.85 (s, 2H), 7.00 (dd, 1H), 7.35 (m, 2H), 9.20 (br s, 1H). APCI MS m/z 230 [MH]$^+$

Preparation 88:
2-amino-5-chloro-N-methylbenzamide

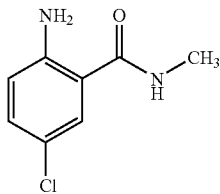

To a solution of 5-chloroisatoic anhydride (10.0 g, 51 mmol) in tetrahydrofuran (100 ml) at ambient temperature was added a 40% w/w aqueous solution of methylamine (19.80 g, 255 mmol) dropwise. The mixture was stirred at an ambient temperature for 1 hour. Ethyl acetate (100 ml) and water (100 ml) were added and the phases separated. The aqueous layer was back extracted with ethyl acetate (100 ml) and the combined organics were evaporated under reduced pressure to afford a white solid, which was recrystallised from toluene (60 ml) to afford the title compound as a white solid (8.15 g)

$^1$H NMR (400 MHz, CDCl$_3$): δ 2.86 (s, 3H), 6.71-6.73 (d, 1H), 7.11-7.14 (m, 1H), 7.41 (s, 1H)

Preparation 89:
(2-amino-5-chlorobenzyl)methylamine

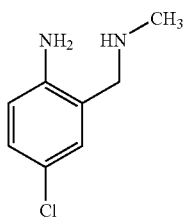

To a suspension of 2-amino-5-chloro-N-methylbenzamide (20.08 g, 109 mmol) and sodium borohydride (12.37 g, 327 mmol) in tetrahydrofuran (200 ml) was added boron trifluoride diethyl etherate, dropwise, at T<15° C. The mixture was stirred at an ambient temperature for 1 hour before heating to reflux for 6 hours. The reaction mixture was cooled in an ice water bath and a solution of piperazine (75.08 g, 872 mmol) in water (530 ml) was added dropwise. The mixture was then heated to reflux for 16 hours. The mixture was cooled to an ambient temperature and ethyl acetate (100 ml) was added. The phases were separated and the aqueous layer back extracted with ethyl acetate (40 ml). The combined organic phases were washed with water (3×80 ml) and evaporated under reduced pressure to afford an orange oil (17.58 g, 103 mmol)). The oil was dissolved in ethyl acetate (175 ml) and benzenesulfonic acid (16.29 g, 103 mmol) and stirred at an ambient temperature for 2 hours. The white precipitate was collected by filtration to afford the benzenesulfonate salt (24.12 g). The white solid was partitioned between dichloromethane (240 ml) and 2M sodium hydroxide (240 ml) and the phases were separated. The organic phase was evaporated under reduced pressure to afford the title compound as a colourless oil (10.78 g)

$^1$H NMR (400 MHz, CDCl$_3$): δ 2.42 (s, 3H), 3.72 (s, 2H), 6.55-6.57 (d, 1H), 7.00-7.04 (m, 2H)

Preparation 90: (2-amino-5-chlorobenzyl)methyl{[5-(1-pyridin-2-ylpiperidin-4-yl)-1,3,4-oxadiazol-2-yl]methyl}amine

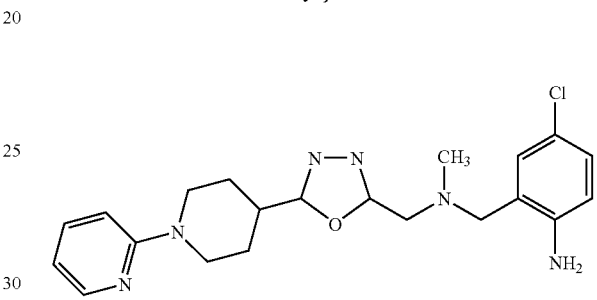

The oxadiazole of preparation 5b (2.77 g, 9.93 mmol) was heated at reflux with the amine of preparation 89 (2.53 g, 14.9 mmol) and sodium hydrogen carbonate (0.88 g, 10.43 mmol) in acetonitrile for 5 hours. The mixture was cooled and water (20 ml) and dichloromethane (20 ml) were added. The phases were separated and the organic phase was evaporated under reduced pressure to afford the title compound as an oil (4.8 g)

$^1$H NMR (400 MHz, CDCl$_3$): δ 1.91-2.01 (m, 2H), 2.16-2.20 (m, 2H), 2.33 (s, 3H), 3.07-3.21 (m, 3H), 3.57 (s, 2H), 3.79 (s, 2H), 4.29-4.33 (m, 2H), 6.55-6.57 (d, 1H), 6.62-6.65 (m, 1H), 6.69-6.71 (d, 1H), 6.98 (m, 1H), 7.03-7.05 (m, 1H), 7.47-7.51 (m, 1H), 8.19-8.20 (m, 1H)

Preparation 91: 8-Chloro-5-methyl-1-(3,4,5,6-tetrahydro-2H-[1,2']bipyridinyl-4-yl)-5,6-dihydro-4H-2,3,5,10b-tetraaza-benzo[e]azulene dibesylate

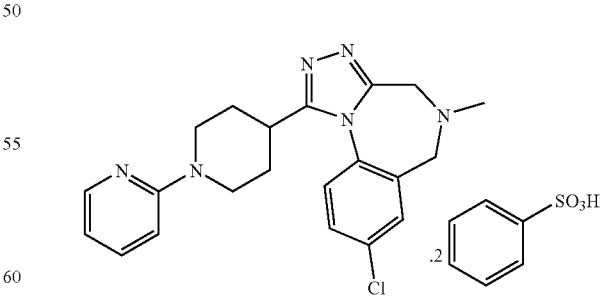

To a suspension of 8-Chloro-5-methyl-1-(3,4,5,6-tetrahydro-2H-[1,2']bipyridinyl-4-yl)-5,6-dihydro-4H-2,3,5,10b-tetraaza-benzo[e]azulene (25.3 g, 64 mmol) in methanol (250 ml) was added benzenesulfonic acid (20.3 g, 128 mmol). The yellow solution was heated to 60° C. for 1 hour and then allowed to cool to ambient temperature and stirred for 16 hours. The mixture was cooled in iced water for 1 hour before filtering under vacuum to afford a white granular solid which, after being dried at 50° C. under vacuum for 16 hours, afforded the title compound (41.3 g).

$^1$H NMR (400 MHz, D$_2$O): δ 1.62-1.82 (m, 2H), 2.04-2.20 (m, 1H), 2.31-2.43 (m, 1H), 2.98 (s, 3H), 3.08-3.23 (m, 1H), 3.30-3.43 (m, 1H), 3.44-3.54 (m, 1H), 3.84-4.02 (m, 2H), 4.02-4.13 (m, 1H), 4.13-4.27 (m, 1H), 4.27-4.40 (m, 1H), 6.81-6.90 (m, 1H), 7.17-7.19 (d, 1H), 7.40-7.54 (m, 6H), 7.62-7.73 (m, 5H), 7.73-7.82 (m, 3H), 7.82-7.94 (m, 1H); (Found C, 55.6; H, 5.0; N, 11.8%. C$_{33}$H$_{35}$ClN$_6$O$_6$S$_2$ requires C, 55.7; H, 5.0; N, 11.8%).

EXAMPLE 1

1-(3,4,5,6-Tetrahydro-2H-[1,2']bipyridinyl-4-yl)-5,6-dihydro-4H-2,3,5,10b-tetraaza-benzo[e]azulene

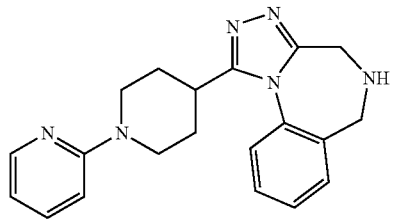

Toluene-4-sulfonic acid (100 mg, 0.58 mmol) was added to a solution of the oxadiazole of preparation 13 (2.45 g, 6.8 mmol) and heated to 150° C. for 18 hours. The mixture was cooled and purified by chromatography on silica gel using methanol and ammonium hydroxide in dichloromethane (5:0.5:95) as eluant, followed by chromatography on silica gel using methanol and ammonium hydroxide in ethyl acetate (10:1:90), followed by methanol and ammonium hydroxide in dichloromethane (7:1:93) as eluant to give, after trituration with ethyl acetate, the title compound (770 mg) as a brown solid.

APCI MS m/z 347 [MH]$^+$ $^1$H NMR (400 MHz, CDCl$_3$): δ 1.80-2.40 (m, 4H), 2.95 (m, 2H), 3.20 (m, 1H), 3.73 (s, 2H), 3.88 (s, 2H), 4.33 (m, 2H), 6.57 (m, 1H), 6.68 (d, 1H), 7.37 (d, 1H), 7.50 (m, 4H), 8.17 (d, 1H)

EXAMPLE 2

5-Methyl-1-(3,4,5,6-tetrahydro-2H-[1,2']bipyridinyl-4-yl)-5,6-dihydro-4H-2,3,5,10b-tetraaza-benzo[e]azulene

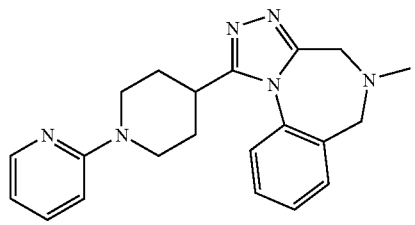

Formaldehyde (37% w/v aqueous, 1 ml, 81 mmol) was added to a solution of the amine of example 1 (100 mg, 0.28 mmol) in dichloromethane (20 ml). The mixture was stirred at room temperature for 0.25 hours before sodium triacetoxyborohydride (500 mg, 2.4 mmol) was added. The reaction mixture was stirred for a further 0.25 hours. The dichloromethane was removed under reduced pressure. The residue was partitioned between 2N aqueous sodium hydroxide solution (50 ml) and ethyl acetate (50 ml). The organic layer was washed with saturated brine and dried over magnesium sulphate before filtering and evaporating the filtrate under reduced pressure to give the title compound as a pale yellow foam (75 mg)

APCI MS m/z 361 [MH]$^+$, 384 [MNa]$^{+1}$H NMR (400 MHz, CDCl$_3$): δ 2.08 (m, 4H), 2.52 (s, 3H), 3.00 (m, 2H), 3.21 (m, 2H), 3.40 (s, 2H), 3.70 (s, 2H), 4.36 (m, 2H), 6.60 (m, 1H), 6.68 (d, 1H), 7.40 (d, 1H), 7.50 (m, 4H), 8.18 (d, 1H)

EXAMPLE 3

1-[1-(3,4,5,6-Tetrahydro-2H-[1,2']bipyridinyl-4-yl)-4H,6H-2,3,5,10b-tetraaza-benzo[e]azulen-5-yl]-ethanone

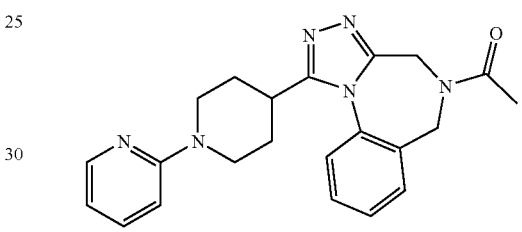

Acetyl chloride (22 mg, 0.29 mmol) was added to an ice cooled solution of the amine of example 1 (100 mg, 0.29 mmol) in dichloromethane (50 ml) and stirred at room temperature for 2 hours. The dichloromethane was evaporated off under reduced pressure and the residue purified by chromatography on silica gel using methanol and ammonium hydroxide in dichloromethane (5:0.5:95) as eluant to give the title compound as a brown foam (102 mg).

APCI MS m/z 389 [MH]$^+$, 412 [MNa]$^{+1}$H NMR (400 MHz, CDCl$_3$): δ 1.50-2.28 (m, 7H, rotamers), 3.01 (brs, 2H), 3.10 (m, 1H), 4.00-5.00 (m, 6H, rotamers), 6.61 (m, 1H), 6.68 (m, 1H), 7.50 (m, 3H), 7.61 (m, 2H), 8.18 (m, 1H)

EXAMPLE 4

8-Chloro-1-(3,4,5,6-tetrahydro-2H-[1,2']bipyridinyl-4-yl)-5,6-dihydro-4H-2,3,5,10b-tetraaza-benzo[e]azulene

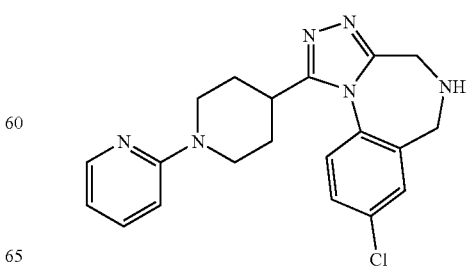

Toluene-4-sulfonic acid (100 mg, 0.58 mmol) was added to a solution of the oxadiazole of preparation 14 (4.65 g, 12 mmol) and heated to 140° C. for 18 hours. The mixture was cooled and purified by chromatography on silica gel using methanol and ammonium hydroxide in dichloromethane (5:0.5:95) as eluant to give the title compound (2.0 g) as an off-white solid.

APCI MS m/z 381 [MH]$^+$, 403 [MNa]$^{+1}$H NMR (400 MHz, CDCl$_3$): δ 1.80-2.20 (m, 4H), 2.95 (m, 2H), 3.14 (m, 1H), 3.68 (s, 2H), 3.92 (s, 2H), 4.36 (m, 2H), 6.60 (m, 1H), 6.67 (d, 1H), 7.35 (d, 1H), 7.50 (m, 3H), 8.17 (d, 1H) Found; C, 59.90; H, 5.48; N, 20.50; C$_{20}$H$_{21}$N$_6$Cl 0.33CH$_2$Cl$_2$ requires; C, 59.72; H, 5.34; N, 20.55%.

EXAMPLE 4b

8-Chloro-1-(3,4,5,6-tetrahydro-2H-[1,2']bipyridinyl-4-yl)-5,6-dihydro-4H-2,3,5,10b-tetraaza-benzo[e]azulene

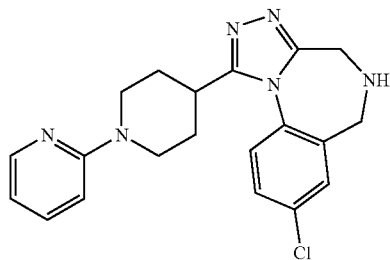

Trifluoroacetic acid (2.9 ml, 38 mmol) was added to a tetrahydrofuran solution of the oxadiazole of preparation 14b (10 g, 25 mmol) and heated to 65-67° C. for 6 hours. The reaction mixture was cooled and adjusted to pH 7 with sodium hydroxide (5M) before vacuum distillation to ethyl acetate. The reaction mixture was then adjusted to pH 10 with further sodium hydroxide (5M) followed by cooling to 10° C. for 1 hour. The product was isolated by filtration and then reslurried in water before re-filtering. The product, a white solid, was dried under vacuum (7.75 g).

APCI MS m/z 381 [MH]$^+$, 403 [MNa]$^{+1}$H NMR (400 MHz, CDCl$_3$): δ 1.80-2.20 (m, 4H), 2.95 (m, 2H), 3.14 (m, 1H), 3.68 (s, 2H), 3.92 (s, 2H), 4.36 (m, 2H), 6.60 (m, 1H), 6.67 (d, 1H), 7.35 (d, 1H), 7.50 (m, 3H), 8.17 (d, 1H) Found; C, 59.90; H, 5.48; N, 20.50; C$_{20}$H$_{21}$N$_6$Cl 0.33CH$_2$Cl$_2$ requires; C, 59.72; H, 5.34; N, 20.55%.

EXAMPLE 5

8-Chloro-5-methyl-1-(3,4,5,6-tetrahydro-2H-[1,2']bipyridinyl-4-yl)-5,6-dihydro-4H-2,3,5,10b-tetraaza-benzo[e]azulene trihydrochloride

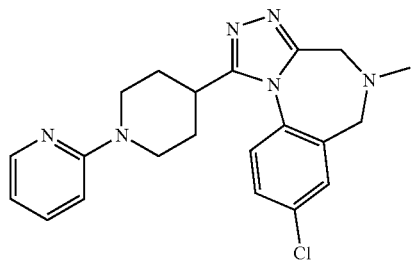

Formaldehyde (37% w/v aqueous, 0.1 ml, 1.2 mmol) was added to a solution of the amine of example 4 (200 mg, 0.53 mmol) in dichloromethane (5 ml). The mixture was stirred at room temperature for 0.25 hours before sodium triacetoxyborohydride (500 mg, 2.4 mmol) was added, and the reaction mixture was stirred for a further 18 hours. The reaction mixture was partitioned between 2N aqueous sodium hydroxide solution (10 ml) and dichloromethane (10 ml). The organic layer was evaporated under reduced pressure and purified by chromatography on silica gel using methanol in dichloromethane (5:95) as eluant. The residue was dissolved in dichloromethane (2 ml) and hydrochloric acid (1M in diethyl ether, 2 ml) was added. The solvent was evaporated under reduced pressure to give the title compound as a brown foam (96 mg).

APCI MS m/z 395 [MH]$^+$, 417 [MNa]$^{+1}$H NMR (400 MHz, CD$_3$OD): δ 2.00 (m, 2H), 2.27 (m, 1H), 2.58 (m, 1H), 3.11 (s, 3H), 3.36 (m, 1H), 3.62 (m, 2H), 4.21 (m, 4H), 4.40 (m, 1H), 4.55 (m, 1H), 7.00 (t, 1H), 7.44 (d, 1H), 7.88 (m, 2H), 7.92 (m, 2H), 8.06 (t, 1H) Found; C, 44.30; H, 5.52; N, 14.65; C$_{21}$H$_{23}$N$_6$Cl 0.33CH$_2$Cl$_2$. 3HCl. 2.5H$_2$O requires; C, 44.37; H, 5.53; N, 14.53%.

EXAMPLE 5b

8-Chloro-5-methyl-1-(3,4,5,6-tetrahydro-2H-[1,2']bipyridinyl-4-yl)-5,6-dihydro-4H-2,3,5,10b-tetraaza-benzo[e]azulene

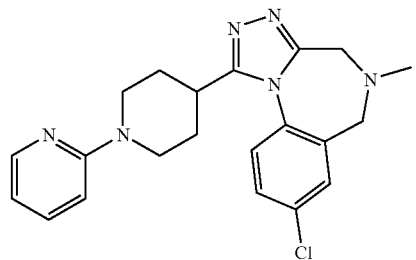

To a solution of the thioamide of preparation 84 (80 mg, 0.35 mmol) in butan-1-ol was added the hydrazide of preparation 1 (78 mg, 0.35 mmol) and the mixture was heated to 100° C. for 20 hours. The reaction mixture was evaporated under reduced pressure and the residue was purified by column chromatography on silica gel using dichloromethane:Methanol:0.880 ammonia (90:10:1) as eluant, to afford the title compound as a brown foam (90 mg).

$^1$H NMR (400 MHz, CDCl$_3$): δ 2.00 (m, 4H), 2.45 (s, 3H), 3.96 (t, 2H), 3.15 (m, 1H), 3.36 (m, 1H), 3.64 (m, 2H), 4.36 (m, 2H), 6.58 (m, 1H), 6.65 (d, 1H), 7.32 (d, 1H), 7.46 (t, 1H), 7.52 (m, 2H), 8.18 (t, 1H) APCI MS m/z 395 [MH]$^+$, 417 [Mna]$^+$

EXAMPLE 5c

8-Chloro-5-methyl-1-(3,4,5,6-tetrahydro-2H-[1,2']
bipyridinyl-4-yl)-5,6-dihydro-4H-2,3,5,10b-tetraaza-
benzo[e]azulene trihydrochloride

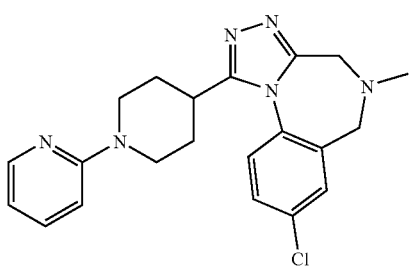

Acetic acid (3 ml, 52 mmol) was added to a solution of the amine of example 4b (10 g, 26 mmol) in dichloromethane (100 ml) followed by formaldehyde (37% w/v aqueous, 3.2 ml, 39 mmol). In a separate vessel sodium triacetoxyborohydride (6.7 g, 31 mmol) was slurried in dichloromethane and cooled to <10° C. The imine solution was then added dropwise to the cold slurry over 15 minutes. The reaction mixture was stirred at room temperature for 0.5 hours, after which time the reaction mixture was partitioned between 2N aqueous sodium hydroxide solution and dichloromethane. The organic phase was then washed three times with a 50% aqueous solution of sodium metabisulfite, followed by a final water wash. The dichloromethane solution was distilled to half volume before adding EtOAc and further distilled to remove the remaining dichloromethane. EtOH was added and the reaction mixture heated for a further 0.5 hours, before cooling to 10° C. and isolating the product as a white solid. The solid was dried under vacuum at 50° C. for 16 hours to afford the title compound (7.48 g).

APCI MS m/z 395 [MH]$^+$, 417 [MNa]$^{+1}$H NMR (400 MHz, CD$_3$OD): δ 2.00 (m, 2H), 2.27 (m, 1H), 2.58 (m, 1H), 3.11 (s, 3H), 3.36 (m, 1H), 3.62 (m, 2H), 4.21 (m, 4H), 4.40 (m, 1H), 4.55 (m, 1H), 7.00 (t, 1H), 7.44 (d, 1H), 7.88 (m, 2H), 7.92 (m, 2H), 8.06 (t, 1H) Found; C, 44.30; H, 5.52; N, 14.65; C$_{21}$H$_{23}$N$_6$Cl 0.33CH$_2$Cl$_2$.3HCl.2.5H$_2$O requires; C, 44.37; H, 5.53; N, 14.53%.

EXAMPLE 6

8-Chloro-5-isopropyl-1-(3,4,5,6-tetrahydro-2H-[1,2']
bipyridinyl-4-yl)-5,6-dihydro-4H-2,3,5,10b-tetraaza-
benzo[e]azulene trihydrochloride

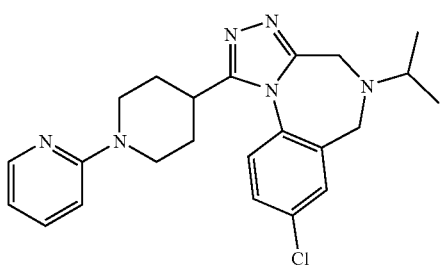

Acetone (0.1 ml, 1.36 mmol) was added to a solution of the amine of example 4 (200 mg, 0.53 mmol) in dichloromethane (5 ml). The mixture was stirred at room temperature for 0.25 hours before sodium triacetoxyborohydride (500 mg, 2.4 mmol) was added, and the reaction mixture stirred for a further 18 hours. The reaction mixture was partitioned between 2N aqueous sodium hydroxide solution (10 ml) and dichloromethane (10 ml). The organic layer was evaporated under reduced pressure and purified by chromatography on silica gel using methanol in dichloromethane (5:95) as eluant. The residue was dissolved in dichloromethane (2 ml) and hydrochloric acid (1M in diethyl ether, 2 ml) was added. The solvent was evaporated under reduced pressure to give the title compound as a brown foam (161 mg).

APCI MS m/z 423 [MH]$^+$, 445 [MNa]$^{+1}$H NMR (400 MHz, CD$_3$OD): δ 1.57 (m, 6H), 2.00 (m, 2H), 2.24 (m, 1H), 2.58 (m, 1H), 3.38 (m, 1H), 3.58 (m, 1H), 3.70 (m, 1H), 3.86 (m, 1H), 4.23 (m, 3H), 4.40 (m, 1H), 4.62 (m, 1H), 5.00 (m, 1H), 7.00 (m, 1H), 7.43 (m, 1H), 7.80-8.06 (m, 5H) Found; C, 46.51; H, 5.98; N, 13.96; C$_{23}$H$_{27}$N$_6$Cl 0.28CH$_2$Cl$_2$.3HCl.2.5H$_2$O requires; C, 46.51; H, 5.96; N, 13.98%.

EXAMPLE 7

8-Chloro-1-(3,4,5,6-tetrahydro-2H-[1,2']bipyridinyl-
4-yl)-5-(tetrahydro-pyran-4-yl)-5,6-dihydro-4H-2,3,
5,10b-tetraaza-benzo[e]azulene

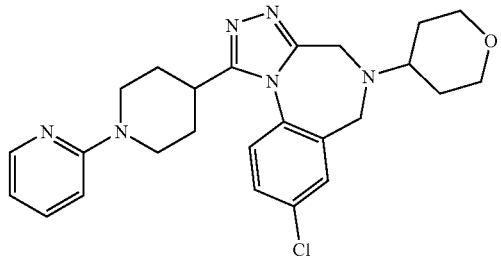

Tetrahydro-pyran-4-one (68 mg, 0.68 mmol) was added to a solution of the amine of example 4 (130 mg, 0.34 mmol) in dichloromethane (5 ml). The mixture was stirred at room temperature for 0.25 hours before sodium triacetoxyborohydride (217 mg, 1.0 mmol) was added, and the reaction mixture was stirred for a further 18 hours. Further tetrahydro-pyran-4-one (68 mg, 0.68 mmol) and sodium triacetoxyborohydride (217 mg, 1.0 mmol) were added and the reaction mixture was heated to 40° C. for 24 hours. The reaction mixture was partitioned between 2N aqueous sodium carbonate solution (10 ml) and ethyl acetate (50 ml). The organic layer was washed three times with 2N aqueous sodium carbonate solution (10 ml), once with saturated aqueous brine, and then dried over magnesium sulphate before filtering and evaporating the filtrate under reduced pressure. The residue was purified by chromatography on silica gel using a gradient of ethyl acetate in pentane (0% to 30%) as eluant, followed by chromatography on silica gel using a gradient of methanol in dichloromethane (0% to 5%) as eluant, to afford the title compound as a brown foam (80 mg).

APCI MS m/z 465 [MH]$^+$, 487 [MNa]$^{+1}$H NMR (400 MHz, CDCl$_3$): δ 1.57-175 (m, 4H), 1.75-2.20 (m, 6H), 2.72 (m, 1H), 2.98 (t, 2H), 3.16 (m, 1H), 3.39 (t, 2H), 3.40-3.60 (m, 2H), 3.60-4.10 (m, 2H), 4.02 (d, 2H), 4.34 (d, 2H), 6.61 (dd, 1H), 6.69 (d, 1H), 7.33 (d, 1H), 7.45-7.59 (m, 3H), 8.17 (d, 1H).

EXAMPLE 8

1-[8-Chloro-1-(3,4,5,6-tetrahydro-2H-[1,2']bipyridinyl-4-yl)-4H,6H-2,3,5,10b-tetraaza-benzo[e]azulen-5-yl]-ethanone dihydrochloride

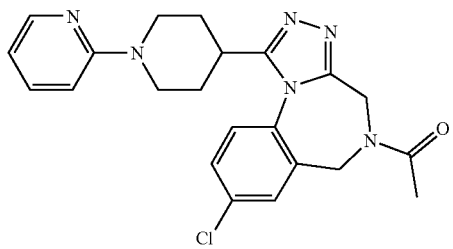

Acetyl chloride (0.1 ml, 1.4 mmol) was added to an ice cooled solution of the amine of example 4 (200 mg, 0.53 mmol) in dichloromethane (5 ml) and stirred at room temperature for 20 hours. Dichloromethane was evaporated off under reduced pressure and the residue purified by chromatography on silica gel using methanol in dichloromethane (5:95) as eluant. The residue was dissolved in dichloromethane (2 ml) and hydrochloric acid (1M in diethyl ether, 2 ml) was added, and the solvents evaporated under reduced pressure to give the title compound as a brown foam (110 mg).

ESI MS m/z 423 [M+H]$^{+1}$H NMR (400 MHz, CD$_3$OD): δ 1.95-2.40 (m, 7H, rotamers), 3.40-3.55 (m, 2H), 3.80 (m, 1H), 4.20-4.90 (m, 4H, rotamers), 4.82 (s, 2H), 7.02 (t, 1H), 7.46 (d, 1H), 7.80 (m, 1H), 7.91 (t, 1H), 7.95-8.00 (m, 2H), 8.07 (t, 1H) Found C, 45.94%, H, 5.77%, N, 14.35%; C$_{22}$H$_{23}$ClN$_6$O.2HCl.0.40CH$_2$Cl$_2$.3.07H$_2$O requires C, 45.98%, H, 5.50%, 14.36%

EXAMPLE 9

[8-Chloro-1-(3,4,5,6-tetrahydro-2H-[1,2']bipyridinyl-4-yl)-4H,6H-2,3,5,10b-tetraaza-benzo[e]azulen-5-yl]-cyclopropyl-methanone dihydrochloride

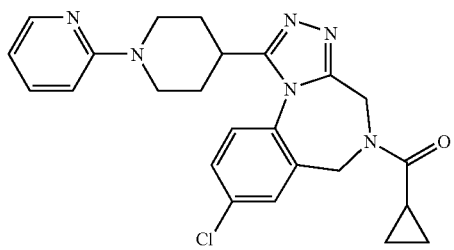

The title compound was prepared from Cyclopropanecarbonyl chloride and the amine of example 4, in 50% yield, using the procedure described in example 8.

ESI MS m/z 449 [M+H]$^{+1}$H NMR (400 MHz, CD$_3$OD): δ 0.83-1.00 (m, 4H), 1.80-2.50 (m, 4H, rotamers), 3.40-3.60 (m, 2H), 3.89 (bt, 1H), 4.20-5.0 (m, 3H, rotamers), 4.86 (s, 2H), 7.04 (t, 1H), 7.26 (d, 1H), 7.82 (bd, 1H), 7.90-8.00 (m, 3H), 8.08 (t, 1H)

EXAMPLE 10

1-[8-Chloro-1-(3,4,5,6-tetrahydro-2H-[1,2']bipyridinyl-4-yl)-4H,6H-2,3,5,10b-tetraaza-benzo[e]azulen-5-yl]-2,2-dimethyl-propan-1-one dihydrochloride

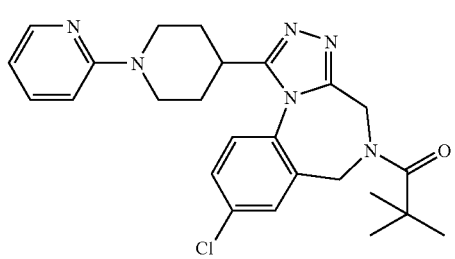

The title compound was prepared from 2,2-Dimethyl-propionyl chloride and the amine of example 4, in 54% yield, using the procedure described in example 8.

APCI MS m/z 465 [M+H]$^{+1}$H NMR (400 MHz, CD$_3$OD): δ 1.40 (s, 9H), 1.80-2.60 (m, 4H, rotamers), 3.40-3.60 (m, 2H), 3.88 (bt, 1H), 4.10-5.00 (m, 4H, rotamers), 4.85 (s, 2H), 7.04 (t, 1H), 7.47 (d, 1H), 7.80-7.86 (m, 2H), 7.94 (d, 1H), 7.99 (d, 1H), 8.08 (t, 1H)

EXAMPLE 11

8-Chloro-5-methanesulfonyl-1-(3,4,5,6-tetrahydro-2H-[1,2']bipyridinyl-4-yl)-5,6-dihydro-4H-2,3,5,10b-tetraaza-benzo[e]azulene

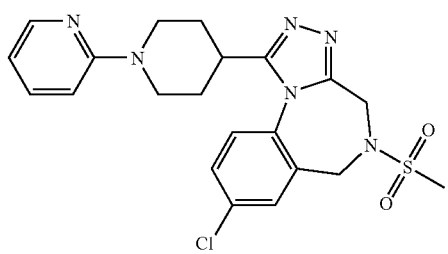

Methanesulfonyl chloride (0.1 ml, 1.29 mmol) was added to an ice cooled solution of the amine of example 4 (200 mg, 0.53 mmol) in dichloromethane (5 ml) and stirred at room temperature for 20 hours. The dichloromethane was evaporated off under reduced pressure and the residue purified by chromatography on silica gel using methanol in dichloromethane (5:95) as eluant, to afford the title compound as a brown foam (71 mg).

APCI MS m/z 459 [M+H]$^+$, 481 [M+Na]$^{+Found\ C,}$ 52.98%, H, 5.05%, N, 17.20%; C$_{21}$H$_{23}$ClN$_6$O$_2$S.0.25CH$_2$Cl$_2$ requires C, 53.15%, H, 4.93%, 17.50%

EXAMPLE 12

8-Chloro-1-(1-pyrimidin-2-yl-piperidin-4-yl)-5,6-dihydro-4H-2,3,5,10b-tetraaza-benzo[e]azulene

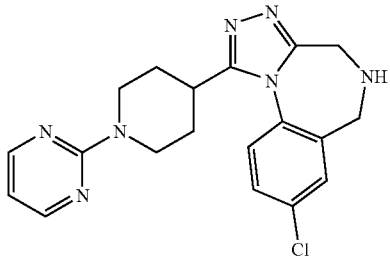

Toluene-4-sulfonic acid (5 mg, 0.03 mmol) was added to a solution of the oxadiazole of preparation 15 (2.34 g, 5.9 mmol) and heated to 140° C. for 18 hours. The mixture was cooled and purified by chromatography on silica gel using methanol and ammonium hydroxide in dichloromethane (5:0.5:95) as eluant to afford the title compound (1.12 g) as an off-white solid.

ESI MS m/z 382 [M+H]$^{+1}$H NMR (400 MHz, CDCl$_3$): δ 1.60-2.20 (m, 4H), 2.95 (bt, 2H), 3.10 (m, 1H), 3.63 (s, 2H), 3.70-4.00 (m, 2H), 4.75 (d, 2H), 6.43 (t, 1H), 7.26 (d, 1H), 7.40-7.52 (m, 2H), 8.22 (d, 2H) Found C, 57.24%, H, 5.31%, N, 24.10%; C$_{19}$H$_{20}$ClN$_7$.0.25CH$_2$Cl$_2$ requires C, 57.36%, H, 5.13%, 24.32%

EXAMPLE 13

8-Chloro-5-methyl-1-(1-pyrimidin-2-yl-piperidin-4-yl)-5,6-dihydro-4H-2,3,5,10b-tetraaza-benzo[e]azulene

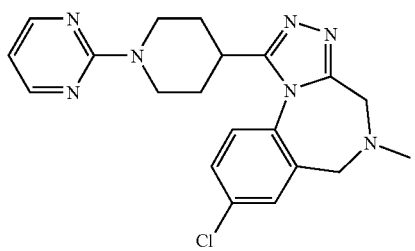

Formaldehyde (37% w/v aqueous, 0.1 ml, 1.2 mmol) was added to a solution of the amine of example 12 (100 mg, 0.26 mmol) in dichloromethane (5 ml). The mixture was stirred at room temperature for 0.25 hours before sodium triacetoxyborohydride (111 mg, 0.53 mmol) was added, and the reaction mixture was stirred for a further 18 hours. The mixture was partitioned between 2N aqueous sodium hydroxide solution (10 ml) and dichloromethane (10 ml). The organic layer was evaporated under reduced pressure and purified by chromatography on silica gel using methanol in dichloromethane (5:95) as eluant to afford the title compound as a brown foam (66 mg).

ESI MS m/z 382 [M+Na]$^{+1}$H NMR (400 MHz, CDCl$_3$): δ 1.50-2.20 (m, 4H), 2.45 (s, 3H), 2.98 (bt, 2H), 3.10 (bt, 1H), 3.20-3.90 (m, 3H), 4.77 (s, 2H), 6.45 (s, 1H), 7.32 (d, 1H), 7.46-7.53 (m, 2H), 8.26 (d, 2H) Found C, 59.12%, H, 5.50%, N, 24.00%; C$_{20}$H$_{22}$ClN$_7$.0.15CH$_2$Cl$_2$ requires C, 59.23%, H, 5.66%, N, 23.99%

EXAMPLE 14

8-Chloro-5-isopropyl-1-(1-pyrimidin-2-yl-piperidin-4-yl)-5,6-dihydro-4H-2,3,5,10b-tetraaza-benzo[e]azulene

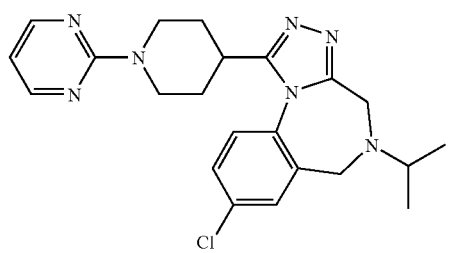

The title compound was prepared from acetone and the amine of example 12, in 65% yield, using the procedure described in example 13.

ESI MS m/z 382 [M+H]$^{+1}$H NMR (400 MHz, CDCl$_3$): δ 1.20 (d, 6H), 1.60-2.10 (m, 4H), 2.90-3.07 (m, 3H), 3.18 (t, 1H), 3.30-4.00 (m, 4H), 4.78 (d, 2H), 6.47 (t, 1H), 7.29 (d, 1H), 7.48-7.58 (m, 2H), 8.30 (d, 2H) Found C, 60.55%, H, 6.24%, N, 21.73%; C$_{22}$H$_{26}$ClN$_7$.0.22CH$_2$Cl$_2$ requires C, 60.17%, H, 6.03%, N, 22.11%.

EXAMPLE 15

8-Chloro-5-methanesulfonyl-1-(1-pyrimidin-2-yl-piperidin-4-yl)-5,6-dihydro-4H-2,3,5,10b-tetraaza-benzo[e]azulene

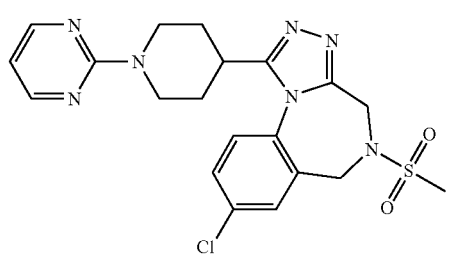

The title compound was prepared from the amine of example 12, in 69% yield, using the procedure described in example 11.

APCI MS m/z 460 [M+H]$^+$, 482 [M+Na]$^{+1}$H NMR (400 MHz, CDCl$_3$): δ 1.40-2.40 (m, 6H), 2.95 (s, 3H), 2.90-4.20 (m, 5H), 4.40-5.30 (m, 4H), 6.52 (t, 1H), 7.40 (d, 1H), 7.60-7.70 (m, 2H), 8.32 (d, 2H)

EXAMPLE 16

[8-Chloro-1-(1-pyrimidin-2-yl-piperidin-4-yl)-4H,6H-2,3,5,10b-tetraaza-benzo[e]azulen-5-yl]-cyclopropyl-methanone

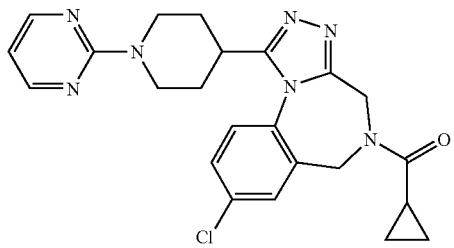

The title compound was prepared as an off-white foam from cyclopropanecarbonyl chloride and the amine of example 12, in 69% yield, using the procedure described in example 3.

APCI MS m/z 472 [M+Na]$^{+1}$H NMR (400 MHz, CDCl$_3$): δ 0.86 (m, 2H), 1.04 (m, 2H), 1.40-2.40 (m, 6H), 2.70-3.20 (m, 3H), 4.40-5.80 (m, 5H), 6.61 (t, 1H), 7.39 (d, 1H), 7.52-7.65 (m, 2H), 8.32 (d, 2H)

EXAMPLE 17

1-[8-Chloro-1-(1-pyrimidin-2-yl-piperidin-4-yl)-4H,6H-2,3,5,10b-tetraaza-benzo[e]azulen-5-yl]-2,2-dimethyl-propan-1-one

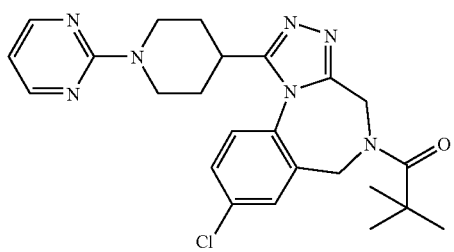

The title compound was prepared from 2,2-Dimethyl-propionyl chloride and the amine of example 12, in 42% yield, using the procedure described in example 3.

APCI MS m/z 466 [M+H]$^{+1}$H NMR (400 MHz, CDCl$_3$): δ 1.38 (s, 9H), 1.40-2.40 (m, 7H), 2.90-3.10 (m, 2H), 3.17 (m, 1H), 4.60-5.00 (m, 2H), 5.27 (s, 2H), 6.58 (t, 1H), 7.35 (d, 1H), 7.54-7.68 (m, 2H), 8.29 (d, 1H)

EXAMPLE 18

1-[8-Chloro-1-(1-pyrimidin-2-yl-piperidin-4-yl)-4H,6H-2,3,5,10b-tetraaza-benzo[e]azulen-5-yl]-ethanone

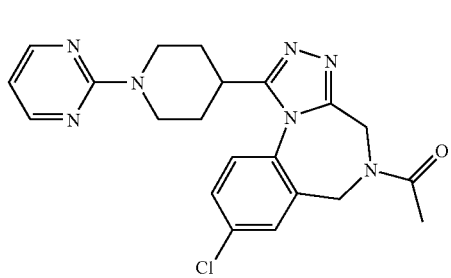

The title compound was prepared from acetyl chloride and the amine of example 12, in 37% yield, using the procedure described in example 3.

APCI MS m/z 424 [M+H]$^{+1}$H NMR (400 MHz, CDCl$_3$): δ 1.40-2.50 (m, 10H), 2.70-3.30 (m, 4H), 4.70-4.90 (m, 2H), 6.52 (t, 1H), 7.38 (d, 1H), 7.54-7.64 (m, 2H), 8.33 (d, 2H)

EXAMPLE 19

8-Chloro-1-(6'-trifluoromethyl-3,4,5,6-tetrahydro-2H-[1,2']bipyridinyl-4-yl)-4H,6H-5-oxa-2,3,10b-triaza-benzo[e]azulene

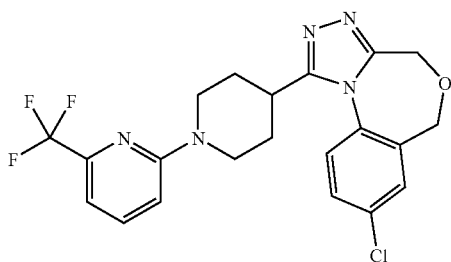

2-Chloro-6-trifluoromethyl-pyridine (55 mg, 0.30 mmol) and potassium carbonate (41 mg, 0.30 mmol) were added to a solution of the amine of preparation 29 (45 mg, 0.15 mmol) in N,N-dimethylformamide (2 ml). The mixture was heated at 100° C. for 18 hours before evaporation under reduced pressure. The residue was purified by chromatography on silica gel using methanol and ammonium hydroxide in dichloromethane (5:0.5:95) as eluant to afford the title compound (30 mg), as a brown foam.

APCI MS m/z 450 [M+H]$^+$, 472 [M+Na]$^{+1}$H NMR (400 MHz, CD$_3$OD): δ 1.88-2.06 (m, 4H), 3.01 (bt, 2H), 3.40 (m, 1H), 4.44 (bs, 2H), 4.51 (d, 2H), 4.59 (s, 2H), 6.94 (d, 1H), 7.02 (d, 1H), 7.68 (t, 1H), 7.74-7.78 (m, 4H).

EXAMPLE 20

4-(8-Chloro-4H,6H-5-oxa-2,3,10b-triaza-benzo[e]
azulen-1-yl)-3,4,5,6-tetrahydro-2H-[1,2']bipyridinyl-
6'-carbonitrile

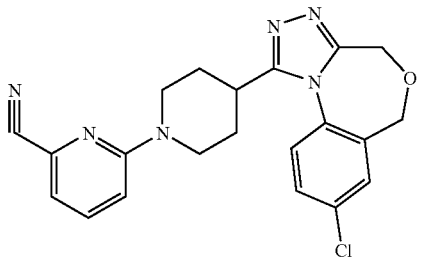

The title compound was prepared from 6-Chloro-pyridine-2-carbonitrile and the amine of preparation 29, in 61% yield, using the procedure described in example 19.

APCI MS m/z 407 [M+H]$^+$, 429 [M+Na]$^{+1}$H NMR (400 MHz, CD$_3$OD): δ 1.86-2.08 (m, 4H), 3.03 (bt, 2H), 3.44 (m, 1H), 4.46 (m, 4H), 4.59 (s, 2H), 7.03 (d, 1H), 7.11 (d, 1H), 7.62 (dd, 1H), 7.72-7.78 (, 3H) Found C, 61.31%, H, 4.73%, N, 20.38%; C$_{21}$H$_{19}$ClN$_6$O.0.25H$_2$O requires C, 61.31%, H, 4.78%, N, 20.43%

EXAMPLE 21

4-(8-Chloro-4H,6H-5-oxa-2,3,10b-triaza-benzo[e]
azulen-1-yl)-3,4,5,6-tetrahydro-2H-[1,2']bipyridinyl-
6'-carboxylic acid amide

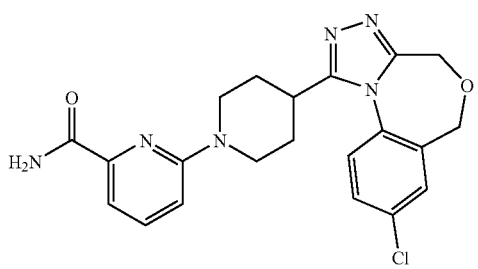

Powdered potassium hydroxide (46 mg, 81 mmol) was added to a solution of the carbonitrile of example 20 (110 mg, 0.27 mmol) in 2-Methyl-propan-2-ol (6 ml). The mixture was heated at 100° C. for 18 hours before evaporation under reduced pressure. The residue was purified by chromatography on silica gel using methanol and ammonium hydroxide in dichloromethane (5:0.5:95) as eluant, to afford the title compound (62 mg), as an off-white solid.

APCI MS m/z 425 [M+H]$^+$, 447 [M+Na]$^{+1}$H NMR (400 MHz, CD$_3$OD): δ 1.89-2.07 (m, 4H), 3.01 (bt, 2H), 3.42 (m, 1H), 4.45 (s, 2H), 4.52 (bd, 2H), 4.60 (s, 2H), 7.02 (d, 1H), 7.38 (d, 1H), 7.67 (dd, 1H), 7.72-7.78 (m, 4H)

EXAMPLE 22

13-Chloro-3-(3,4,5,6-tetrahydro-2H-[1,2']bipyridinyl-4-yl)-2,4,5,8-tetraaza-tricyclo[9.4.0.0*2,6*]pentadeca-1(11),3,5,12,14-pentaene

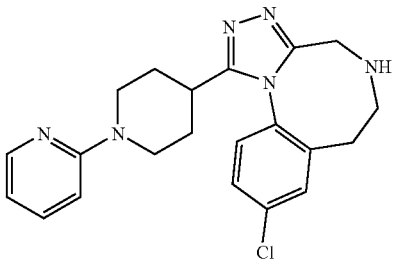

Toluene-4-sulfonic acid (50 mg, 0.3 mmol) was added to a solution of the oxadiazole of preparation 41 (1.35 g, 3.3 mmol) and heated to 140° C. for 2 hours. The mixture was cooled and purified by chromatography on silica gel using ethyl acetate followed by methanol and ammonium hydroxide in dichloromethane (5:0.5:95) as eluant, to afford the title compound (273 mg) as an off-white solid.

APCI MS m/z 398 [M+H]$^{+1}$H NMR (400 MHz, CDCl$_3$): δ 1.42 (bd, 1H), 1.65 (dq, 1H), 2.05 (dt, 1H), 2.16 (bd, 1H), 2.32 (dq, 1H), 2.63-2.77 (m, 2H), 2.79-2.94 (m, 2H), 2.95 (m, 1H), 3.10 (d, 1H), 3.46 (dt, 1H), 4.18 (bd, 1H), 4.38 (bd, 1H), 4.41 (d, 1H), 6.59 (dd, 1H), 6.65 (d, 1H), 7.18 (d, 1H), 7.38-7.42 (m, 2H), 7.57 (t, 1H), 8.17 (d, 1H) Found C, 62.41%, H, 5.98%, N, 20.45%; C$_{21}$H$_{23}$ClN$_6$.0.12CH$_2$Cl$_2$ requires C, 62.72%, H, 5.78%, N, 20.75%

EXAMPLE 23

1-[13-Chloro-3-(3,4,5,6-tetrahydro-2H-[1,2']bipyridinyl-4-yl)-2,4,5,8-tetraaza-tricyclo[9.4.0.0*2,6*]
pentadeca-1(11),3,5,12,14-pentaen-8-yl]-ethanone

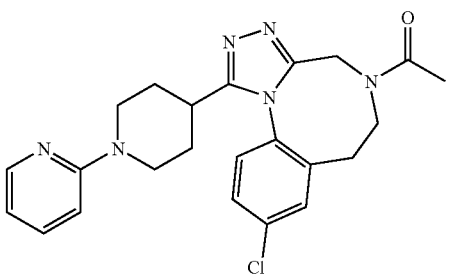

Acetic anhydride (35 □l, 0.37 mmol) was added to a solution of the amine of example 22 (120 mg, 0.30 mmol) and triethylamine in dichloromethane (5 ml) and stirred at room temperature for 2 hours. The dichloromethane was evaporated off under reduced pressure and the residue was purified by chromatography on silica gel using methanol and ammonium hydroxide in dichloromethane (5:0.5:95) as eluant, to afford the title compound as a white solid (120 mg).

APCI MS m/z 437 [M+H]$^+$, 459 [M+Na]$^{+1}$H NMR (400 MHz, CDCl$_3$): δ 1.44 (bd, 1H), 1.63 (m, 1H), 2.16 (m, 2H), 2.10-2.22 (m, 2H), 2.28 (dt, 1H), 2.44 (s, 3H), 2.63-2.80 (m, 2H), 2.83-3.05 (m, 3H), 3.66 (d, 1H), 4.15 (bd, 1H), 4.41 (bd, 1H), 4.94 (dd, 1H), 5.06 (d, 1H), 6.59 (t, 1H), 6.63 (d, 1H), 7.17 (d, 1H), 7.38-7.50 (m, 3H), 8.14 (d, 1H) Found C, 61.92%, H, 5.93%, N, 18.38%; $C_{21}H_{23}ClN_6 \cdot 0.60H_2O$ requires C, 61.70, H, 5.90%, N, 18.77%

EXAMPLE 24

13-Chloro-8-methyl-3-(3,4,5,6-tetrahydro-2H-[1,2']bipyridinyl-4-yl)-2,4,5,8-tetraaza-tricyclo[9.4.0.0*2,6*]pentadeca-1(11),3,5,12,14-pentaene

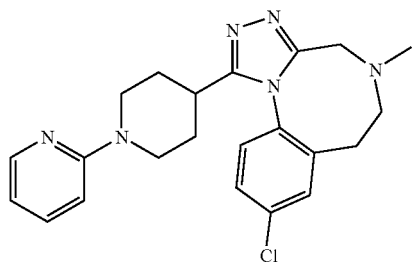

The title compound was prepared from the amine of example 22, in 78% yield, using the procedure described in example 2.

APCI MS m/z 409 [M+H]$^+$, 431 [M+Na]$^+$ $^1$H NMR (400 MHz, CDCl$_3$): δ 1.41 (bd, 1H), 1.62 (dq, 1H), 2.14 (bd, 1H), 2.23-2.32 (m, 2H), 2.37 (s, 3H), 2.55 (dd, 1H), 2.66-2.78 (m, 2H), 2.88 (m, 1H), 2.96 (dt, 1H), 3.20 (d, 1H), 3.26 (dd, 1H), 4.15 (d, 2H), 4.35 (bd, 1H), 6.55 (dd, 1H), 6.62 (d, 1H), 7.14 (d, 1H), 7.32-7.39 (m, 2H), 7.41 (t, 1H), 8.12 (d, 1H)

EXAMPLE 25

3-(1-Pyrimidin-2-yl-piperidin-4-yl)-8-oxa-2,4,5-triaza-tricyclo[9.4.0.0*2,6*]pentadeca-1(11),3,5,12,14-pentaene

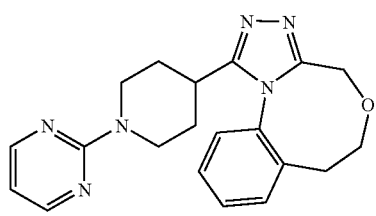

The title compound was prepared from the oxadiazole of preparation 24, in 50% yield, using the procedure described in example 22.

ESI MS m/z 364 [M+H]$^+$ $^1$H NMR (400 MHz, CDCl$_3$): δ 1.48 (bd, 1H), 1.65 (dq, 1H), 2.20 (bd, 1H), 2.31 (dq, 1H), 2.44 (m, 1H), 2.83-2.95 (m, 2H), 3.01 (m, 1H), 3.11 (dt, 1H), 3.50 (q, 1H), 3.92 (d, 1H), 4.26 (m, 1H), 4.60 (d, 1H), 4.92 (d, 1H), 5.08 (d, 1H), 6.50 (t, 1H), 7.24 (t, 1H), 7.40 (t, 1H), 7.46 (d, 1H), 7.53 (t, 1H), 8.32 (d, 2H)

EXAMPLE 26

8-Chloro-1-(1-pyrimidin-2-yl-piperidin-4-yl)-4H,6H-5-oxa-2,3,10b-triaza-benzo[e]azulene

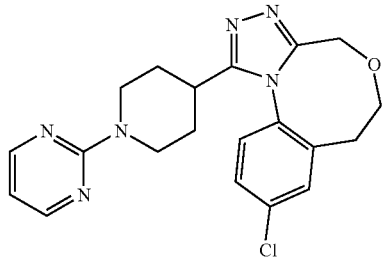

The title compound was prepared from the oxadiazole of preparation 23, in 70% yield, using the procedure described in example 22.

ESI MS m/z 383 [M+H]+$^1$H NMR (400 MHz, CDCl$_3$): δ 1.92-2.13 (m, 4H), 3.07 (t, 2H), 3.12 (m, 1H), 4.39 (s, 2H), 4.66 (s, 2H), 4.82 (m, 2H), 6.53 (t, 1H), 7.39 (d, 1H), 7.57-7.63 (m, 2H), 8.33 (d, 2H)

EXAMPLE 27

13-Chloro-3-(3,4,5,6-tetrahydro-2H-[1,2']bipyridinyl-4-yl)-8-oxa-2,4,5-triaza-tricyclo[9.4.0.0*2,6*]pentadeca-1(11),3,5,12,14-pentaene

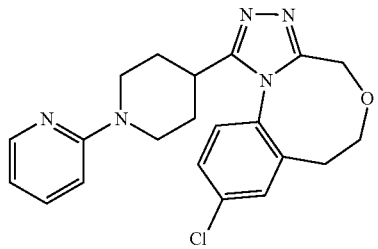

The title compound was prepared from the oxadiazole of preparation 22, in 40% yield, using the procedure described in example 22.

APCI MS m/z 396 [M+H]$^+$ $^1$H NMR (400 MHz, CDCl$_3$): δ 1.44 (bd, 1H), 1.66 (dq, 1H), 2.17 (bd, 1H), 2.36 (dq, 1H), 2.43 (m, 1H), 2.72-2.85 (m, 2H), 2.89-3.03 (m, 2H), 3.55 (t, 1H), 3.97 (d, 1H), 4.14-4.26 (m, 2H), 4.40 (bd, 1H), 5.07 (d, 1H), 6.59 (dd, 1H), 6.64 (d, 1H), 7.19 (d, 1H), 7.38-7.48 (m, 3H), 8.15 (d, 1H) Found C, 62.84%, H, 5.54%, N, 17.34%; $C_{21}H_{22}ClN_5O \cdot 0.08CH_2Cl_2$ requires C, 62.88%, H, 5.55%, N, 17.39%.

EXAMPLE 28

3-(3,4,5,6-Tetrahydro-2H-[1,2']bipyridinyl-4-yl)-8-oxa-2,4,5-triaza-tricyclo[9.4.0.0*2,6*]pentadeca-1(11),3,5,12,14-pentaene dihydrochloride

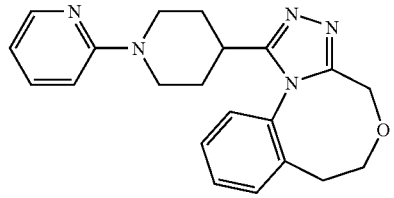

The title compound was prepared from the oxadiazole of preparation 21, in 49% yield, using the procedure described in example 22. The dihydrochloride salt was prepared using the procedure described in example 8.

APCI MS m/z 362 [M+H]$^{+1}$H NMR (400 MHz, CD$_3$OD): δ 1.67-1.81 (m, 2H), 2.32 (dq, 1H), 2.47-2.57 (m, 2H), 3.11 (dd, 1H), 3.25 (dt, 1H), 3.33 (m, 2H), 3.45-3.62 (m, 3H), 4.07-4.16 (m, 2H), 4.30 (m, 1H), 4.40 (bd, 1H), 5.07 (d, 1H), 7.00 (t, 1H), 7.40 (d, 1H), 7.60-7.66 (m, 2H), 7.69-7.78 (m, 2H), 7.96 (d, 1H), 8.06 (t, 1H).

EXAMPLE 29

8-Chloro-1-(3,4,5,6-tetrahydro-2H-[1,2']bipyridinyl-4-yl)-4H,6H-5-oxa-2,3,10b-triaza-benzo[e]azulene

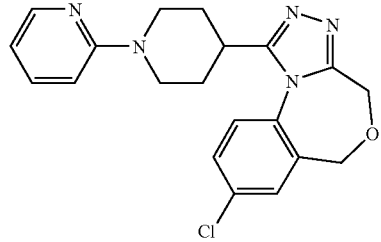

The title compound was prepared from the oxadiazole of preparation 20, in 60% yield, using the procedure described in example 22.

APCI MS m/z 382 [M+H]$^{+1}$H NMR (400 MHz, CDCl$_3$): δ 1.97 (bd, 2H), 2.09 (m, 2H), 2.98 (dt, 2H), 3.17 (m, 1H), 4.32-4.40 (m, 4H), 4.64 (s, 2H), 6.59 (dd, 1H), 6.64 (d, 1H), 7.39 (d, 1H), 7.45 (t, 1H), 7.56-7.61 (m, 2H), 8.17 (d, 1H). Found C, 60.19%, H, 5.17%, N, 17.31%; C$_2$,H$_{22}$ClN$_5$O.0.27CH$_2$Cl$_2$ requires C, 60.14%, H, 5.11%, N, 17.30%

EXAMPLE 30

7-Chloro-1-(3,4,5,6-tetrahydro-2H-[1,2']bipyridinyl-4-yl)-4H,6H-5-oxa-2,3,10b-triaza-benzo[e]azulene dihydrochloride

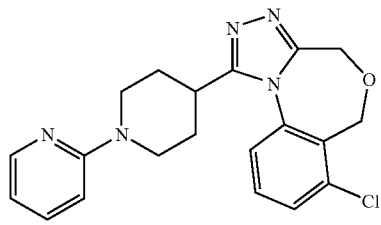

The title compound was prepared from the oxadiazole of preparation 17, in 21% yield, using the procedure described in example 22. The dihydrochloride salt was prepared using the procedure described in example 8.

APCI MS m/z 382 [M+H]$^{+1}$H NMR (400 MHz, CD$_3$OD): δ 2.10 (m, 2H), 2.30 (m, 2H), 3.50 (bt, 2H), 3.74 (m, 1H), 4.32 (m, 2H), 4.93 (s, 2H), 7.00 (t, 1H), 7.46 (d, 1H), 7.77-7.95 (m, 3H), 8.00 (dd, 1H), 8.09 (t, 1H).

EXAMPLE 31

1-(3,4,5,6-Tetrahydro-2H-[1,2']bipyridinyl-4-yl)-4H,6H-5-oxa-2,3,10b-triaza-benzo[e]azulene

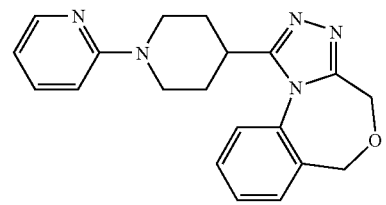

The title compound was prepared from the oxadiazole of preparation 16, in 41% yield, using the procedure described in example 22.

APCI MS m/z 348 [M+H]$^{+1}$H NMR (400 MHz, CDCl$_3$): δ 1.98 (bd, 2H), 2.12 (m, 2H), 2.97 (t, 2H), 3.24 (m, 1H), 4.35 (d, 2H), 4.45 (s, 2H), 4.65 (s, 2H), 6.59 (dd, 1H), 6.69 (d, 1H), 7.38-7.49 (m, 2H), 7.53-7.65 (m, 3H), 8.18 (d, 1H) Found C, 64.55%, H, 5.84%, N, 17.92%; C$_{20}$H$_{21}$N$_5$O.0.40CH$_2$Cl$_2$.0.08C$_8$H$_{10}$ requires C, 64.82%, H, 5.84%, N, 17.96%

EXAMPLE 32

8-Methoxy-1-(3,4,5,6-tetrahydro-2H-[1,2']bipyridinyl-4-yl)-4H,6H-5-oxa-2,3,10b-triaza-benzo[e]azulene dihydrochloride

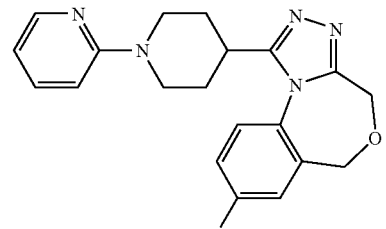

The title compound was prepared from the oxadiazole of preparation 19, in 68% yield, using the procedure described in example 22. The dihydrochloride salt was prepared using the procedure described in example 8.

ESI MS m/z 379 [M+H]$^{+1}$H NMR (400 MHz, CD$_3$OD): δ 2.08 (bq, 2H), 2.30 (bd, 2H), 3.49 (t, 2H), 3.85 (m, 1H), 3.95 (s, 3H), 4.32 (bd, 2H), 4.59 (s, 2H), 4.68 (s, 2H), 7.03 (t, 1H), 7.31-7.35 (m, 2H), 7.45 (d, 1H), 7.80, (d, 1H), 7.97(d, 1H), 8.08 (t, 1H).

EXAMPLE 33

8-Fluoro-1-(3,4,5,6-tetrahydro-2H-[1,2']bipyridinyl-4-yl)-4H,6H-5-oxa-2,3,10b-triaza-benzo[e]azulene

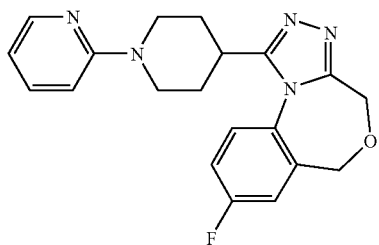

The title compound was prepared from the oxadiazole of preparation 31, in 62% yield, using the procedure described in example 22.

APCI MS m/z 366 [M+H]$^{+1}$H NMR (400 MHz, CDCl$_3$): δ 1.90-2.16 (m, 4H), 2.97 (dt, 2H), 3.16 (m, 1H), 4.28-4.40 (m, 4H), 4.63 (s, 2H), 6.58 (dd, 1H), 6.66 (d, 1H), 7.24-7.35 (m, 2H), 7.40-7.52 (m, 2H), 8.15 (d, 1H) Found C, 64.47%, H, 5.56%, N, 18.50%; C$_{20}$H$_{20}$FN$_5$O.0.07CH$_2$Cl$_2$.0.07EtOAc requires C, 64.74%, H, 5.53%, N, 18.55%.

EXAMPLE 34

8,9-Difluoro-1-(3,4,5,6-tetrahydro-2H-[1,2']bipyridinyl-4-yl)-4H,6H-5-oxa-2,3,10b-triaza-benzo[e]azulene dihydrochloride

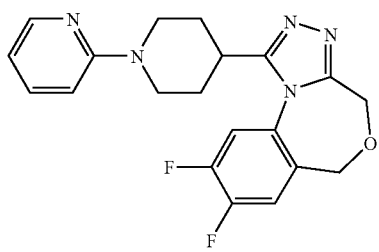

The title compound was prepared from the oxadiazole of preparation 33, in 44% yield, using the procedure described in example 22. The dihydrochloride salt was prepared using the procedure described in example 8.

APCI MS m/z 384 [M+H]$^{+1}$H NMR (400 MHz, CD$_3$OD): δ 2.00-2.13 (m, 2H), 2.18-2.37 (m, 2H), 3.52 (dt, 2H), 4.33 (bd, 2H), 4.58 (s, 2H), 4.68 (s, 2H), 7.02 (t, 1H), 7.47 (d, 1H), 7.81 (dd, 1H), 7.94-8.02 (m, 2H), 8.06 (t, 1H) Found C, 49.58%, H, 5.01%, N, 14.25%; C$_{20}$H$_{19}$F$_2$N$_5$O$_1$.2HCl.0.30CH$_2$Cl$_2$.0.58H$_2$O requires C, 49.53%, H, 4.66%, N, 14.23%

EXAMPLE 35

9-Chloro-1-(3,4,5,6-tetrahydro-2H-[1,2']bipyridinyl-4-yl)-4H,6H-5-oxa-2,3,10b-triaza-benzo[e]azulene dihydrochloride

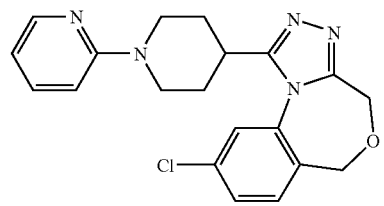

The title compound was prepared from the oxadiazole of preparation 18, in 54% yield, using the procedure described in example 22. The dihydrochloride salt was prepared using the procedure described in example 8.

APCI MS m/z 383 [M+H]$^{+1}$H NMR (400 MHz, CD$_3$OD): δ 2.10 (m, 2H), 2.35 (m, 2H), 3.55 (dt, 2H), 4.00 (bd, 1H), 4.35 (m, 2H), 4.65 (s, 2H), 4.80 (s, 2H), 7.02 (m, 1H), 7.45 (m, 1H), 7.81 (s, 2H), 8.00 (m, 3H)

EXAMPLE 36

1-(3,4,5,6-Tetrahydro-2H-[1,2']bipyridinyl-4-yl)-8-trifluoromethoxy-4H,6H-5-oxa-2,3,10b-triaza-benzo[e]azulene

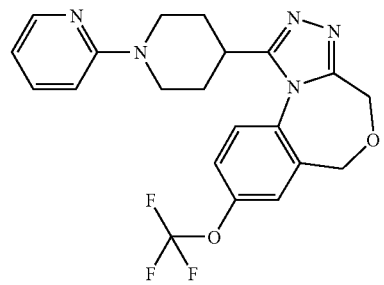

The title compound was prepared from the oxadiazole of preparation 36, in 44% yield, using the procedure described in example 22.

APCI MS m/z 432 [M+H]$^{+1}$H NMR (400 MHz, CDCl$_3$): δ 1.99 (m, 2H), 2.13 (m, 2H), 3.00 (dt, 2H), 3.17 (m, 1H), 4.37 (d, 2H), 4.42 (s, 2H), 4.66 (s, 2H), 6.60 (dd, 1H), 6.68 (d, 1H), 7.40-7.52 (m, 4H), 8.16 (d, 1H) Found C, 58.16%, H, 4.77%, N, 15.84%; C$_{21}$H$_{20}$F$_3$N$_5$O$_2$ requires C, 58.47%, H, 4.67%, N, 16.23%

EXAMPLE 37

8-Methyl-1-(3,4,5,6-tetrahydro-2H-[1,2']bipyridinyl-4-yl)-4H,6H-5-oxa-2,3,10b-triaza-benzo[e]azulene

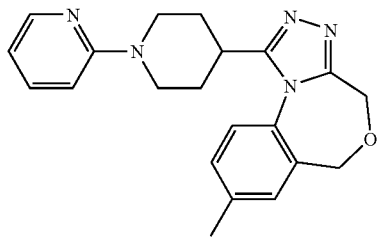

The title compound was prepared from the oxadiazole of preparation 37, in 48% yield, using the procedure described in example 22.

APCI MS m/z 362 [M+H]$^{+1}$H NMR (400 MHz, CDCl$_3$): δ 1.99 (m, 4H), 2.43 (m, 3H), 2.96 (dt, 2H), 3.41 (m, 1H), 4.34 (d, 2H), 4.42 (s, 2H), 4.66 (brs, 2H), 6.62 (dd, 1H), 6.83 (d, 1H), 7.44-7.60 (m, 3H), 7.63 (d, 1H), 8.06 (d, 1H)

EXAMPLE 38

1-[8-Chloro-1-(3,4,5,6-tetrahydro-2H-[1,2']bipyridinyl-4-yl)-4H,6H-2,3,5,10b-tetraaza-benzo[e]azulen-5-yl]-2-dimethylamino-ethanone

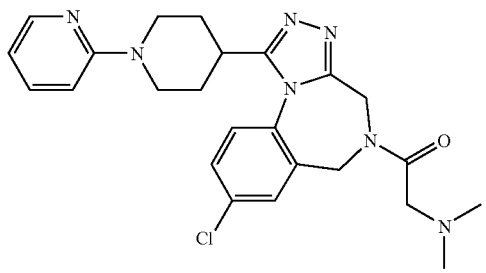

A solution of HBTU (152 mg, 0.38 mmol) in N,N-dimethylacetamide (1.9 ml) was added to a solution of the amine of example 4 (97 mg, 0.26 mmol), triethylamine (1.5 μl, cat.) and dimethylamino-acetic acid (36 mg, 0.26 mmol) in N,N-dimethylacetamide (2.5 ml) and heated to 50° C. for 2 hours. The mixture was cooled and the solvent evaporated under reduced pressure. The residue was partitioned between dichloromethane (10 ml) and 2M aqueous sodium hydroxide solution (10 ml). The organic phase was dried over magnesium sulphate before being evaporated under reduced pressure and purified by chromatography on silica gel using methanol and ammonium hydroxide in dichloromethane (7:1:93) as eluant to afford the title compound (70 mg) as a brown foam.

APCI MS m/z 466 [M+H]$^{+Found}$ C, 60.14%, H, 5.93%, N, 20.29%; C$_{24}$H$_{28}$ClN$_7$O.2HCl.0.20CH$_2$Cl$_2$ requires C, 60.18%, H, 5.93%, N, 20.30%

EXAMPLE 39

2-Chloro-1-[8-chloro-1-(3,4,5,6-tetrahydro-2H-[1,2']bipyridinyl-4-yl)-4H,6H-2,3,5,10b-tetraaza-benzo[e]azulen-5-yl]-ethanone

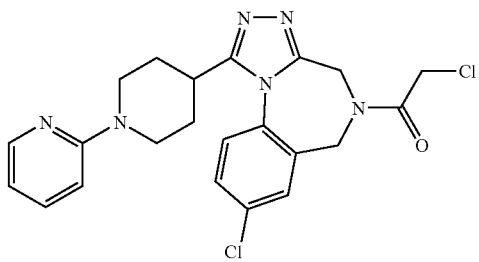

Triethylamine (1.37 ml, 9.81 mmol) and chloroacetyl chloride (0.35 ml, 4.35 mmol) were added to a solution of the amine from example 4 (1.5 g, 3.95 mmol) in dichloromethane (50 ml), and the reaction stirred at room temperature for 2 hours. TLC analysis showed starting material remained, so additional chloroacetyl chloride (0.35 ml, 4.35 mmol) was added and the reaction was stirred for an additional 1.5 hours. The mixture was partitioned between dichloromethane and 2N sodium hydroxide solution and the layers separated. The aqueous phase was extracted with further dichloromethane and the combined organic solutions were washed with brine (50 ml), dried over magnesium sulphate, and evaporated under reduced pressure. The residual foam was purified by column chromatography on silica gel using dichloromethane:methanol:0.88 ammonia (95:5:0.5) to afford the title compound as a foam, 1.12 g.

$^1$H NMR (400 MHz, CDCl$_3$): δ 1.30-2.60 (m, 4H), 2.84-3.20 (m, 3H), 3.40-4.80 (m, 8H), 6.62 (m, 1H), 6.70 (m, 1H), 7.40 (m, 1H), 7.50 (m, 1H), 7.61 (m, 2H), 8.18 (m, 1H). APCI MS m/z 457 [MH]$^+$

Microanalysis found: C, 55.13; H, 4.81; N, 17.19. C$_{22}$H$_{22}$Cl$_2$N$_6$O; 0.33CH$_2$Cl$_2$ requires C, 55.26; H, 4.71; N, 17.31%.

EXAMPLE 40

2-Azetidin-1-yl-1-[8-chloro-1-(3,4,5,6-tetrahydro-2H-[1,2']bipyridinyl-4-yl)-4H,6H-2,3,5,10b-tetraaza-benzo[e]azulen-5-yl]-ethanone

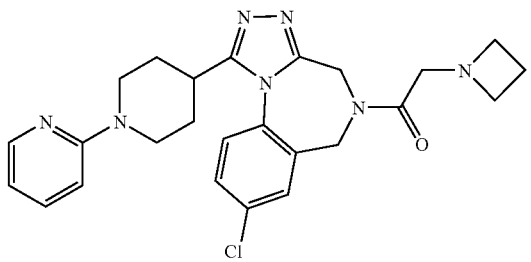

Potassium carbonate (227 mg, 1.65 mmol) and azetidine (0.06 ml, 0.82 mmol) were added to a solution of the chloro compound from example 39 (250 mg, 0.55 mol) in N,N-dimethylformamide (5 ml) and the reaction mixture stirred at 70° C. for 18 hours. The reaction was concentrated under reduced pressure and the residue was partitioned between water (10 ml) and ethyl acetate (10 ml), and the layers separated. The aqueous phase was extracted with ethyl acetate (2×10 ml). The combined organic solutions were washed with water (20 ml) and brine (10 ml), then dried over magnesium sulphate and evaporated under reduced pressure. The crude product was purified by column chromatography on silica gel using dichloromethane:methanol:0.88 ammonia (95:5:0.5) to afford the title compound as a white foam, 55 mg.

$^1$H NMR (400 MHz, CDCl$_3$): δ 1.68-2.30 (m, 6H), 2.80-3.90 (m, 11H), 4.10-4.50 (m, 2H), 5.10-5.55 (m, 2H), 6.60 (dd, 1H), 6.66 (d, 1H), 7.40 (dd, 1H), 7.45 (m, 1H), 7.58 (m, 2H), 8.18 (d, 1H). APCI MS m/z 478 [MH]$^+$

Microanalysis found: C, 60.26; H, 5.83; N, 19.55. C$_{25}$H$_{28}$ClN$_7$O; 0.33CH$_2$Cl$_2$ requires C, 60.12; H, 5.71; N, 19.38%.

EXAMPLE 41

1-[8-Chloro-1-(3,4,5,6-tetrahydro-2H-[1,2']bipyridinyl-4-yl)-4H,6H-2,3,5,10b-tetraaza-benzo[e]azulen-5-yl]-2-pyrrolidin-1-yl-ethanone

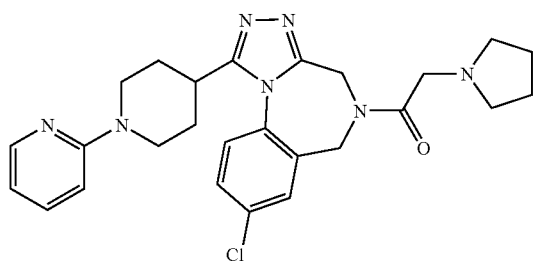

The title compound was obtained as a pale yellow foam from the chloro compound from example 39 and pyrrolidine, following the procedure described in example 40.

$^1$H NMR (400 MHz, CDCl$_3$): δ 1.54-2.01 (m, 8H), 2.05-4.00 (m, 11H), 4.20-4.45 (m, 2H), 5.10-5.58 (m, 2H), 6.60 (m, 1H), 6.66 (d, 1H), 7.40 (dd, 1H), 7.44 (m, 1H), 7.56-7.74 (m, 2H), 8.18 (d, 1H). APCI MS m/z 492 [MH]$^+$

EXAMPLE 42

[8-Chloro-1-(3,4,5,6-tetrahydro-2H-[1,2']bipyridinyl-4-yl)-4H,6H-2,3,5,10b-tetraaza-benzo[e]azulen-5-yl]-pyrrolidin-3-yl-methanone trihydrochloride

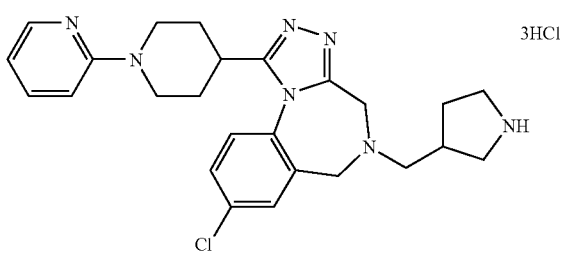

A solution of hydrochloric acid in dioxan (2.98 ml, 4M) was added to a solution of the protected amine from preparation 65 (690 mg, 1.10 mmol) in dichloromethane (5 ml), and the reaction mixture was stirred at room temperature for 1 hour. The mixture was evaporated under reduced pressure to give the title compound as a white solid (744 mg).

$^1$H NMR (400 MHz, CD$_3$OD): δ 2.00-2.22 (m 3H), 2.56 (m, 1H), 3.38-4.01 (m, 14H), 4.24-4.41 (m, 2H), 7.02 (m, 1H), 7.45 (d, 1H), 7.80 (m, 1H), 7.90-8.00 (m, 2H), 8.00-8.10 (m, 2H). APCI MS m/z 478 [MH]$^+$

EXAMPLES 43 TO 49

The following compounds of general structure:

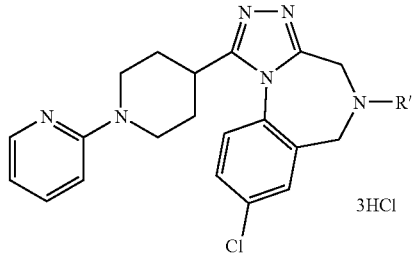

were prepared quantitatively from the appropriate protected amines following the procedure described in example 42.

| Ex No | R$^1$ | Form | Data |
|---|---|---|---|
| 43 | 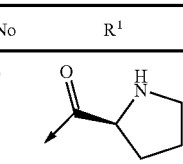 | Solid | $^1$H NMR (400 MHz, CD$_3$OD):δ 1.88-2.70 (m, 8H), 3.38-3.83 (m, 6H), 4.50-5.63 (m, 6H), 7.02 (DD, 1H), 7.45 (d, 1H), 7.81 (m, 2H), 7.90 (m, 1H), 7.98 (d, 1H), 8.07 (m, 1H) APCI MS m/z 478 [M-H]$^+$ |
| 44 | 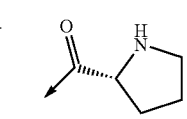 | Solid | $^1$H NMR (400 MHz, CD$_3$OD):δ 1.80-2.80 (m, 8H), 3.22-3.78 (m, 6H), 3.82-5.12 (m, 6H), 7.01 (m, 1H), 7.42 (d, 1H), 7.80 (m, 2H), 7.98 (d, 1H), 8.05 (m, 1H). APCI MS m/z 478 [M-H]$^+$ |
| 45 | 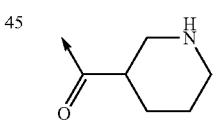 | Solid | APCI MS m/z 577 [M-H]$^-$ |

-continued

| Ex No | R¹ | Form | Data |
|---|---|---|---|
| 46 | | White solid | ¹H NMR (400 MHz, CD₃OD): δ 1.40-2.06 (m, 10H), 3.38-3.83 (m, 6H), 3.90-5.60 (m, 6H), 7.02 (m, 1H), 7.45 (m, 1H), 7.79-8.18 (m, 5H). APCI MS m/z 491 [M-H]⁻ |
| 47 | | White solid | ¹H NMR (400 MHz, CD₃OD): δ 1.40-2.07 (m, 10H), 3.04-4.75 (m, 12H), 7.00 (m, 1H), 7.46 (m, 1H), 7.80-8.18 (m, 5H). APCI MS m/z 491 [M-H]⁻ |
| 48 | | White solid | ¹H NMR (400 MHz, CD₃OD): δ 196-2.37 (m, 3H), 2.62 (m, 1H), 3.36-3.70 (m, 7H), 3.79-3.98 (m, 2H), 4.08 (m, 1H), 4.20-4.66 (m, 4H), 5.04-5.62 (m, 2H), 7.02 (dd, 1H), 7.48 (d, 1H), 7.82 (m, 1H), 7.98 (m, 1H). APCI MS m/z 494 [M-H]⁺ |
| 49 | | White solid | ¹H NMR (400 MHz, CD₃OD): δ 1.40-2.40 (m, 4H), 3.20-3.78 (m, 10H), 3.96-5.41 (m, 6H), 7.00 (m, 1H), 7.41 (d, 1H), 7.74-7.80 (m, 2H), 7.95 (d, 1H), 8.02 (m, 1H). APCI MS m/z 516 [MNa]⁻ |

EXAMPLE 50

8-Chloro-5-pyrrolidin-(2S)-2-ylmethyl-1-(3,4,5,6-tetrahydro-2H-[1,2']bipyridinyl-4-yl)-5,6-dihydro-4H-2,3,5,10b-tetraaza-benzo[e]azulene

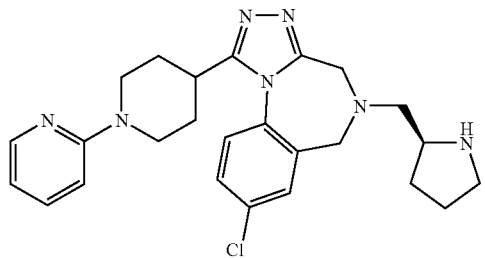

Borane (1M solution in tetrahydrofuran, 7.25 ml, 7.25 mmol) was added to a suspension of the amide from example 43 (398 mg, 0.725 mmol) in tetrahydrofuran (10 ml), and the mixture was heated under reflux for 2 hours. Hydrochloric acid (6M) was added until no more gas was evolved, and the reaction mixture was heated under reflux for a further 3 hours. The cooled mixture was basified using 2 N sodium hydroxide solution, and then extracted with ethyl acetate (×2). The combined organic extracts were washed with brine, dried over magnesium sulphate, and evaporated under reduced pressure. The colourless gum was purified by column chromatography on silica gel using dichloromethane:methanol:0.88 ammonia (80:20:3) as eluant, to afford the title compound as a white foam, 98 mg.

¹H NMR (400 MHz, CDCl₃): δ 1.39 (m, 1H), 1.59-2.18 (m, 7H), 2.58 (m, 2H), 2.80-3.76 (m, 10H), 4.23 (m, 2H), 6.50 (dd, 1H), 6.58 (d, 1H), 7.22 (d, 1H), 7.36-7.58 (m, 3H), 8.04 (d, 1H). APCI MS m/z 464 [MH]⁺

EXAMPLES 51 TO 54

The following compounds of general structure:

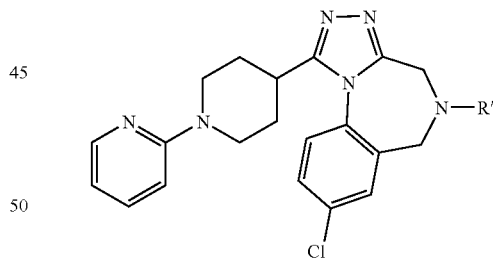

were prepared from the appropriate amides following the procedure described in example 50.

| Ex No | R¹ | Yield (%)/Form | Data |
|---|---|---|---|
| 51 | | 56 white foam | ¹H NMR (400 MHz, CDCl₃): δ 1.05-2.23 (m, 10H), 2.40-2.70 (m, 3H), 2.96 (m, 2H), 3.12 (m, 2H), 3.27-3.90 (m, 5H), 4.34 (m, 2H), 6.58 (dd, 1H), 6.66 (d, 1H), 7.33 (d, 1H), 7.45 (m, 3H), 8.18 (m, 1H). APCI MS m/z 478 [MH]⁺ |

-continued

| Ex No | R¹ | Yield (%)/Form | Data |
|---|---|---|---|
| 52 | | 63 white foam | ¹H NMR (400 MHz, CDCl₃): δ 1.05-2.05 (m, 10H), 2.40-2.70 (m, 3H), 2.97 (m, 2H), 3.10 (m, 2H), 3.10-4.40 (m, 7H), 6.60 (dd, 1H), 6.66 (d, 1H), 7.35 (d, 1H), 7.50 (m, 3H), 8.18 (d, 1H). APCI MS m/z 478 [MH]⁺ |
| 53 | | 24 white foam | ¹H NMR (400 MHz, CDCl₃): δ 1.42-2.40 (m, 12H), 2.60 (m, 1H), 2.80-3.10 (m, 4H), 3.18-3.65 (m, 5H), 4.22 (m, 2H), 6.50 (dd, 1H), 6.59 (d, 1H), 7.18 (s, 1H), 7.21 (d, 1H), 7.39 (m, 2H), 8.06 (m, 1H). APCI MS m/z 478 [MH]⁺ |
| 54 | | 37 white foam | ¹H NMR (400 MHz, CDCl₃): δ 1.82-2.22 (m, 4H), 2.40-3.00 (m, 9H), 3.10 (m, 1H), 3.38-3.90 (m, 6H), 4.36 (m, 2H), 6.60 (dd, 1H), 6.66 (d, 1H), 7.33 (d, 1H), 7.42-7.58 (m, 3H), 8.18 (d, 1H). APCI MS m/z 502 [MNa]⁺ |

EXAMPLE 55

5-Azetidin-3-yl-8-chloro-1-(3,4,5,6-tetrahydro-2H-[1,2']bipyridinyl-4-yl)-5,6-dihydro-4H-2,3,5,10b-tetraaza-benzo[e]azulene

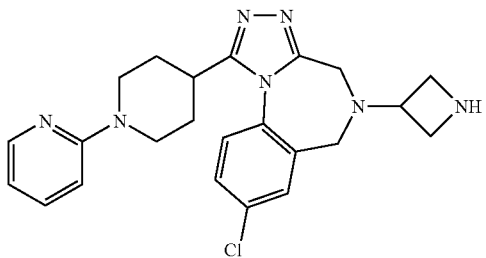

Hydrochloric acid in dioxan (5.6 ml, 4M) was added to a solution of the protected amine from preparation 73 (1.2 g, 2.24 mmol) in dichloromethane (10 ml), and the solution was stirred at room temperature for 18 hours. The mixture was partitioned between 2N sodium hydroxide solution and dichloromethane and the layers were separated. The aqueous phase was extracted with dichloromethane (×2) and the combined organic solutions were washed with brine, dried over magnesium sulphate, and evaporated under reduced pressure. The residual yellow solid was purified by column chromatography on silica gel using dichloromethane:methanol:0.88 ammonia (95:5:0.5 to 93:7:1) to afford the title compound as a white foam (300 mg).

¹H NMR (400 MHz, CDCl₃): δ 1.60-2.20 (m, 4H), 2.82-3.77 (m, 10H), 4.35 (m, 4H), 6.60 (d, 1H), 6.66 (d, 1H), 7.36 (d, 1H), 7.42-7.59 (m, 3H), 8.18 (m, 1H). APCI MS m/z 458 [MNa]⁺

EXAMPLE 56

8-Chloro-5-pyrrolidin-3-yl-1-(3,4,5,6-tetrahydro-2H-[1,2']bipyridinyl-4-yl)-5,6-dihydro-4H-2,3,5,10b-tetraaza-benzo[e]azulene

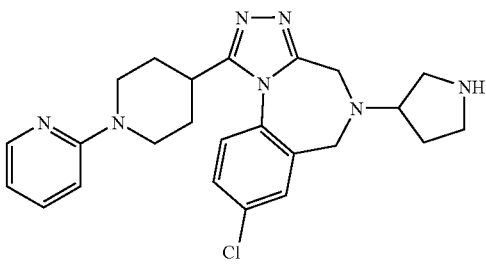

Hydrochloric acid in dioxan (1.5 ml, 4M) was added to a suspension of the protected amine from preparation 74 (767 mg, 1.39 mmol) in dioxan (30 ml) and the reaction mixture was stirred at room temperature for 18 hours. TLC analysis showed starting material remained, so additional hydrochloric acid in dioxan (1.5 ml, 4M) was added and the reaction stirred for a further 5 hours. The mixture was evaporated under reduced pressure and the residue purified by column chromatography on silica gel using dichloromethane:methanol:0.88 ammonia (90:10:1). The residue was azeotroped with ether to afford the title compound as a brown foam, 404.6 mg.

¹H NMR (400 MHz, CDCl₃): δ 1.57-2.39 (m, 9H), 2.78-3.57 (m, 9H), 4.33 (m, 2H), 6.59 (dd, 1H), 6.66 (d, 1H), 7.32 (d, 1H), 7.44 (m, 1H), 7.52 (m, 2H), 8.18 (d, 1H). APCI MS m/z 472 [MNa]⁺

EXAMPLE 57

8-Chloro-5-piperidin-4-yl-1-(3,4,5,6-tetrahydro-2H-[1,2']bipyridinyl-4-yl)-5,6-dihydro-4H-2,3,5,10b-tetraaza-benzo[e]azulene trihydrochloride

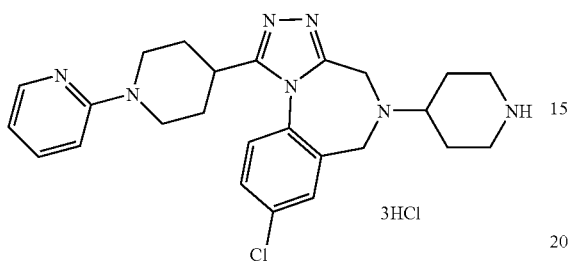

Hydrochloric acid in dioxan (8.44 ml, 4M) was added to a solution of the protected amine from preparation 75 (1.9 g, 3.37 mmol) in dichloromethane (50 ml), and the reaction mixture was stirred at room temperature for 18 hours. The mixture was evaporated under reduced pressure, to give the title compound as a pale pink solid.

$^1$H NMR (400 MHz, CD$_3$OD): δ 1.70-2.35 (m, 6H), 2.55-2.65 (m, 2H), 3.03-3.40 (m, 7H), 3.60-3.96 (m, 2H), 4.20-5.08 (m, 4H), 7.01 (dd, 1H), 7.43 (d, 1H), 7.90 (s, 2H), 7.98 (dd, 1H), 8.04 (m, 2H). APCI MS m/z 464 [MH]$^+$

EXAMPLE 58

8-Chloro-5-[1,4]oxazepan-6-yl-1-(3,4,5,6-tetrahydro-2H-[1,2']bipyridinyl-4-yl)-5,6-dihydro-4H-2,3,5,10b-tetraaza-benzo[e]azulene trihydrochloride

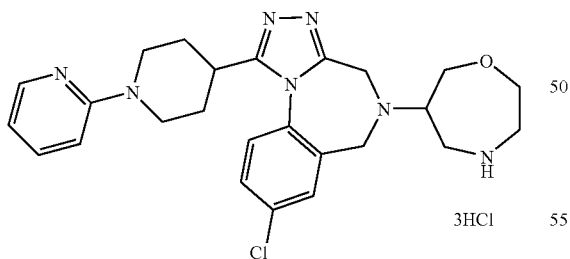

Hydrochloric acid in dioxan (1 ml, 4M) was added to a solution of the protected amine from preparation 76 (180 mg, 0.31 mmol) in dioxan (5 ml), and the reaction mixture was stirred at room temperature for 18 hours. The mixture was evaporated under reduced pressure and the residue purified by column chromatography on silica gel using dichloromethane:methanol:0.88 ammonia (95:5:0.5) as eluant. The product was dissolved in dichloromethane and the solution treated with ethereal hydrochloric acid (1M). The solution was evaporated under reduced pressure to afford the title compound.

$^1$H NMR (400 MHz, CD$_3$OD): δ 2.00-2.60 (m, 4H), 3.36-3.62 (m, 7H), 3.70-4.00 (m, 7H), 4.12-4.40 (m, 4H), 7.01 (dd, 1H), 7.43 (d, 1H), 7.78 (dd, 1H), 7.81 (m, 1H), 7.90 (s, 1H), 7.98 (d, 1H), 8.05 (m, 1H). APCI MS m/z 480 [MH]$^+$

EXAMPLE 59

[8-Chloro-1-(3,4,5,6-tetrahydro-2H-[1,2']bipyridinyl-4-yl)-4H,6H-2,3,5,10b-tetraaza-benzo[e]azulen-5-yl]-morpholin-4-yl-methanone

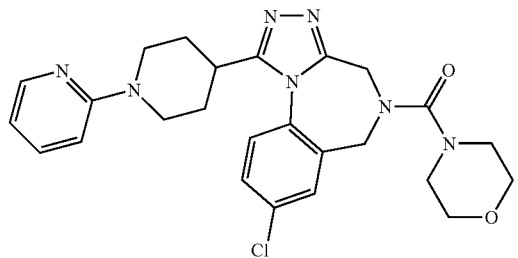

A mixture of the amine from example 4 (150 mg, 0.42 mmol), morpholinecarbonyl chloride (0.15 ml, 1.26 mmol) and triethylamine (0.18 ml, 1.26 mmol) in dichloromethane (10 ml) was stirred at room temperature for 18 hours. The reaction mixture was evaporated under reduced pressure and the residue purified by column chromatography on silica gel using dichloromethane:methanol:0.88 ammonia (95:5:0.5), to afford the title compound as a white solid (130 mg).

$^1$H NMR (400 MHz, CDCl$_3$): δ 1.56-1.85 (m, 4H), 2.85-3.38 (m, 7H), 3.60-3.98 (m, 6H), 4.22-4.54 (m, 3H), 4.78-4.97 (m, 1H), 6.61 (dd, 1H), 6.68 (d, 1H), 7.38 (d, 1H), 7.50 (m, 1H), 7.58 (m, 2H), 8.18 (m, 1H). APCI MS m/z 516 [MNa]$^+$

EXAMPLES 60 TO 63

The following compounds of general structure:

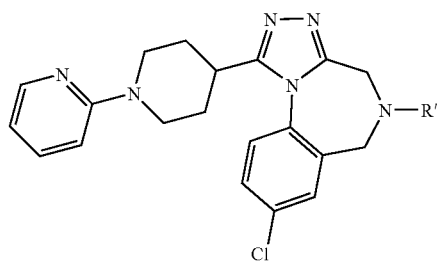

were prepared from the amine from example 4 and the appropriate acid chlorides following the procedure described in example 59.

| Ex No | R¹ | Yield (%)/Form | Data |
|---|---|---|---|
| 60 | 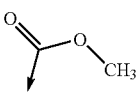 | 83 white solid | ¹H NMR (400 MHz, CDCl₃): δ 1.56-2.38 (m, 4H), 2.80-3.18 (m, 3H), 3.58-3.98 (m, 5H), 4.18-4.46 (m, 2H), 4.79-5.40 (m, 2H), 6.60 (dd, 1H), 6.64 (d, 1H), 7.38 (d, 1H), 7.42 (m, 1H), 7.50-7.61 (m, 2H), 8.17 (m, 1H). APCI MS m/z 461 [MNa]⁺ |
| 61ᵃ | 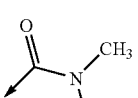 | 92 white solid | ¹H NMR (400 MHz, CDCl₃): δ 1.60-1.95 (m, 2H), 2.05-2.19 (m, 2H), 2.83-3.03 (m, 8H), 3.17 (m, 1H), 3.70-4.05 (m, 2H), 4.19-4.55 (m, 3H), 4.70-5.94 (m, 1H), 6.62 (m, 1H), 6.69 (d, 1H), 7.38 (d, 1H), 7.46 (m, 1H), 7.58 (m, 2H), 8.18 (d, 1H). APCI MS m/z 452 [MH]⁺ |
| 62 |  | 93 white foam | ¹H NMR (400 MHz, CDCl₃): δ 1.58-2.39 (m, 7H), 2.84-3.02 (m, 2H), 3.16 (m, 1H), 3.40 (m, 4H), 3.65-4.00 (m, 2H), 4.20-4.62 (m, 4H), 4.80-5.02 (m, 1H), 6.60 (dd, 1H), 6.66 (d, 1H), 7.38 (d, 1H), 7.42-7.60 (m, 3H), 8.18 (m, 1H). APCI MS m/z 478 [MH]⁺ |
| 63 |  | 69 white solid | ¹H NMR (400 MHz, CDCl₃): δ 1.59-1.95 (m, 3H), 2.18-2.60 (m, 7H), 2.82-3.02 (m, 2H), 3.15 (m, 1H), 3.39 (m, 4H), 3.72-4.02 (m, 2H), 4.20-4.52 (m, 3H), 4.78-4.96 (m, 1H), 6.60 (dd, 1 H), 6.68 (d, 1H), 7.38 (d, 1H), 7.45 (dd, 1H), 7.58 (d, 2H), 8.18 (d, 1H). APCI MS m/z 507 [MH]⁺ |

ᵃisolated without column chromatography

EXAMPLE 64

{2-[8-Chloro-1-(3,4,5,6-tetrahydro-2H-[1,2']bipyridinyl-4-yl)-4H,6H-2,3,5,10b-tetraaza-benzo[e]azulen-5-yl]-ethyl}-dimethyl-amine trihydrochloride

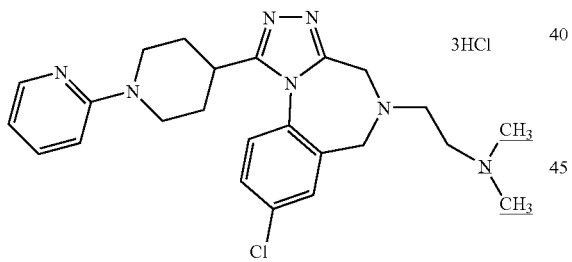

Borane (1M solution in tetrahydrofuran, 4.3 ml, 4.3 mmol) was added to a suspension of the amide from example 61 (398 mg, 0.43 mmol) in tetrahydrofuran (10 ml) and the was mixture heated under reflux for 2 hours. Hydrochloric acid (6M) was added until no more gas was evolved, and the reaction was then heated under reflux for a further 3 hours. The cooled mixture was basified using 2 N sodium hydroxide solution, and then extracted with dichloromethane (3×20 ml). The combined organic extracts were washed with brine (20 ml), dried over magnesium sulphate, and evaporated under reduced pressure. The colourless gum was purified by column chromatography on silica gel using dichloromethane:methanol:0.88 ammonia (93:7:1) as eluant, to afford a colourless gum. This gum was treated with ethereal hydrochloric acid to afford the title compound (194 mg).

¹H NMR (400 MHz, CD₃OD): δ 2.00-2.19 (m, 4H), 3.00 (m, 6H), 3.18 (m, 2H), 3.42-4.46 (m, 11H), 7.00 (dd, 1H), 7.42 (d, 1H), 7.79 (dd, 1H), 7.63 (m, 2H), 7.97 (m, 1H), 8.03 (m, 1H). APCI MS m/z 452 [MH]⁺

EXAMPLE 65

8-Chloro-5-(2-pyrrolidin-1-yl-ethyl)-1-(3,4,5,6-tetrahydro-2H-[1,2']bipyridinyl-4-yl)-5,6-dihydro-4H-2,3,5,10b-tetraaza-benzo[e]azulene trihydrochloride

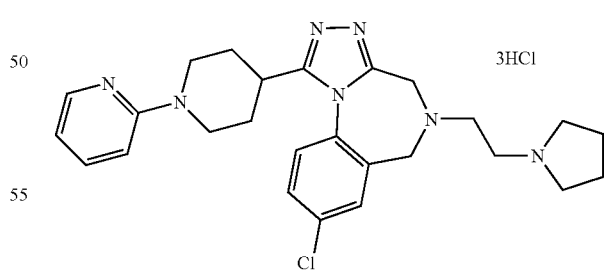

The title compound was obtained in 15% yield from the amide from example 62, following a similar procedure to that described in example 64.

¹H NMR (400 MHz, CD₃OD): δ 2.03-2.23 (m, 8H), 3.00-3.83 (m, 13H), 4.00-4.80 (m, 4H), 7.00 (m, 1H), 7.43 (d, 1H), 7.80-8.08 (m, 5H). APCI MS m/z 478 [MH]⁺

EXAMPLE 66

[8-Chloro-1-(3,4,5,6-tetrahydro-2H-[1,2']bipyridi-nyl-4-yl)-4H,6H-2,3,5,10b-tetraaza-benzo[e]azulen-5-yl]-acetic acid methyl ester

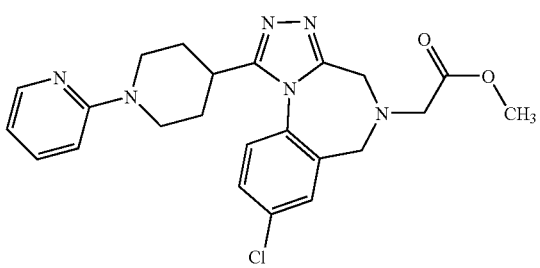

A mixture of the amine from example 4 (500 mg, 1.31 mmol), methyl bromoacetate (260 mg, 1.70 mmol) and potassium carbonate (220 mg, 1.59 mmol) in N,N-dimethylformamide (15 ml) was stirred at room temperature for 72 hours. The mixture was evaporated under reduced pressure and the residue purified directly by column chromatography on silica gel using dichloromethane:methanol (93:7) as eluant to afford the title compound.

$^1$H NMR (400 MHz, CDCl$_3$): δ 1.42-2.40 (m, 4H), 3.00-3.22 (m, 3H), 3.39-3.98 (m, 9H), 4.38 (m, 2H), 6.63 (m, 1H), 6.74 (m, 1H), 7.36 (d, 1H), 7.57 (m, 3H), 8.18 (d, 1H). APCI MS m/z 453 [MH]$^+$

EXAMPLE 67

1-[8-Chloro-1-(3,4,5,6-tetrahydro-2H-[1,2']bipyridi-nyl-4-yl)-4H,6H-2,3,5,10b-tetraaza-benzo[e]azulen-5-yl]-3-methoxy-propan-1-one

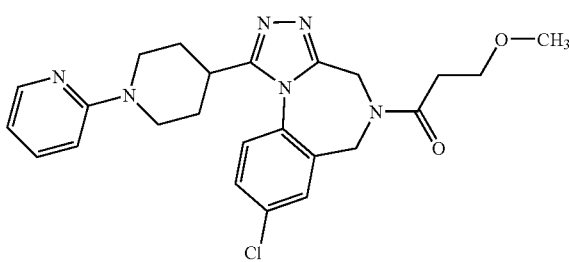

1-(3-Dimethylaminopropyl)-3-ethylcarbodiimide hydrochloride (116 mg, 0.6 mmol) followed by 1-hydroxybenzotriazole hydrate (81 mg, 0.6 mmol) and triethylamine (84 μl, 0.6 mmol) were added to a solution of 3-methoxypropionic acid (63 mg, 0.6 mmol) in dichloromethane (10 ml) and the solution stirred for 10 minutes. The amine from example 4 (150 mg, 0.4 mmol) was added and the reaction stirred at room temperature for 5 hours. The reaction was washed with saturated sodium bicarbonate solution, dried over magnesium sulphate and evaporated under reduced pressure. The residue was purified by column chromatography on silica gel using dichloromethane:methanol:0.88 ammonia (95:5:0.5) to give the title compound as a white solid, 166 mg.

$^1$H NMR (400 MHz, CDCl$_3$): δ 1.57-2.38 (m, 4H), 2.63-3.03 (m, 4H), 3.14 (m, 1H), 3.26 (s, 3H), 3.78-3.98 (m, 3H), 4.23-4.43 (m, 3H), 4.75-4.92 (m, 1H), 5.44-5.62 (m, 1H), 6.61 (dd, 1H), 6.68 (d, 1H), 7.40 (dd, 1H), 7.46 (m, 1H), 7.58 (m, 2H), 8.18 (d, 1H). APCI MS m/z 489 [MNa]$^+$

EXAMPLE 68

1-[8-Chloro-1-(3,4,5,6-tetrahydro-2H-[1,2']bipyridi-nyl-4-yl)-4H,6H-2,3,5,10b-tetraaza-benzo[e]azulen-5-yl]-3-dimethylamino-propan-1-one

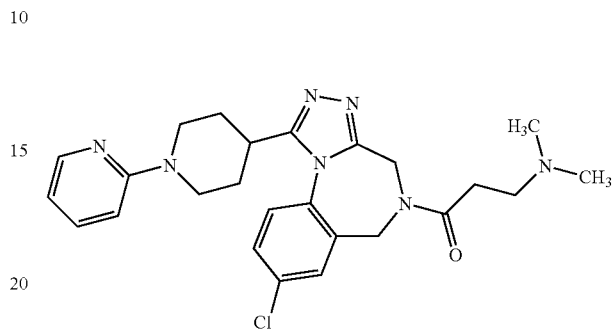

O-(1H-Benzotriazol-1-yl)-N,N,N',N'-tetramethyluronium hexafluorophosphate (200 mg, 0.52 mmol) was added to a solution of 3-dimethylaminopropionic acid hydrochloride (80 mg, 0.52 mmol) in dichloromethane (5 ml) and the solution was stirred for 15 minutes. The amine from example 4 (100 mg, 0.26 mmol) was added and the reaction mixture was stirred at room temperature for 18 hours. The mixture was partitioned between dichloromethane and aqueous sodium bicarbonate solution, and the layers were separated. The organic phase was dried over magnesium sulphate and evaporated under reduced pressure. The crude product was purified by column chromatography on silica gel using dichloromethane:methanol:0.88 ammonia (90:10:1), to afford the title compound as a white solid (110 mg).

$^1$H NMR (400 MHz, CDCl$_3$): δ 1.60-2.00 (m, 2H), 2.20 (m, 3H), 2.38, 2.42 (2×s, 6H), 2.62 (m, 1H), 2.75-3.00 (m, 4H), 3.14 (m, 1H), 3.97-4.80 (m, 4H), 5.05-5.66 (m, 2H), 6.60 (dd, 1H), 6.66 (d, 1H), 7.40 (m, 1H), 7.46 (m, 1H), 7.59 (m, 2H), 8.18 (d, 1H). APCI MS m/z 480 [MH]$^+$

EXAMPLE 69

8-Chloro-5-(1-methyl-pyrrolidin-(2S)-2-ylmethyl)-1-(3,4,5,6-tetrahydro-2H-[1,2']bipyridinyl-4-yl)-5,6-dihydro-4H-2,3,5,10b-tetraaza-benzo[e]azulene tri-hydrochloride

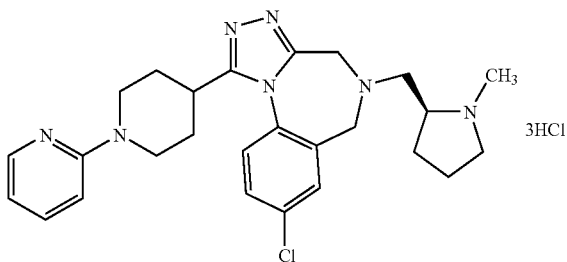

Formaldehyde (0.1 ml, 33 wt. % solution in water) and sodium triacetoxyborohydride (64 mg, 0.30 mmol) were added to a suspension of the amine from example 50 (70 mg, 0.15 mmol) in dichloromethane (5 ml) and the reaction mixture was stirred at room temperature for 2 hours. The mixture was partitioned between dichloromethane and 2 N sodium hydroxide solution and the phases separated. The organic solution was evaporated under reduced pressure and the residue purified by column chromatography on silica gel using dichloromethane:methanol:0.88 ammonia (93:7:1) as eluant. The product was treated with ethereal hydrochloric acid, and the solution evaporated under reduced pressure to give the title compound (35 mg).

$^1$H NMR (400 MHz, CD$_3$OD): δ 1.78-2.98 (m, 9H), 2.96-3.38 (m, 8H), 3.40-4.38 (m, 8H), 7.01 (dd, 1H), 7.43 (d, 1H), 7.80 (m, 1H), 7.89 (m, 2H), 7.98 (d, 1H), 8.06 (dd, 1H). APCI MS m/z 502 [MH]$^+$

EXAMPLES 70 TO 72

The following compounds of general structure:

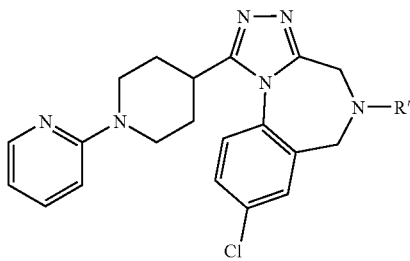

were prepared from the appropriate amines and formaldehyde following a similar procedure to that described in example 69,

EXAMPLE 73 AND 74

(+) and (−) 8-Chloro-5-(4-methyl-morpholin-2-ylmethyl)-1-(3,4,5,6-tetrahydro-2H-[1,2']bipyridinyl-4-yl)-5,6-dihydro-4H-2,3,5,10b-tetraaza-benzo[e]azulene

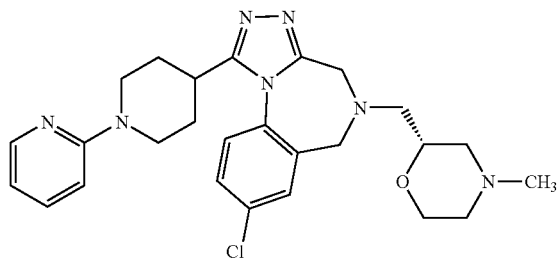

Formaldehyde (0.1 ml, 37 wt. % solution in water) and sodium triacetoxyborohydride (55 mg, 0.26 mmol) were added to a suspension of the amine from example 54 (60 mg, 0.12 mmol) in dichloromethane (5 ml) and the reaction mixture was stirred at room temperature for 2 hours. The mixture was partitioned between dichloromethane and 2 N sodium hydroxide solution and the phases separated. The organic solution was evaporated under reduced pressure and the residue purified by column chromatography on silica gel using dichloromethane:methanol:0.88 ammonia (93:7:1) as eluant. The product was then purified by HPLC using a Chiralcel OD 250×20 mm column, and methanol as eluant to afford the title compound of example 73;

$^1$H NMR (400 MHz, CDCl$_3$): δ 1.60-2.30 (m, 9H), 2.55-2.81 (m, 4H), 2.96 (m, 2H), 3.13 (m, 1H), 3.38-3.98 (m, 7H), 4.37 (m, 2H), 6.60 (dd, 1H), 6.66 (d, 1H), 7.32 (d, 1H), 7.42-7.59 (m, 3H), 8.18 (m, 1H). APCI MS m/z 516 [MNa]$^+$
[α]$_D$=−1.20 (c=0.33, methanol)

| Ex No | R$^1$ | Yield (%)/Form | Data |
|---|---|---|---|
| 70[a] | 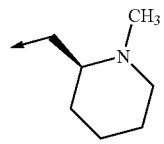 | 67 white foam | $^1$H NMR (400 MHz, CDCl$_3$): δ 1.26 (m, 2H), 1.57 (m, 2H), 1.70-2.47 (m, 10H), 2.80 (m, 2H), 3.96 (m, 2H), 3.12 (m, 1H), 3.27-3.80 (m, 6H), 4.36 (m, 2H), 6.58 (dd, 1H), 6.62 (d, 1H), 7.31 (d, 1H), 7.44 (m, 3H), 8.18 (m, 1H). APCI MS m/z 492 [MH]$^+$ |
| 71[a] | 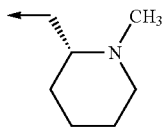 | 70 white foam | $^1$H NMR (400 MHz, CDCl$_3$): δ 1.26 (m, 2H), 1.58 (m, 2H), 1.70-2.45 (m, 10H), 2.79-3.00 (m, 4H), 3.12 (m, 1H), 3.24-3.81 (m, 6H), 4.36 (m, 2H), 6.59 (dd, 1H), 6.62 (d, 1H), 7.31 (d, 1H), 7.41-7.56 (m, 3H), 8.18 (m, 1H). APCI MS m/z 492 [MH]$^+$ |
| 72 | 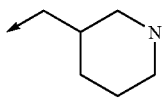 | 57 white foam | $^1$H NMR (400 MHz, CD$_3$OD): δ 1.83-2.62 (m, 8H), 2.81-3.02 (m, 6H), 3.22-3.97 (m, 7H), 4.02-4.98 (m, 6H), 7.00 (dd, 1H), 7.45 (d, 1H), 7.90 (s, 2H), 7.98 (d, 1H), 8.02 (m, 2H). APCI MS m/z 492 [MH]$^+$ |

[a]isolated as the free base and the title compound of example 74.

$^1$H NMR (400 MHz, CDCl$_3$): δ 1.60-2.20 (m, 6H), 2.30 (s, 3H), 2.50-2.79 (m, 4H), 2.96 (m, 2H), 3.13 (m, 1H), 3.20-3.79 (m, 6H), 3.92 (m, 1H), 4.37 (m, 2H), 6.60 (dd, 1H), 6.65 (d, 1H), 7.32 (d, 1H), 7.42-7.59 (m, 3H), 8.18 (m, 1H). APCI MS m/z 516 [MNa]$^+$ [α]$_D$=+3.43 (c=0.23, methanol)

EXAMPLE 75

[8-Chloro-1-(3,4,5,6-tetrahydro-2H-[1,2']bipyridi-nyl-4-yl)-4H,6H-2,3,5,10b-tetraaza-benzo[e]azulen-5-yl]-((2S)-1-methyl-pyrrolidin-2-yl)-methanone

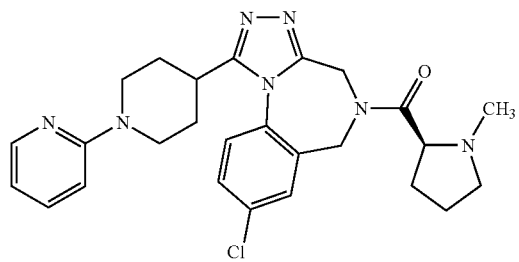

Formaldehyde (37 wt. % in water, 0.1 ml), triethylamine (0.5 ml), acetic acid (0.5 ml) and sodium triacetoxyborohydride (135 mg, 0.63 mmol) were added to a suspension of the amine from example 43 (175 mg, 0.32 mmol) in dichloromethane (10 ml) and the reaction mixture was stirred at room temperature for 1 hour. The mixture was partitioned between dichloromethane (50 ml) and 2 N sodium hydroxide solution (50 ml), and the phases were separated. The organic solution was evaporated under reduced pressure and the residue purified by column chromatography on silica gel using dichloromethane:methanol:0.88 ammonia (95:5:0.5) as eluant, to afford the title compound as a white foam (103 mg).

$^1$H NMR (400 MHz, CDCl$_3$): δ 1.60-2.04 (m, 6H), 2.20-2.52 (m, 5H), 2.84-3.23 (m, 6H), 3.60-4.46 (m, 4H), 5.50-5.85 (m, 2H), 6.60 (dd, 1H), 6.66 (d, 1H), 7.38-7.48 (m, 2H), 7.58-7.63 (m, 2H), 8.18 (m, 1H). APCI MS m/z 492 [MH]$^+$

EXAMPLES 76 TO 81

The following compounds of general structure:

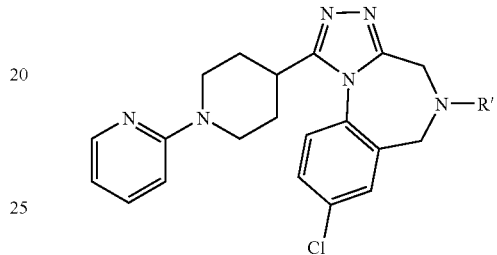

were prepared from the appropriate amines and formaldehyde following a similar procedure to that described in example 75.

| Ex No | R$^1$ | Yield (%)/Form | Data |
|---|---|---|---|
| 76 | (acyl (2S)-1-methyl-pyrrolidin-2-yl) | 57 white foam | $^1$H NMR (400 MHz, CDCl$_3$): δ 1.56-2.40 (m, 11H), 2.83-3.28 (m, 6H), 3.61-3.91 (m, 2H), 4.23-4.42 (m, 2H), 5.46-5.86 (m, 2H), 6.60 (dd, 1H), 6.66 (d, 1 H), 7.37-7.50 (m, 2H), 7.57-7.63 (m, 2H), 8.18(d, 1H). APCI MS m/z 492 [MH]$^+$ Microanalysis found: C, 61.34; H, 6.23; N, 18.93. C$_{26}$H$_{30}$ClN$_7$O;0.25CH$_2$Cl$_2$ requires C, 61.43; H, 5.99; N, 19.10%. |
| 77$^a$ | (acyl 1-methyl-pyrrolidin-3-yl) | 29 | $^1$H NMR (400 MHz, CDCl$_3$): δ 1.58-1.97 (m, 2H), 2.03-2.38 (m, 4H), 2.38-2.60 (m, 4H), 2.70-3.19 (m, 4H), 3.20-3.45 (m, 1 H), 3.63-4.98 (m, 6H), 5.00-5.62 (m, 2H), 6.60 (dd, 1H), 6.66 (d, 1H), 7.38-7.56 (m, 2H), 7.59 (m, 2H), 8.18 (m, 1H). APCI MS m/z 492 [MH]$^+$ |
| 78$^b$ | (acyl (2S)-1-methyl-piperidin-2-yl) | | $^1$H NMR (400 MHz, CD$_3$OD): δ 1.64-2.02 (m, 8H), 2.25 (m, 2H), 2.58 (m, 1H), 2.85 (m, 4H), 3.18-3.60 (m, 3H), 3.80 (m, 1H), 3.98-4.70 (m, 4H), 4.82-5.78 (m, 2H), 7.01 (m, 1H), 7.43 (d, 1H), 7.80-7.95 (m, 3H), 7.98 (d, 1H), 8.04 (m, 1H), 8.20 (br s, 1H). APCI MS m/z 506 [MH]$^+$ |
| 79 | (acyl 1-methyl-piperidin-3-yl) | 59 | $^1$H NMR (400 MHz, CDCl$_3$): δ 1.42-2.38 (m, 11H), 2.61 (m, 1H), 2.77-3.18 (m, 5H), 3.14-4.82 (m, 6H), 5.18-5.60 (m, 2H), 6.60 (dd, 1H), 6.60 (d, 1H), 7.38-7.52 (m, 2H), 7.58 (m, 2H), 8.18 (d, 1H). APCI MS m/z 506 [MH]$^+$ |
| 80 | (acyl 4-methyl-morpholin-2-yl) | 54 | $^1$H NMR (400 MHz, CDCl$_3$): δ 1.58-2.42 (m, 7H), 2.61 -2.76 (m, 1H), 2.81 -3.19 (m, 5H), 3.44-4.52 (m, 8H), 4.99-5.60 (m, 2H), 6.60 (dd, 1H), 6.60 (d, 1H), 7.39 (dd, 1H), 7.45 (dd, 1H), 7.58 (m, 2H), 8.18 (m, 1H). APCI MS m/z 508 [MH]$^+$ |

-continued

| Ex No | R[1] | Yield (%)/Form | Data |
|---|---|---|---|
| 81[a] | 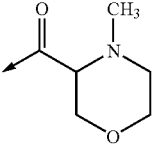 | 62 | $^1$H NMR (400 MHz, CDCl$_3$): δ 1.62-2.42 (m, 8H), 2.79-3.20 (m, 4H), 3.35 (m, 1H), 3.59-3.97 (m, 6H), 4.20-4.42 (m, 2H), 5.00-5.70 (m, 2H), 6.59 (dd, 1H), 6.63 (d, 1H), 7.36-7.45 (m, 2H), 7.58 (m, 2H), 8.16 (m, 1H). APCI MS m/z 508 [MH]$^+$ |

[a]reaction stirred at room temperature for 24 hours
[b]product treated with ethereal HCl to afford the trihydrochloride salt

EXAMPLE 82

8-Chloro-1-(3,4,5,6-tetrahydro-2H-[1,2']bipyridinyl-4-yl)-4H,6H-2,3,5,10b-tetraaza-benzo[e]azulen-5-yl]-(tetrahydro-pyran-4-yl)-methanone

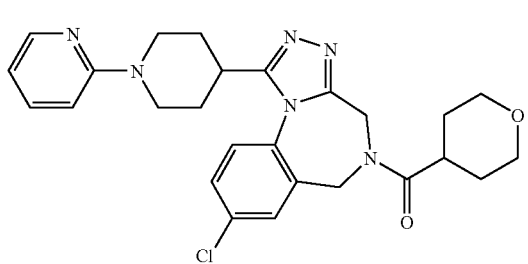

O-(1H-Benzotriazol-1-yl)-N,N,N',N'-tetramethyluronium hexafluorophosphate (243 mg, 0.64 mmol) was added to a solution of tetrahydro-4-pyrancarboxylic acid (J. Med. Chem. 37 (26), 4549, 1994) (82 mg, 0.64 mmol) in dichloromethane (10 ml) and the solution was stirred for 30 minutes. The amine from example 4 (120 mg, 0.32 mmol) was added and the reaction mixture was stirred at room temperature for 18 hours. TLC analysis showed that starting material remained, so additional O-(1H-benzotriazol-1-yl)-N,N,N',N'-tetramethyluronium hexafluorophosphate (122 mg, 0.32 mmol) and tetrahydro-4-pyrancarboxylic acid (41 mg, 0.32 mmol) were added, and the reaction mixture was stirred for a further 24 hours. The mixture was partitioned between dichloromethane and aqueous saturated sodium bicarbonate solution, and the layers separated. The organic phase was dried over magnesium sulphate and evaporated under reduced pressure. The crude product was purified by column chromatography on silica gel using dichloromethane:methanol:0.88 ammonia (95:5:0.5) as eluant, to afford the title compound as a white solid (105 mg).

$^1$H NMR (400 MHz, CDCl$_3$): δ 1.58-2.42 (m, 10H), 2.81 (m, 1H), 2.98-3.22 (m, 4H), 3.50 (m, 2H), 3.97-4.17 (m, 2H), 4.22-4.50 (m, 2H), 5.08-5.46 (m, 1H), 6.60-6.78 (m, 2H), 7.40 (d, 1H), 7.50-7.65 (m, 3H), 8.20 (d, 1H). APCI MS m/z 493 [MH]$^+$

EXAMPLE 83

[8-Chloro-1-(3,4,5,6-tetrahydro-2H-[1,2']bipyridinyl-4-yl)-4H,6H-2,3,5,10b-tetraaza-benzo[e]azulen-5-yl]-(1-methyl-piperidin-4-yl)-methanone

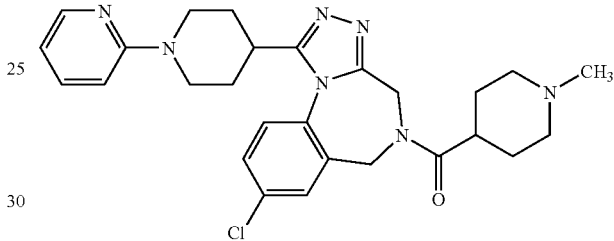

O-(1H-Benzotriazol-1-yl)-N,N,N',N'-tetramethyluronium hexafluorophosphate (395 mg, 1.04 mmol) was added to a solution of 1-methylpiperidine-4-carboxylic acid hydrochloride (210 mg, 1.04 mmol) in dichloromethane (10 ml) and the solution stirred for 30 minutes. The amine from example 4 (200 mg, 0.52 mmol) was added and the reaction mixture was stirred at room temperature for 18 hours. The mixture was washed with aqueous sodium carbonate solution and the organic solution was dried over magnesium sulphate. The solution was evaporated under reduced pressure and the crude product was purified by column chromatography on silica gel using ethyl acetate:methanol:0.88 ammonia (90:10:1) as eluant, to afford the title compound as a white solid (195 mg).
APCI MS m/z 506 [MH]$^+$

EXAMPLE 84

8-Chloro-5-(1-methyl-azetidin-3-yl)-1-(3,4,5,6-tetrahydro-2H-[1,2']bipyridinyl-4-yl)-5,6-dihydro-4H-2,3,5,10b-tetraaza-benzo[e]azulene

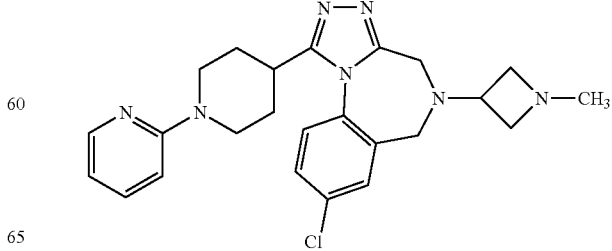

Formaldehyde (37% in water, 0.1 ml), triethylamine (0.5 ml), acetic acid (0.5 ml) and sodium triacetoxyborohydride (75 mg, 0.36 mmol) were added to a suspension of the amine from example 55 (77 mg, 0.18 mmol) in dichloromethane (10 ml), and the reaction mixture was stirred at room temperature for 3 hours. The mixture was partitioned between dichloromethane and 2 N sodium hydroxide solution, and the phases were separated. The aqueous layer was extracted with further dichloromethane and the combined organic solutions evaporated under reduced pressure. The residue was purified by column chromatography on silica gel using dichloromethane:methanol:0.88 ammonia (95:5:0.5) as eluant, to afford the title compound as a white foam (72 mg).

$^1$H NMR (400 MHz, CDCl$_3$): δ 1.79-2.21 (m, 4H), 2.40 (s, 3H), 2.83-3.78 (m, 12H), 4.34 (m, 2H), 6.60 (dd, 1H), 6.66 (d, 1H), 7.34 (d, 1H), 7.42-7.58 (m, 3H), 8.18 (d, 1H). APCI MS m/z 450 [MH]$^+$

EXAMPLES 85 TO 88

The following compounds of general structure:

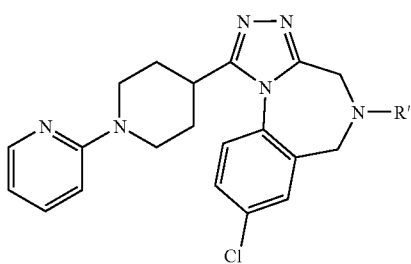

were prepared from the appropriate amines and aldehydes or ketones following a similar procedure to that described in example 84.

EXAMPLE 89

8-Chloro-5-(1-methyl-pyrrolidin-3-yl)-1-(3,4,5,6-tetrahydro-2H-[1,2']bipyridinyl-4-yl)-5,6-dihydro-4H-2,3,5,10b-tetraaza-benzo[e]azulene

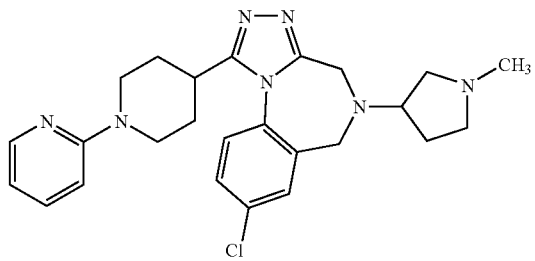

Formaldehyde (18 μl, 37 wt. % solution in water, 0.22 mmol) and sodium triacetoxyborohydride (47 mg, 0.22 mmol) were added to a solution of the amine from example 56 (100 mg, 0.22 mmol) in dichloromethane (5 ml), and the reaction mixture was stirred at room temperature for 30 minutes. Saturated aqueous sodium bicarbonate solution (10 ml) was added, the mixture was stirred vigorously for 10 minutes, and the layers were separated. The organic layer was evaporated under reduced pressure and the residue purified by column chromatography on silica gel using dichloromethane: methanol: 0.88 ammonia (95:5:0.5) as eluant. The product was azeotroped with ether to afford the title compound (60 mg).

$^1$H NMR (400 MHz, CDCl$_3$): δ 1.74-2.30 (m, 8H), 2.34 (s, 3H), 2.45 (s, 1H), 2.57 (d, 1H), 2.66 (d, 1H), 2.80 (t, 1H), 2.93 (s, 2H), 3.12 (t, 1H), 3.23 (t, 1H), 3.48 (s, 2H), 4.33 (s, 2H), 6.60 (t, 1H), 6.64 (d, 1H), 7.32 (d, 1H), 7.45 (t, 1H), 7.52 (m, 2H), 8.15 (d, 1H). APCI MS m/z 564 [MH]$^+$

| Ex No | R$^1$ | Yield (%)/Form | Data |
|---|---|---|---|
| 85 | azetidine-N-CH(CH$_3$)$_2$ | 62 white foam | $^1$H NMR (400 MHz, CDCl$_3$): δ 0.95 (d, 6H), 1.78-2.40 (m, 5H), 2.86-3.60 (m, 12H), 4.36 (m, 2H), 6.60 (dd, 1H), 6.65 (d, 1H), 7.34 (d, 1H), 7.44 (m, 2H), 7.53 (d, 1H), 8.18 (d, 1H). APCI MS m/z 478 [MH]$^+$ |
| 86 | piperidine-N-CH$_3$ | 29 | $^1$H NMR (400 MHz, CDCl$_3$): δ 1.60-2.08 (m, 8H), 2.25 (s, 3H), 2.51 (m, 1H), 2.80-3.01 (m, 4H), 3.17 (m, 1H), 3.40-3.96 (m, 6H), 4.36 (m, 2H), 6.60 (m, 1H), 6.66 (d, 1H), 7.30 (d, 1H), 7.41-7.58 (m, 3H), 8.18 (d, 1H). APCI MS m/z 478 [MH]$^+$ |
| 87 | piperidine-N-CH$_2$CH$_3$ | 32 | $^1$H NMR (400 MHz, CDCl$_3$): δ 1.10 (t, 3H), 1.54-2.10 (m, 8H), 2.40 (q, 2H), 2.54 (m, 1H), 2.76-3.03 (m, 6H), 3.17 (m, 1H), 3.42-4.96 (m, 4H), 4.36 (m, 2H), 6.60 (m, 1H), 6.66 (d, 1H), 7.30 (d, 1H), 7.41-7.58 (m, 3H), 8.18 (d, 1H). APCI MS m/z 492 [MH]$^+$ |
| 88 | piperidine-N-CH(CH$_3$)$_2$ | 30 | $^1$H NMR (400 MHz, CDCl$_3$): δ 1.10 (d, 6H), 1.72-2.38 (m, 8H), 2.58 (m, 1H), 2.78-3.03 (m; 7H), 3.14 (m, 1H), 3.38-4.00 (m, 4H), 4.36 (m, 2H), 6.60 (m, 1H), 6.66 (d, 1H), 7.30 (d, 1H), 7.41-7.58 (m, 3H), 8.18 (d, 1H). APCI MS m/z 528 [MNa]$^+$ |

EXAMPLE 90

8-Chloro-5-(1-isopropyl-pyrrolidin-3-yl)-1-(3,4,5,6-tetrahydro-2H-[1,2']bipyridinyl-4-yl)-5,6-dihydro-4H-2,3,5,10b-tetraaza-benzo[e]azulene trihydrochloride

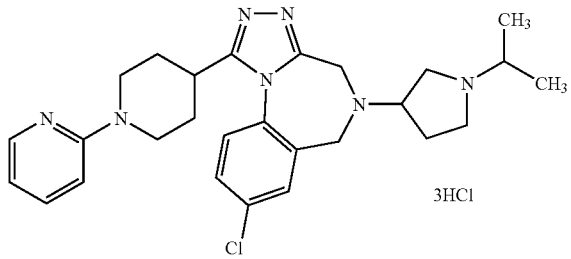

Acetone (0.1 ml) and sodium triacetoxyborohydride (47 mg, 0.22 mmol) were added to a solution of the amine from example 56 (100 mg, 0.22 mmol) in dichloromethane (5 ml), and the reaction mixture was stirred at room temperature for 16 hours. Saturated aqueous sodium bicarbonate solution (10 ml) was added, the mixture was stirred vigorously for 10 minutes, and the layers were separated. The organic layer was evaporated under reduced pressure and the residue purified by column chromatography on silica gel using dichloromethane:methanol:0.88 ammonia (95:5:0.5) as eluant. The product was treated with ethereal hydrochloric acid to afford the title compound.

$^1$H NMR (400 MHz, CD$_3$OD): δ 1.43 (d, 6H), 1.85-2.70 (m, 4H), 3.35-4.85 (m, 17H), 7.02 (t, 1H), 7.47 (d, 1H), 7.80-7.92 (m, 2H), 7.97 (d, 2H), 8.06 (t, 1H). APCI m/z 492 [MH]$^+$

EXAMPLE 91

2-[8-Chloro-1-(1-pyrimidin-2-yl-piperidin-4-yl)-4H,6H-2,3,5,10b-tetraaza-benzo[e]azulen-5-yl]-ethanol

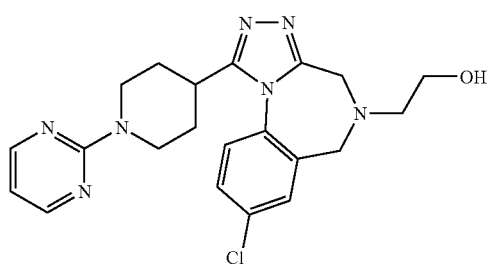

N,N-Diisopropylethylamine (80 μl, 0.62 mmol), followed by 2-chloroethanol (52 μl, 0.78 mmol) were added to a solution of the amine from example 12 (200 mg, 0.52 mmol) in N,N-dimethylformamide (6 ml), and the reaction mixture was stirred at room temperature for 18 hours. The mixture was concentrated under reduced pressure and the residue was purified by column chromatography on silica gel using ethyl acetate:methanol:0.88 ammonia (90:10:1) as eluant, to give the title compound as an off-white solid (120 mg).

$^1$H NMR (400 MHz, CDCl$_3$): δ 1.62-2.22 (m, 3H), 2.62 (m, 1H), 2.84 (m, 2H), 3.00 (m, 2H), 3.18 (m, 1H), 3.38-3.90 (m, 6H), 4.80 (m, 2H), 6.46 (m, 1H), 7.38 (d, 1H), 7.58 (m, 2H), 8.30 (s, 2H). APCI MS m/z 426 [MH]$^+$

EXAMPLE 92

8-Chloro-5-(2-methoxy-ethyl)-1-(1-pyrimidin-2-yl-piperidin-4-yl)-5,6-dihydro-4H-2,3,5,10b-tetraaza-benzo[e]azulene

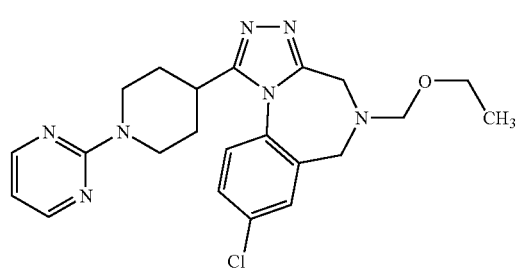

N,N-Diisopropylethylamine (80 μl, 0.62 mmol), followed by 2-bromomethoxyethane (0.2 ml, 0.62 mmol) were added to a solution of the amine from example 12 (200 mg, 0.52 mmol) in N,N-dimethylformamide (6 ml) and the reaction mixture was stirred at 80° C. for 18 hours. The mixture was concentrated under reduced pressure and the residue purified by column chromatography on silica gel using ethyl acetate:methanol:0.88 ammonia (95:5:0.5) to give the title compound as a gum (76 mg).

$^1$H NMR (400 MHz, CDCl$_3$): δ 1.84-2.16 (m, 4H), 2.78-3.20 (m, 5H), 3.20-4.50 (m, 9H), 4.80 (m, 2H), 6.48 (dd, 1H), 7.32 (d, 1H), 7.58 (m, 2H), 8.30 (d, 2H). APCI MS m/z 462 [MNa]$^+$

EXAMPLE 93

8-Chloro-5-pyrimidin-2-yl-1-(3,4,5,6-tetrahydro-2H-[1,2']bipyridinyl-4-yl)-5,6-dihydro-4H-2,3,5,10b-tetraaza-benzo[e]azulene

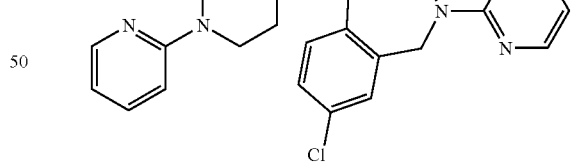

A mixture of the amine from example 4 (200 mg, 0.53 mmol), 2-chloropyrimidine (66 mg, 0.58 mmol) and potassium carbonate (72 mg, 0.53 mmol) in N,N-dimethylformamide (5 ml) was stirred at room temperature for 18 hours. TLC analysis showed starting materials remained, so additional 2-chloropyrimidine (66 mg, 0.58 mmol) was added, and the reaction was stirred at 80° C. for a further 72 hours. The cooled mixture was evaporated under reduced pressure, the residue was partitioned between ethyl acetate and brine, and the layers were separated. The organic layer was washed with water, wash with ammonium chloride solution, dried over magnesium sulphate and then evaporated under reduced pressure. The residual yellow oil was purified by column chromatography on silica gel using dichloromethane:methanol (95:5) as eluant, to afford the title compound as a yellow oil (117 mg).

¹H NMR (400 MHz, CDCl₃): δ 1.61-2.40 (m, 4H), 2.82-3.19 (m, 3H), 3.63-4.48 (m, 4H), 5.60-5.84 (m, 2H), 6.60 (m, 2H), 6.66 (d, 1H), 7.40 (d, 1H), 7.43 (m, 1H), 7.52 (m, 1H), 7.60 (s, 1H), 8.16 (m, 1H), 8.38 (d, 2H). APCI m/z 459 [MH]⁺

EXAMPLE 94

8-Chloro-5-pyrimidin-4-yl-1-(3,4,5,6-tetrahydro-2H-[1,2']bipyridinyl-4-yl)-5,6-dihydro-4H-2,3,5,10b-tetraaza-benzo[e]azulene

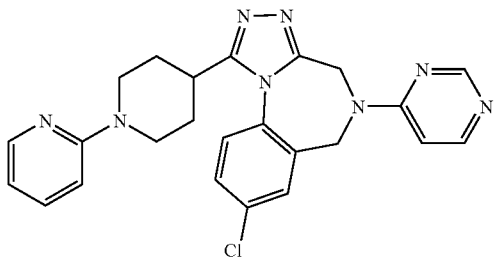

A mixture of the amine from example 4 (500 mg, 1.3 mmol), potassium carbonate (480 mg, 3.5 mmol) and 4-chloropyrimidine (300 mg, 2.6 mmol) was stirred at 95° C. for 18 hours. The cooled reaction mixture was diluted with ethyl acetate and the solution was washed with brine (5×), then dried over magnesium sulphate and concentrated under reduced pressure. The crude product was purified by column chromatography on silica gel using dichloromethane:methanol (100:0 to 95:5) as eluant, and the product was triturated with diethyl ether to afford the title compound (80 mg).

¹H NMR (400 MHz, CDCl₃): δ 1.80-2.24 (m, 4H), 2.97 (m, 2H), 3.18 (m, 1H), 3.90-4.43 (m, 4H), 5.20-5.80 (m, 2H), 6.56 (d, 1H), 6.60 (m, 1H), 6.66 (d, 1H), 7.42 (m, 2H), 7.57 (d, 1H), 7.62 (s, 1H), 8.18 (m, 1H), 8.32 (d, 1H), 8.70 (s, 1H). APCI m/z 459 [MH]⁺

EXAMPLE 95

8-Chloro-1-(3,4,5,6-tetrahydro-2H-[1,2']bipyridinyl-4-yl)-4H,6H-2,3,5,10b-tetraaza-benzo[e]azulene-5-carbaldehyde

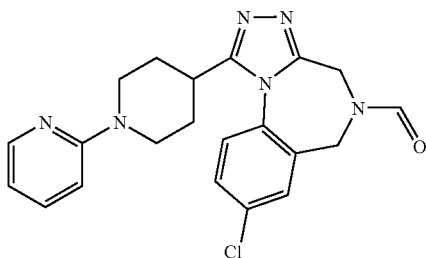

A solution of the amine from example 4 (300 mg, 0.79 mmol) in formic acid (15 ml) was stirred at 80° C. for 3 hours. The cooled mixture was concentrated under reduced pressure and the residue was partitioned between ethyl acetate and sodium bicarbonate solution. The layers were separated, and the organic phase was evaporated under reduced pressure to give the title compound.

¹H NMR (400 MHz, CDCl₃): δ 1.60-2.42 (m, 4H), 2.98-3.24 (m, 3H), 3.78-4.58 (m, 5H), 5.43 (m, 1H), 6.62 (m, 1H), 6.75 (m, 1H), 7.40 (m, 1H), 7.55 (m, 1H), 7.60 (d, 1H), 8.18 (m, 1H), 8.21 (d, 1H). APCI m/z 409 [MH]⁺

EXAMPLE 96

8-Chloro-1-(3,4,5,6-tetrahydro-2H-[1,2']bipyridinyl-4-yl)-4H,6H-2,3,5,10b-tetraaza-benzo[e]azulene-5-sulphonic acid dimethylamide

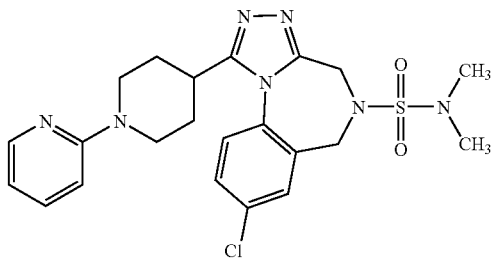

Dimethylsulphamoyl chloride (0.12 ml, 1.08 mmol) was added to a solution of the amine from example 4 (140 mg, 0.36 mmol) and pyridine (90 μl, 1.08 mmol) in dichloromethane (8 ml), and the reaction mixture was stirred at room temperature for 18 hours. TLC analysis showed that starting material remained, so additional dimethylsulphamoyl chloride (0.08 ml, 0.72 mmol) was added and the mixture was stirred for a further 24 hours. The mixture was washed with saturated aqueous sodium bicarbonate solution, dried over magnesium sulphate, and evaporated under reduced pressure. The crude product was purified by column chromatography on silica gel using dichloromethane:methanol:0.88 ammonia (95:5:0.5) as eluant, to afford the title compound as a pale yellow gum (120 mg).

¹H NMR (400 MHz, CDCl₃): δ 1.58-1.94 (m, 2H), 2.10-2.40 (m, 2H), 2.78-3.02 (m, 8H), 3.15 (m, 1H), 3.62-4.00 (m, 2H), 4.21-4.97 (m, 4H), 6.60 (dd, 1H), 6.67 (d, 1H), 7.39 (d, 1H), 7.47 (dd, 1H), 7.59 (d, 1H), 7.62 (s, 1H), 8.19 (d, 1H). APCI MS m/z 488 [MH]⁺

EXAMPLE 97

8-Chloro-5-pyridin-2-ylmethyl-1-(1-pyrimidin-2-yl-piperidin-4-yl)-5,6-dihydro-4H-2,3,5,10b-tetraaza-benzo[e]azulene

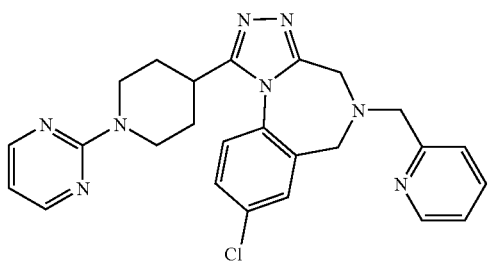

Sodium triacetoxyborohydride (277 mg, 1.31 mmol) was added to a mixture of the amine from example 12 (250 mg, 0.65 mmol), 2-pyridine carboxaldehyde (105 mg, 0.98 mmol), and acetic acid (3 drops) in dichloromethane (5 ml), cooled to 5° C., and the reaction mixture was then stirred at room temperature for 18 hours. 0.88 Ammonia was added to the reaction mixture, the phases were separated and the organic layer was dried over magnesium sulphate and evaporated under reduced pressure. The crude product was purified by column chromatography on silica gel using dichloromethane:methanol (95:5) as eluant, to afford the title compound (167 mg)

$^1$H NMR (400 MHz, CDCl$_3$): δ 1.78-2.26 (m, 4H), 3.00, 3.18 (2×m, 4H), 3.35-3.60, 3.80-3.98 (2×m, 5H), 4.80 (m, 2H), 6.48 (dd, 1H), 7.22 (m, 1H), 7.37 (d, 1H), 7.53 (m, 3H), 7.75 (m, 1H), 8.30 (s, 2H), 8.60 (d, 1H). APCI MS m/z 473 [MH]$^+$

EXAMPLES 98 TO 99

The following compounds of general structure:

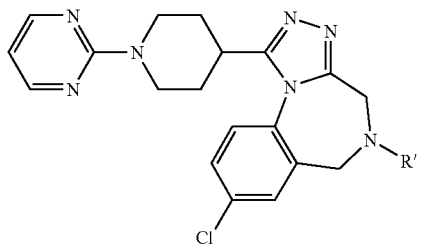

were prepared from the appropriate amines following a similar procedure to that described in example 97.

| Ex No | R$^1$ | Data |
|---|---|---|
| 98 | ![thiazolylmethyl] | $^1$H NMR (400 MHz, CDCl$_3$): δ 1.79-2.12 (m, 4H), 3.00 (m, 2H), 3.18 (m, 1H), 3.26-3.64 (m, 3H), 4.06 (m, 3H), 4.65-5.00 (m, 3H), 6.45 (s, 1H), 7.35 (m, 3H), 7.50 (s, 1H), 7.58 (d, 1H), 8.28 (d, 2H). APCI MS m/z 479 [MH]$^+$ |
| 99 | ![pyrazolylmethyl] | $^1$H NMR (400 MHz, CDCl$_3$): δ 1.75-2.25 (m, 4H), 2.99 (m, 2H), 3.18 (m, 1H), 3.20-4.06 (m, 6H), 4.79 (m, 2H), 6.33 (s, 1H), 6.45 (m, 1H), 7.35 (d, 1H), 7.52 (m, 3H), 8.26 (m, 2H). APCI MS m/z 462 [MH]$^+$ |

EXAMPLE 100

8-Chloro-1-(1-pyrimidin-2-yl-piperidin-4-yl)-4H,6H-2,3,5,10b-tetraaza-benzo[e]azulene-5-sulphonic acid dimethylamide

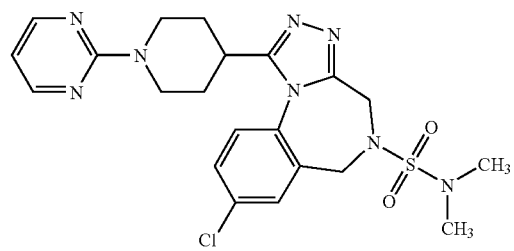

N,N-Diisopropylethylamine (77 μl, 0.44 mmol), followed by dimethylsulphamoyl chloride (50 μl, 0.44 mmol) were added to an ice-cold solution of the amine from example 12 (150 mg, 0.4 mmol) in dichloromethane (10 ml), and the reaction mixture was stirred at room temperature for 4 hours. TLC analysis showed that starting material remained, so additional dimethylsulphamoyl chloride (91 μl, 0.8 mmol) and N,N-diisopropylethylamine (140 μl, 0.8 mmol) were added, and the mixture was stirred at room temperature for a further 18 hours. The mixture was evaporated under reduced pressure, the residue was partitioned between dichloromethane and aqueous sodium bicarbonate solution, the layers were separated, and the organic phase was evaporated under reduced pressure. The crude product was purified by column chromatography on silica gel using dichloromethane:methanol:0.88 ammonia (95:5:0.5) as eluant, to afford the title compound as an off-white solid (135 mg).

$^1$H NMR (400 MHz, CDCl$_3$): δ 1.58-1.89 (m, 2H), 2.16-2.35 (m, 2H), 2.83-3.19 (m, 9H), 3.63-3.99 (m, 2H), 4.59-4.97 (m, 4H), 6.50 (dd, 1H), 7.38 (d, 1H), 7.59 (d, 1H), 7.63 (s, 1H), 8.30 (d, 2H). APCI MS m/z 489 [MH]$^+$

EXAMPLE 101

8-Chloro-5-methyl-1-(3,4,5,6-tetrahydro-2H-[1,2']bipyridinyl-4-yl)-4,5-dihydro-2,3,5,10b-tetraaza-benzo[e]azulen-6-one

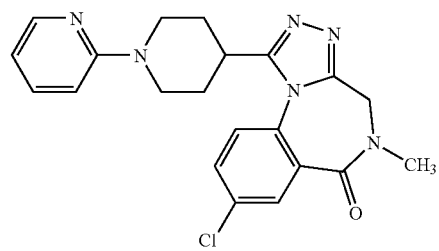

Acetic acid (2 drops) was added to a solution of the amine from preparation 62 (250 mg, 0.59 mmol) in toluene (6 ml), and the reaction mixture was stirred under reflux for 3 hours. The cooled mixture was purified directly by column chromatography on silica gel using ethyl acetate:dichloromethane:methanol (100:0:0 to 0:95:5) as eluant. The product was azeotroped with dichloromethane (2×10 ml) and ether (4×10 ml) to give the title compound as a white foam (151 mg).

$^1$H NMR (400 MHz, DMSOd$_6$): δ 1.45 (m, 2H), 1.92 (m, 2H), 2.74 (m, 1H), 2.85-3.35 (m, 5H), 4.10 (m, 1H), 4.32-4.60 (m, 3H), 6.51 (m, 1H), 6.74 (d, 1H), 7.42 (m, 1H), 7.61-7.84 (m, 3H), 8.00 (s, 1H). APCI m/z 409 [MH]$^+$

EXAMPLE 102

13-Chloro-9-methyl-3-(3,4,5,6-tetrahydro-2H-[1,2']bipyridinyl-4-yl)-2,4,5,9-tetraaza-tricyclo[9.4.0.0*2,6*]pentadeca-1(11),3,5,12,14-pentaene

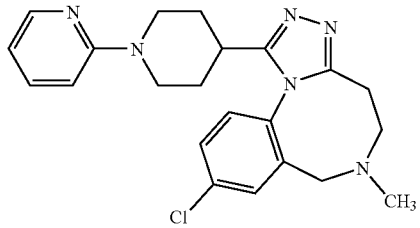

A mixture of the compound from preparation 80 (140 mg, 0.55 mmol) and the hydrazide from preparation 1 (121 mg, 0.55 mmol) in ethanol (2 ml) was heated under reflux for 23 hours, then allowed to cool. The mixture was concentrated under reduced pressure and the residue was purified by column chromatography on silica gel using an elution gradient of dichloromethane:methanol:0.88 ammonia (100:0:0 to 90:10:1). The product was dissolved in dichloromethane (6 ml) and the solution was treated with polymer bound isocyanate (0.6 g, 1.5 mmol/g), and the mixture was stirred for 1 hour. The mixture was filtered and the filtrate was evaporated under reduced pressure, to afford the title compound (57 mg).

$^1$H NMR (400 MHz, CDCl$_3$): δ 1.42 (m, 1H), 1.63 (m, 1H), 2.18 (m, 1H), 2.30 (m, 2H), 2.42 (s, 3H), 2.78 (m, 2H), 2.83-3.05 (m, 3H), 3.18 (m, 2H), 3.61 (d, 1H), 4.18 (m, 1H), 4.39 (m, 1H), 6.58 (m, 1H), 6.62 (d, 1H), 7.19 (d, 1H), 7.42 (m, 2H), 7.52 (s, 1H), 8.14 (m, 1H). APCI MS m/z 409 [MH]$^+$

EXAMPLE 103

13-Chloro-8-methyl-3-(1-pyrimidin-2-yl-piperidin-4-yl)-2,4,5,8-tetraaza-tricyclo[9.4.0.0*2,6*]pentadeca-1(11),3,5,12,14-pentaene

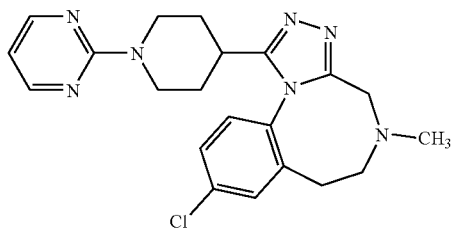

Trifluoroacetic acid (1.5 ml) was added to a solution of the compound from preparation 63 (1.60 g, 3.72 mmol) in toluene (100 ml), and the mixture was stirred at 60° C. for 24 hours. The cooled mixture was concentrated under reduced pressure and the residue was partitioned between dichloromethane and sodium bicarbonate solution. The layers were separated, the organic phase was dried over magnesium sulphate, and evaporated under reduced pressure. The residual oil was purified by column chromatography on silica gel using dichloromethane:methanol (95:5) as eluant. The product was suspended in dichloromethane (100 ml), and treated with activated carbon. The mixture was filtered, the filtrate was evaporated under reduced pressure, and the residue was purified by column chromatography on silica gel using dichloromethane:methanol (96:4) as eluant, to afford the title compound as an oil (469 mg).

$^1$H NMR (400 MHz, CDCl$_3$): δ 1.42 (m, 1H), 1.62 (m, 1H), 2.18 (m, 1H), 2.25 (m, 2H), 2.42 (s, 3H), 2.60 (m, 1H), 2.80 (m, 2H), 2.93-3.01 (m, 2H), 3.28 (m, 2H), 4.20 (d, 1H), 4.60 (m, 1H), 4.86 (m, 1H), 6.45 (dd, 1H), 7.18 (d, 1H), 7.40 (d, 2H), 8.27 (d, 2H). APCI MS m/z 410 [MH]$^+$

EXAMPLE 104

8-Chloro-5,6-dimethyl-1-(1-pyrimidin-2-yl-piperidin-4-yl)-5,6-dihydro-4H-2,3,5,10b-tetraaza-benzo[e]azulene

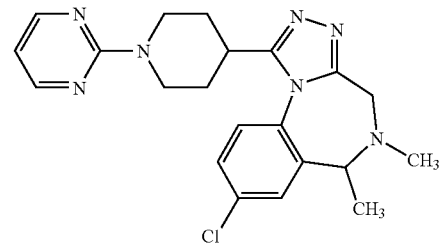

Trifluoroacetic acid (0.5 ml) was added to a solution of the compound from preparation 64 (0.9 g, 2.10 mmol) in toluene (10 ml), and the reaction mixture was stirred at 100° C. for 18 hours. The cooled mixture was washed with sodium bicarbonate solution and brine then evaporated under reduced pressure. The residue was purified by column chromatography on silica gel using dichloromethane:methanol (95:5) as eluant, to afford the title compound as a white foam (530 mg).

$^1$H NMR (400 MHz, C$_2$D$_2$Cl$_4$, at 373K): δ 1.23 (d, 3H), 1.82 (m, 2H), 2.03 (m, 2H), 2.40 (s, 3H), 3.01-3.19 (m, 3H), 3.29 (m, 1H), 3.49 (m, 1H), 3.63 (m, 1H), 4.64 (m, 1H), 4.78 (m, 1H), 6.42 (m, 1H), 7.24 (d, 1H), 7.50 (m, 2H), 8.26 (d, 2H). APCI MS m/z 432 [MNa]$^+$

EXAMPLE 105

1-(3,4,5,6-Tetrahydro-2H-[1,2']bipyridinyl-4-yl)-8-trifluoromethyl-4H,6H-5-oxa-2,3,10b-triaza-benzo[e]azulene

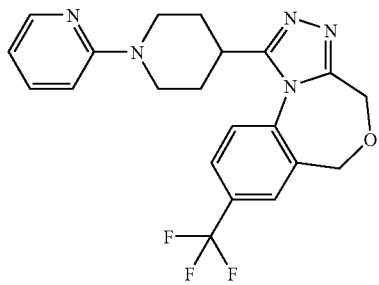

Sodium hydride (81 mg, 60% dispersion in mineral oil, 2.03 mmol) was added to an ice-cooled solution of 2-amino-5-trifluoromethylphenyl methanol (WO 99/05147, pg 60) (350 mg, 1.8 mmol) in tetrahydrofuran (20 ml), and the solution was stirred at 0° C. for 30 minutes. A solution of the chloride from preparation 5 (560 mg, 2.0 mmol) in tetrahydrofuran (10 ml) was added dropwise, and once addition was complete the reaction mixture was stirred at room temperature for 5 hours. The reaction mixture was quenched with water (2 ml) and the mixture was partitioned between dichloromethane and sodium bicarbonate solution. The layers were separated, the organic phase was dried over magnesium sulphate and evaporated under reduced pressure. The crude product was purified by column chromatography on silica gel using dichloromethane:methanol:0.88 ammonia (95:5:0.5) as eluant, to afford a white solid (560 mg).

A mixture of this solid in xylene (20 ml) and p-toluene sulphonic acid (40 mg) was stirred at 140° C. for 18 hours. The cooled solution was evaporated under reduced pressure and the residue was purified by column chromatography on silica gel using ethyl acetate:methanol:0.88 ammonia (97:3:0.3 to 90:10:1) as eluant, to afford the title compound as a pale yellow solid (210 mg).

$^1$H NMR (400 MHz, MeOD): δ 1.98 (m, 4H), 2.98 (m, 2H), 3.41 (m, 1H), 4.37 (m, 2H), 4.57 (s, 2H), 4.61 (s, 2H), 6.64 (m, 1H), 6.63 (d, 1H), 7.58 (m, 1H), 7.98 (d, 1H), 8.03 (m, 3H). APCI MS m/z 416 [MH]$^+$

EXAMPLE 106

10-Chloro-1-(3,4,5,6-tetrahydro-2H-[1,2']bipyridinyl-4-yl)-6,7-dihydro-4H-5,8-dioxa-2,3,12b-triaza-benzo[a]cyclopenta[c]cyclononene

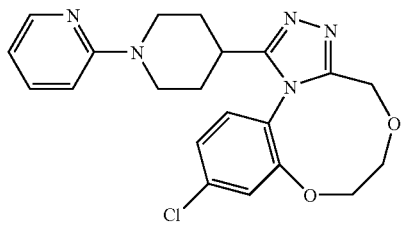

A mixture of the compound from preparation 61 (250 mg, 0.58 mmol) and p-toluenesulphonic acid (cat) in xylene (75 ml) was stirred at 140° C. for 24 hours. The cooled mixture was concentrated under reduced pressure and the residue was purified by column chromatography on silica gel using dichloromethane:methanol:0.88 ammonia (95:5:0.5) as eluant, and purified again using ethyl acetate:methanol:0.88 ammonia (95:5:0.5 to 90:10:1) as eluant, to afford the title compound as an off-white foam (42 mg).

$^1$H NMR (400 MHz, MeOD): δ 1.30 (m, 2H), 2.04 (m, 2H), 2.74-2.98 (m, 3H), 3.70 (m, 1H), 3.81 (m, 1H), 4.19 (m, 3H), 4.37 (m, 1H), 4.50 (m, 1H), 4.78 (m, 1H), 6.62 (m, 1H), 6.82 (d, 1H), 7.36 (m, 1H), 7.48 (m, 2H), 7.58 (m, 1H), 8.02 (m, 1H). APCI MS m/z 412 [MH]$^+$

EXAMPLE 107

8-Chloro-1-(3,4,5,6-tetrahydro-2H-[1,2']bipyridinyl-4-yl)-4H,6H-5-thia-2,3,10b-triaza-benzo[e]azulene

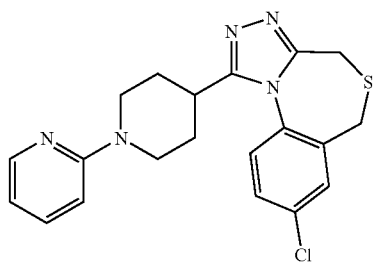

To a solution of the thioamide of preparation 87 (581 mg, 2.53 mmol) in butan-1-ol (20 ml) was added the hydrazide of preparation 1 (557 mg, 2.53 mmol), and the mixture was heated to 100° C. for 20 hours. The reaction mixture was evaporated under reduced pressure and the residue was purified by column chromatography on silica gel using dichloromethane: Methanol (95:5) as eluant, to afford the title compound as an off-white foam (825 mg)

$^1$H NMR (400 MHz, CDCl$_3$): δ 1.60 (m, 1H), 1.65 (m, 1H), 2.20 (m, 1H), 2.40 (m, 1H), 2.80 (m, 1H), 3.00 (m, 2H), 3.40 (d, 1H), 3.60 (m, 2H), 4.00 (d, 1H), 4.20 (d, 1H), 4.40 (d, 1H), 6.60 (dd, 1H), 6.65 (d, 1H), 7.25 (d, 1H), 7.45 (m, 3H), 8.20 (d, 1H) APCI MS m/z 398 [MH]$^+$

EXAMPLE 108

8-Chloro-1-(3,4,5,6-tetrahydro-2H-[1,2']bipyridinyl-4-yl)-4H,6H-5-thia-2,3,10b-triaza-benzo[e]azulene 5-oxide

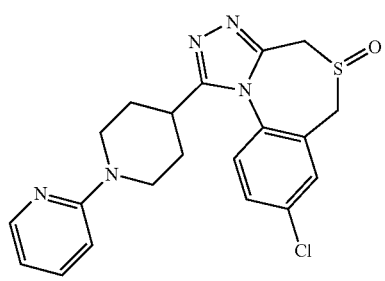

To a solution of the sulphide of example 107 (150 mg, 0.38 mmol) in 1,1,1,3,3,3-Hexafluoro-propan-2-ol (5 ml) was added a 30% aqueous solution of hydrogen peroxide (0.09 ml). The resulting reaction mixture was stirred at room temperature for 1 hour before partitioning with aqueous sodium sulfite. The organic layer was washed with brine, dried (MgSO$_4$), filtered and evaporated. The resulting residue was purified by column chromatography on silica gel using dichloromethane:Methanol:0.880 ammonia (95:5:0.5) as eluant, to afford the title compound as an off-white foam (64 mg)

$^1$H NMR (400 MHz, CDCl$_3$): δ 1.55 (m, 1H), 1.75 (m, 1H), 2.20 (m, 1H), 2.30 (m, 1H), 2.82 (m, 1H), 3.03 (m, 2H), 3.18 (d, 1H) 3.28 (d, 1H), 3.90 (d, 1H), 4.22 (m, 1H), 4.42 (m, 1H), 5.02 (d, 1H), 6.60 (dd, 1H), 6.65 (d, 1H), 7.40 (d, 1H), 7.45 (t, 1H), 7.60 (m, 2H), 8.18(d, 1H) APCI MS m/z 436 [MH]$^+$

EXAMPLE 109

8-Chloro-1-(3,4,5,6-tetrahydro-2H-[1,2']bipyridinyl-4-yl)-4H,6H-5-thia-2,3,10b-triaza-benzo[e]azulene 5,5-dioxide

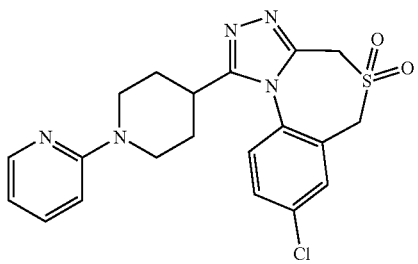

To a solution of the sulphide of example 107 (150 mg, 0.38 mmol) in 1,1,1-trifluroacetic acid (5 ml) was added a 30% aqueous solution of hydrogen peroxide (0.09 ml). The resulting reaction mixture was stirred at room temperature for 1 hour before it was diluted with aqueous sodium hydrogen carbonate solution and extracted with ethyl acetate (2×50 ml). The organic layer was washed with brine, dried (MgSO$_4$), filtered and evaporated, to afford the title compound as an off-white solid (108 mg)

$^1$H NMR (400 MHz, CDCl$_3$): δ 1.80 (m, 1H), 2.20 (m, 1H), 2.30 (m, 1H), 2.82 (m, 1H), 3.03 (m, 2H), 3.95 (d, 1H), 4.10 (m, 2H), 4.25 (m, 1H), 4.40 (m, 1H), 4.80 (dd, 1H), 6.65 (m, 2H), 7.405 (m, 2H), 7.70 (m, 2H), 8.20 (d, 1H) APCI MS m/z 452 [MH]$^+$

EXAMPLE 110

Examples of specific compounds, tested in screen 1.0 ($V_{1A}$ filter binding assay) as described above, are illustrated in the table below

| Example No. | Ki (nM) |
|---|---|
| 5 | 4.66 |
| 6 | 2.37 |
| 8 | 2.47 |
| 11 | 0.68 |
| 13 | 13.86 |
| 15 | 4.71 |
| 24 | 1.00 |

-continued

| Example No. | Ki (nM) |
|---|---|
| 27 | 1.25 |
| 38 | 4.63 |
| 59 | 1.32 |
| 73 & 74 | 6.84 & 6.02 |
| 93 | 2.33 |
| 96 | 0.24 |
| 100 | 0.77 |
| 102 | 4.16 |
| 103 | 2.02 |

The invention claimed is:

1. A compound of formula (II) or a pharmaceutically acceptable salt thereof:

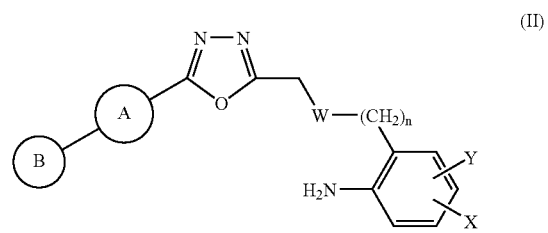

(II)

wherein:
W is —O—, —S(O)$_a$—, or —N(R$^1$)—
R$^1$ is H, C$_{1-6}$ alkyl, (CH$_2$)$_b$COR$^2$, CO(CH$_2$)$_b$NR$^2$R$^3$, SO$_2$R$^2$, (CH$_2$)$_c$OR$^2$, (CH$_2$)$_c$NR$^2$R$^3$, or (CH$_2$)$_b$het$^1$;
het$^1$ is a saturated or unsaturated heterocycle of from 3 to 8 atoms containing one to four heteroatoms selected from O, N, or S, optionally substituted with C$_{1-6}$ alkyl;
X and Y are each independently H, C$_{1-6}$ alkyl, halogen, OH, CF$_3$, OCF$_3$, or OR$^4$;
Ring A is a 4-7 membered, saturated N-containing heterocycle, optionally substituted with OH, and in which optionally at least one ring N is substituted with O;
Ring B is phenyl or a 4-7 membered unsaturated N-containing heterocycle, optionally substituted with OH, halogen, CN, CONH$_2$, CF$_3$, or OCF$_3$, and in which optionally at least one ring N is substituted with O;
R$^2$ and R$^3$ are each independently H, C$_{1-6}$ alkyl, C$_{1-6}$ alkyloxy, N(C$_{1-6}$ alkyl)$_2$, or C$_{3-8}$ cycloalkyl; wherein said C$_{1-6}$ alkyl is optionally substituted with OH, halogen, N(C$_{1-6}$ alkyl)$_2$, or C$_{1-6}$ alkyloxy;
or R$^2$ and R$^3$ are taken together with the nitrogen atom to which they are attached to form a heterocycle of from 3 to 8 atoms, optionally substituted with C$_{1-6}$ alkyl;
R$^4$ is C$_{1-6}$ alkyl;
a, n and c are each independently 0, 1, or 2; and
b is 0 or 1.

2. The compound of claim 1 selected from the group consisting of:
2-({[5-(3,4,5,6-Tetrahydro-2H-[1,2']bipyridinyl-4-yl)-[1,3,4]oxadiazol-2-ylmethyl]-amino}-methyl)-phenylamine;
4-Chloro-2-({[5-(3,4,5,6-tetrahydro-2H-[1,2']bipyridinyl-4-yl)-[1,3,4]oxadiazol-2-ylmethyl]-amino}-methyl)-phenylamine;
4-Chloro-2-({[5-(1-pyrimidin-2-yl-piperidin-4-yl)-[1,3,4]oxadiazol-2-ylmethyly]-amino}-methyl)-phenylamine;
2-[5-(3,4,5,6-Tetrahydro-2H-[1,2']bipyridinyl-4-yl)-[1,3,4]oxadiazol-2-ylmethoxymethyl]-phenylamine;

3-Chloro-2-[5-(3,4,5,6-tetrahydro-2H-[1,2']bipyridinyl-4-yl)-[1,3,4]oxadiazol-2-ylmethoxymethyl]-phenylamine;
5-Chloro-2-[5-(3,4,5,6-tetrahydro-2H-[1,2']bipyridinyl-4-yl)-[1,3,4]oxadiazol-2-ylmethoxymethyl]-phenylamine;
4-Methoxy-2-[5-(3,4,5,6-tetrahydro-2H-[1,2']bipyridinyl-4-yl)-[1,3,4]oxadiazol-2-ylmethoxymethyl]-phenylamine;
4-Chloro-2-[5-(3,4,5,6-tetrahydro-2H-[1,2']bipyridinyl-4-yl)-[1,3,4]oxadiazol-2-ylmethoxymethyl]-phenylamine;
2-{2-[5-(3,4,5,6-Tetrahydro-2H-[1,2']bipyridinyl-4-yl)-[1,3,4]oxadiazol-2-ylmethoxy]-ethyl}-phenylamine;
4-Chloro-2-{2-[5-(3,4,5,6-tetrahydro-2H-[1,2']bipyridinyl-4-yl)-[1,3,4]oxadiazol-2-ylmethoxy]-ethyl}-phenylamine;
4-Chloro-2-[5-(1-pyrimidin-2-yl-piperidin-4-yl)-[1,3,4]oxadiazol-2-ylmethoxymethyl]-phenylamine;
2-{2-[5-(1-Pyrimidin-2-yl-piperidin-4-yl)-[1,3,4]oxadiazol-2-ylmethoxy]-ethyl}-phenylamine;
4-Fluoro-2-[5-(3,4,5,6-tetrahydro-2H-[1,2']bipyridinyl-4-yl)-[1,3,4]oxadiazol-2-ylmethoxymethyl]-phenylamine;
4,5-difluoro-2-[5-(3,4,5,6-tetrahydro-2H-[1,2']bipyridinyl-4-yl)-[1,3,4]oxadiazol-2-ylmethoxymethyl]-phenylamine;
2-[5-(3,4,5,6-Tetrahydro-2H-[1,2']bipyridinyl-4-yl)-[1,3,4]oxadiazol-2-ylmethoxymethyl]-4-trifluoromethoxy-phenylamine;
4-Methyl-2-[5-(3,4,5,6-tetrahydro-2H-[1,2']bipyridinyl-4-yl)-[1,3,4]oxadiazol-2-ylmethoxymethyl]-phenylamine;
4-Chloro-2-(2-{[5-(3,4,5,6-tetrahydro-2H-[1,2']bipyridinyl-4-yl)-[1,3,4]oxadiazol-2-ylmethyl]-amino}-ethyl)-phenylamine;
4-Chloro-2-{2-[5-(3,4,5,6-tetrahydro-2H-[1,2']bipyridinyl-4-yl)-[1,3,4]oxadiazol-2-ylmethoxy]-ethoxy}-phenylamine;
4-Chloro-2-(2-{methyl-[5-(1-pyrimidin-2-yl-piperidin-4-yl)-[1,3,4]oxadiazol-2-ylmethyl]-amino}-ethyl)-phenylamine; and
(2-amino-5-chlorobenzyl)methyl{[5-(1-pyridin-2-ylpiperidin-4-yl)-1,3,4-oxadiazol-2-yl]methyl}amine; or a pharmaceutically acceptable salt thereof.

* * * * *